US007923592B2

(12) United States Patent
Tonkovich et al.

(10) Patent No.: US 7,923,592 B2
(45) Date of Patent: Apr. 12, 2011

(54) PROCESS FOR MAKING UNSATURATED HYDROCARBONS USING MICROCHANNEL PROCESS TECHNOLOGY

(75) Inventors: Anna Lee Tonkovich, Dublin, OH (US); Thomas Yuschak, Lewis Center, OH (US); Timothy J. LaPlante, Columbus, OH (US); Scott Rankin, Columbus, OH (US); Steven T. Perry, Galloway, OH (US); Sean Patrick Fitzgerald, Columbus, OH (US); Wayne W. Simmons, Dublin, OH (US); Terry Mazanec, Solon, OH (US); Eric Daymo, Dublin, OH (US)

(73) Assignee: Velocys, Inc., Plain City, OH (US)

( * ) Notice: Subject to any disclaimer, the term of this patent is extended or adjusted under 35 U.S.C. 154(b) by 912 days.

(21) Appl. No.: 11/670,608

(22) Filed: Feb. 2, 2007

(65) Prior Publication Data

US 2008/0184915 A1 Aug. 7, 2008

(51) Int. Cl.
*C07C 4/04* (2006.01)
*C07C 5/32* (2006.01)
(52) U.S. Cl. ........ 585/654; 585/656; 585/648; 585/649; 585/650; 585/652
(58) Field of Classification Search .......... None
See application file for complete search history.

(56) References Cited

U.S. PATENT DOCUMENTS

| | | | |
|---|---|---|---|
| 3,882,049 A | 5/1975 | Bertolacini et al. | |
| 3,972,837 A | 8/1976 | Acres et al. | |
| 4,089,810 A | 5/1978 | Diwell et al. | |
| 4,096,095 A | 6/1978 | Cairns | |
| 4,289,652 A | 9/1981 | Hunter et al. | |
| 5,248,251 A | 9/1993 | Dalla Betta et al. | |
| 5,382,741 A * | 1/1995 | Astbury et al. | 585/652 |
| 5,811,062 A | 9/1998 | Wegeng et al. | 422/129 |
| 6,040,266 A | 3/2000 | Fay, III et al. | |
| 6,126,723 A | 10/2000 | Drost et al. | 96/4 |
| 6,192,596 B1 | 2/2001 | Bennett et al. | 34/76 |
| 6,200,536 B1 | 3/2001 | Tonkovich et al. | 422/177 |
| 6,284,217 B1 | 9/2001 | Wang et al. | 423/651 |

(Continued)

FOREIGN PATENT DOCUMENTS

DE 246257 6/1987

(Continued)

OTHER PUBLICATIONS

International Search Report and Written Opinion, Application No. PCT/US2008/052547, mailed Jun. 20, 2008.

(Continued)

*Primary Examiner* — Tam M Nguyen
(74) *Attorney, Agent, or Firm* — Renner, Otto, Boisselle & Sklar, LLP

(57) ABSTRACT

The disclosed invention relates to a process for converting a feed composition comprising one or more hydrocarbons to a product comprising one or more unsaturated hydrocarbons, the process comprising: flowing the feed composition and steam in contact with each other in a microchannel reactor at a temperature in the range from about 200° C. to about 1200° C. to convert the feed composition to the product, the process being characterized by the absence of catalyst for converting the one or more hydrocarbons to one or more unsaturated hydrocarbons. Hydrogen and/or oxygen may be combined with the feed composition and steam.

57 Claims, 21 Drawing Sheets

U.S. PATENT DOCUMENTS

| | | |
|---|---|---|
| 6,440,895 B1 | 8/2002 | Tonkovich et al. ............ 502/439 |
| 6,451,864 B1 | 9/2002 | Wang et al. .................... 518/715 |
| 6,479,428 B1 | 11/2002 | Tonkovich et al. ............ 502/302 |
| 6,488,838 B1 | 12/2002 | Tonkovich et al. ............ 208/108 |
| 6,490,812 B1 | 12/2002 | Bennett et al. .................... 34/433 |
| 6,491,880 B1 | 12/2002 | Wang et al. .................... 422/211 |
| 6,503,298 B1 | 1/2003 | Monzyk et al. .................... 95/96 |
| 6,508,862 B1 | 1/2003 | Tonkovich et al. ............ 95/106 |
| 6,533,840 B2 | 3/2003 | Martin et al. ...................... 95/45 |
| 6,540,975 B2 | 4/2003 | Tonkovich et al. ............ 423/659 |
| 6,558,634 B1 | 5/2003 | Wang et al. .................... 422/173 |
| 6,607,678 B2 | 8/2003 | Wang et al. .................... 252/373 |
| 6,616,909 B1 | 9/2003 | Tonkovich et al. ........ 423/848.1 |
| 6,622,519 B1 | 9/2003 | Mathias et al. .................. 62/611 |
| 6,652,627 B1 | 11/2003 | Tonkovich et al. ............ 95/104 |
| 6,660,237 B2 | 12/2003 | Wang et al. .................... 422/222 |
| 6,666,909 B1 | 12/2003 | TeGrotenhuis et al. ......... 95/273 |
| 6,680,044 B1 | 1/2004 | Tonkovich et al. ............ 423/652 |
| 6,734,137 B2 | 5/2004 | Wang et al. .................... 502/328 |
| 6,762,149 B2 | 7/2004 | Tonkovich et al. ............ 502/439 |
| 6,814,781 B2 | 11/2004 | Tonkovich et al. ................ 95/90 |
| 6,851,171 B2 | 2/2005 | Schmitt ............................ 29/469 |
| 6,875,247 B2 | 4/2005 | TeGrotenhuis et al. ......... 55/319 |
| 6,969,505 B2 | 11/2005 | Tonkovich et al. ........ 423/648.1 |
| 6,969,506 B2 | 11/2005 | Tonkovich et al. ............ 423/652 |
| 6,984,363 B2 | 1/2006 | Tonkovich et al. ............ 422/173 |
| 6,989,134 B2 | 1/2006 | Tonkovich et al. ............ 422/189 |
| 7,000,427 B2 | 2/2006 | Mathias et al. .................. 62/612 |
| 7,008,969 B2 | 3/2006 | Wang et al. .................... 518/715 |
| 7,014,835 B2 | 3/2006 | Mathias et al. ................ 423/652 |
| 7,029,647 B2 | 4/2006 | Tonkovich et al. ............ 423/584 |
| 7,045,114 B2 | 5/2006 | Tonkovich et al. ............ 423/659 |
| 7,077,643 B2 | 7/2006 | Holladay et al. .............. 431/215 |
| 7,084,180 B2 | 8/2006 | Wang et al. .................... 518/712 |
| 7,220,390 B2 | 5/2007 | Tonkovich et al. ............ 422/172 |
| 7,234,514 B2 | 6/2007 | Vogel ............................ 165/170 |
| 7,250,074 B2 | 7/2007 | Tonkovich et al. ............. 95/130 |
| 7,255,845 B2 | 8/2007 | Tonkovich et al. ........ 423/437.2 |
| 2003/0116503 A1 | 6/2003 | Wang et al. .................... 210/660 |
| 2003/0219903 A1 | 11/2003 | Wang et al. ...................... 436/37 |
| 2004/0034266 A1 | 2/2004 | Brophy et al. ................. 585/658 |
| 2004/0220434 A1 | 11/2004 | Brophy et al. ................. 568/959 |
| 2004/0228882 A1 | 11/2004 | Qiu et al. ........................ 424/400 |
| 2004/0229752 A1 | 11/2004 | Long et al. .................... 502/303 |
| 2004/0234566 A1 | 11/2004 | Qiu et al. ........................ 424/401 |
| 2005/0087767 A1 | 4/2005 | Fitzgerald et al. ............. 257/200 |
| 2005/0176832 A1 | 8/2005 | Tonkovich et al. ............ 518/726 |
| 2005/0272965 A1 | 12/2005 | Watson et al. |
| 2006/0016215 A1 | 1/2006 | Tonkovich et al. .............. 62/617 |
| 2006/0016216 A1 | 1/2006 | Tonkovich et al. .............. 62/617 |
| 2006/0036106 A1 | 2/2006 | Mazanec et al. ............... 549/533 |
| 2006/0073080 A1 | 4/2006 | Tonkovich et al. ............ 422/100 |
| 2006/0102519 A1 | 5/2006 | Tonkovich et al. ............ 208/107 |
| 2006/0120213 A1 | 6/2006 | Tonkovich et al. ............ 366/144 |
| 2006/0129015 A1 | 6/2006 | Tonkovich et al. ............ 585/709 |
| 2006/0249020 A1 | 11/2006 | Tonkovich et al. ............. 95/115 |
| 2007/0004810 A1 | 1/2007 | Wang et al. .................... 518/718 |
| 2007/0085227 A1 | 4/2007 | Tonkovich et al. ............ 261/127 |

FOREIGN PATENT DOCUMENTS

| | | |
|---|---|---|
| DE | 3926466 | 2/1991 |
| EP | 1102628 | 11/2006 |
| GB | 1531134 | 11/1978 |
| GB | 2077136 | 12/1981 |
| WO | 9421372 | 9/1994 |
| WO | 9700442 | 1/1997 |
| WO | 9828073 | 7/1998 |
| WO | 9838147 | 9/1998 |
| WO | 9916542 | 4/1999 |
| WO | 0006301 | 2/2000 |
| WO | 03006149 | 1/2003 |
| WO | 03/106386 | 12/2003 |
| WO | 2004/091772 A1 | 10/2004 |
| WO | 2006/127889 | 11/2006 |
| ZA | 855317 | 7/1985 |

OTHER PUBLICATIONS

Kandlikar; "Exploring Roughness Effect on Laminar Internal Flow—Are We Ready for Change?"; Nanoscale and Microscale Thermophysical Engineering; 2008; pp. 61-82; vol. 12; Taylor & Francis Group, LLC.

Ellob et al.; "Intensification of the Steam Cracking Process"; Newcastle University; Apr. 26, 2007.

International Preliminary Report on Patentability, Application No. PCT/US2008/052547, mailed May 28, 2009.

Chen et al.; "Performance analysis of a folding flow micromixer"; Microfluid Nanofluid (2009) 6:763-774.

MacInnes et al.; "Investigation of alternating-flow mixing in microchannels"; Chemical Engineering Science 60; 2005; pp. 3453-3467.

MacInnes et al.; "Numerical characterization of floding flow microchannel mixers"; Chemical Engineering Science 62; 2007; pp. 2718-2727.

MacInnes et al.; "Mixing Strategies for Flow in Microchannel Devices"; Chemical and Process Engineering, University of Sheffield, Nov. 24, 2004.

Cybulski et al.; "Monoliths in Heterogeneous Catalysis"; Catal. Rev.—Sci. Eng., 36(2), 179-270 (1994).

Bennett et al.; "Microchannel cooled heatsinks for high average power laser diode arrays"; SPIE, vol. 1865;1993; pp. 144-153.

Beretta et al.; "Production of olefins via oxidative dehydrogenation of light paraffins at short contact times"; Catalysis Today 64 (2001) 103-111.

Iglesia; "Design, synthesis, and use of cobalt-base Fischer-Tropsch synthesis catalysts"; Applied Catalysis A: General 161 (1997); pp. 59-78.

* cited by examiner

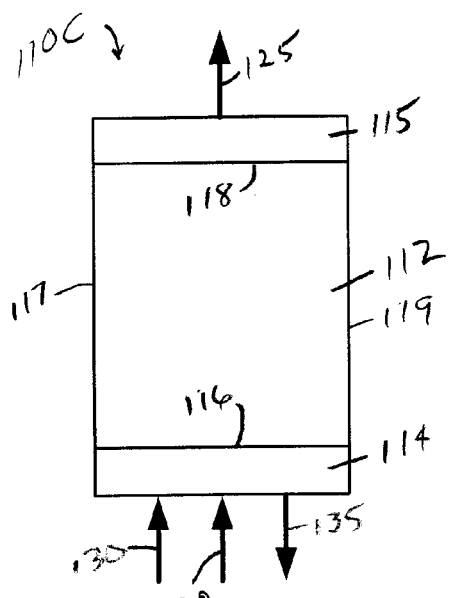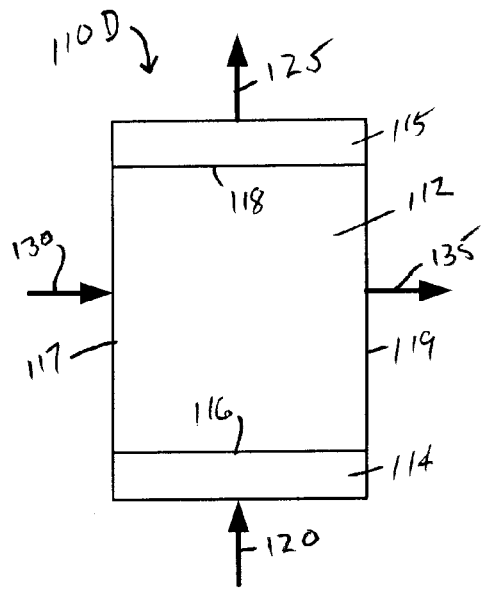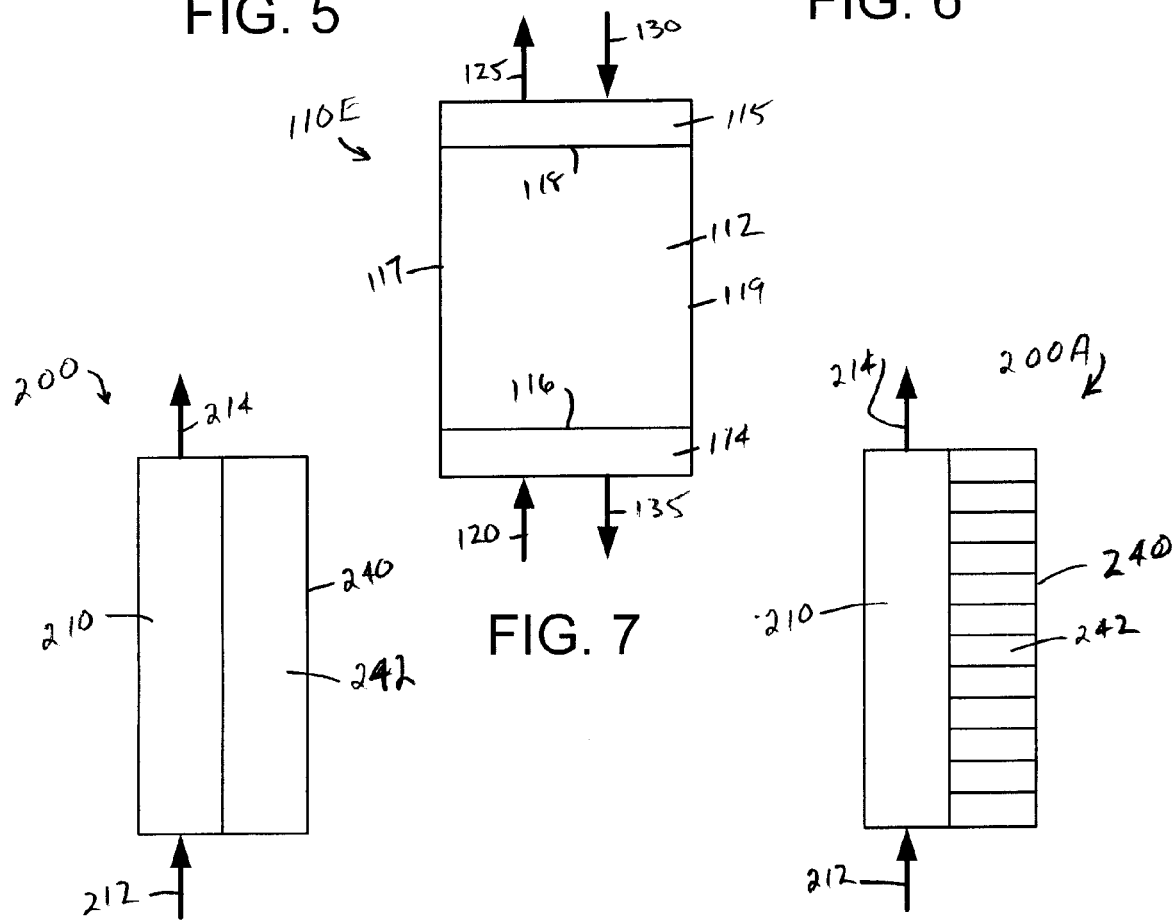

PROCESS FOR MAKING UNSATURATED HYDROCARBONS USING MICROCHANNEL PROCESS TECHNOLOGY

This invention was made with Government support under Contract DE-FC36-046014154 awarded by the United States Department of Energy. The Government has certain rights in this invention.

TECHNICAL FIELD

This invention relates to processes using microchannel process technology for converting hydrocarbons, for example, saturated hydrocarbons, to unsaturated hydrocarbons. The processes may be referred to as cracking processes, dehydrogenation processes, and the like. These processes are characterized by the absence of catalysts for converting the hydrocarbons to unsaturated hydrocarbons.

BACKGROUND

Unsaturated hydrocarbons, such as ethylene, propylene, butylene, isobutylene, and the like, are intermediates that are useful in the petrochemical industry. In order to satisfy market demand, substantial efforts have been invested in the production of such compounds by conventional thermal steam cracking of alkanes and naphtha and by catalytic dehydrogenation methods. However, conventional steam cracking is equilibrium limited and requires very high temperatures (which may exceed 700° C. for the conversion of light hydrocarbons) to achieve a high enough conversion to be economically viable. Even so, temperatures are limited by available alloys to temperatures at which single pass yields are still relatively low. Steam cracking also requires the input of large amounts of heat to drive the gas reaction which is endothermic. Because of the equilibrium limitations, steam cracking is often carried out at low pressures, typically one atmosphere or less, and usually requires cooling and compression of the product stream to effect separation and recovery of the unsaturated hydrocarbons.

Conventional catalytic dehydrogenation has similar disadvantages, including the need for high reaction temperatures (e.g., 550 to over 700° C. depending on the feedstock), the deactivation of the catalyst by coke formation, and the consequent need for continuous or periodic catalyst regeneration at frequent intervals throughout the process. In addition, there are thermodynamic limitations in conventional dehydrogenation. These thermodynamic limitations are due to the fact that conversion in conventional dehydrogenation processes are equilibrium limited, and require high temperature and low pressure to achieve high single pass yields. As a result of these substantial drawbacks, the petroleum industry has sought a solution to the demand for olefinic hydrocarbons in the use of autothermal cracking and catalytic oxidative dehydrogenation methods.

In autothermal cracking, oxygen or air is added to the feed and partially combusts part of the feed in situ generating the high temperatures required to thermally crack the remaining feedstock. In some variants a catalyst is used to support combustion with the catalyst being in the form of a fixed bed or a fluidized or spouted bed. In some cases hydrogen is co-fed with the feedstock and is found to increase olefin yields. Autothermal cracking usually takes place at high temperatures (550-1200° C.) and requires very short reaction times and rapid quenching of the products to preserve the olefinic products and prevent further undesirable reactions. Even so, by-products are typically formed including carbon oxides. At higher pressure, yields of undesirable by-products increase. At very high temperatures as encountered in some autothermal processes, hydrocarbon cracking to methane also reduces selectivity to useful olefinic products.

Catalytic oxidative dehydrogenation is, in principle, not subject to many of the problems associated with conventional steam cracking or catalytic dehydrogenation because of the presence of oxygen in the reaction mixture. One route of oxidative dehydrogenation uses oxygen to react with the hydrogen released from the hydrocarbon, in situ, so that the aforementioned equilibrium limitation is removed, and high single pass yields can be achieved. The reaction is exothermic overall and does not require a supply of heat as in endothermic dehydrogenation reactions. Generally, in a catalytic oxidative dehydrogenation process, the reactants (hydrocarbon and an oxygen-containing gas) are passed over a catalyst to produce an olefin product. Typically, the hydrocarbon is a saturated hydrocarbon such as ethane or a mixture of saturated hydrocarbons. The hydrocarbon may be gaseous or liquid at ambient temperature and pressure but is typically gaseous. However, there are no reported commercial oxidative dehydrogenation processes operating at this time and despite extensive research, there remains a need for new oxidative dehydrogenation catalysts, catalytic systems, and methods that achieve high conversion at high selectivity, such that the yield of the desired olefin is maximized, and extraneous oxidative side reactions are minimized.

The disclosed invention provides a solution to these problems. In at least one embodiment of the invention, the conversion of one or more hydrocarbons to one or more unsaturated hydrocarbons may be achieved with relatively high selectivities to the desired product as a result of conducting the process in a microchannel reactor without the use of catalyst.

SUMMARY

The invention relates to a process for converting a feed composition comprising one or more hydrocarbons to a product comprising one or more unsaturated hydrocarbons, the process comprising: flowing the feed composition and steam in contact with each other in a microchannel reactor at a temperature in the range from about 200° C. to about 1200° C. to convert the feed composition to the product, the process being characterized by the absence of catalyst for converting the one or more hydrocarbons to one or more unsaturated hydrocarbons. Hydrogen and/or oxygen or a source of oxygen may be combined with the feed composition and steam.

In one embodiment, the process may comprise a cracking process wherein one or more C—C bonds in one or more of the hydrocarbons in the feed composition are ruptured to yield a product comprising one or more hydrocarbons having a lower molecular weight than the one or more hydrocarbons in the feed composition, one or more of the hydrocarbons in the product being the one or more unsaturated hydrocarbons.

In one embodiment, the process may comprise a dehydrogenation process wherein one or more C—H bonds in one or more of the hydrocarbons in the feed composition are ruptured to yield hydrogen and the one or more unsaturated hydrocarbons in the product.

In one embodiment, the invention relates to a process for converting a feed composition comprising ethane to a product comprising ethylene, the process comprising: flowing the feed composition and steam in contact with each other in a microchannel reactor at a temperature in the range from about 700° C. to about 1100° C. to convert the feed composition to the product, the process being characterized by the absence of catalyst for converting ethane to ethylene.

BRIEF DESCRIPTION OF THE DRAWINGS

In the annexed drawings, like parts and features have like designations. A number of the drawings provided herein are schematic illustrations which may not be drawn to scale or proportioned accurately.

FIGS. 2-7 and 15-22 are schematic illustrations of microchannel reactors that may be used in accordance with the inventive process.

FIGS. 8-14 and 23-24 are schematic illustrations of repeating units that may be used in the microchannel reactors.

DETAILED DESCRIPTION

Figure 1:
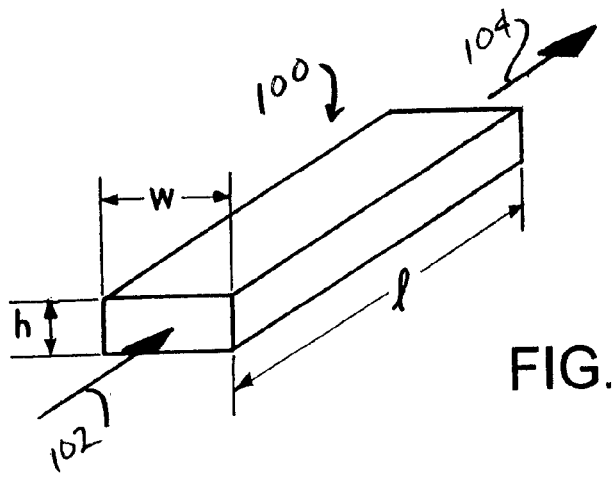
FIG. 1 is a schematic illustration of a process microchannel that may be used with the inventive process.

The term "microchannel" may refer to a channel having at least one internal dimension of height or width of up to about 10 millimeters (mm), and in one embodiment up to about 5 mm, and in one embodiment up to about 2 mm, and in one embodiment up to about 1 mm. The microchannel may comprise at least one inlet and at least one outlet wherein the at least one inlet is distinct from the at least one outlet. The microchannel may not be merely an orifice. The microchannel may not be merely a channel through a zeolite or a mesoporous material. An example of a microchannel that may be used with the inventive process is illustrated in FIG. 1. Referring to FIG. 1, microchannel 100 has a height (h), width (w) and length (l). Fluid may flow through the microchannel in the direction indicated by the arrows 102 and 104. The direction indicated by arrows 102 and 104 may be referred to as the bulk flow direction. Both the height (h) and width (w) are perpendicular to the bulk flow direction. The length (l) may be at least about two times the height (h) or width (w), and in one embodiment at least about five times the height (h) or width (w), and in one embodiment at least about ten times the height (h) or width (w). The height (h) or width (w) of the microchannel may be in the range from about 0.05 to about 10 mm, and in one embodiment from about 0.05 to about 5 mm, and in one embodiment from about 0.05 to about 2 mm, and in one embodiment from about 0.05 to about 1.5 mm, and in one embodiment from about 0.05 to about 1 mm, and in one embodiment from about 0.05 to about 0.75 mm, and in one embodiment from about 0.05 to about 0.5 mm. The other dimension of height (h) or width (w) may be of any dimension, for example, up to about 3 meters, and in one embodiment about 0.01 to about 3 meters, and in one embodiment about 0.1 to about 3 meters. The length (l) of the microchannel may be of any dimension, for example, up to about 10 meters, and in one embodiment from about 0.1 to about 10 meters, and in one embodiment from about 0.2 to about 10 meters, and in one embodiment from about 0.2 to about 6 meters, and in one embodiment from 0.2 to about 3 meters. Although the microchannel illustrated in FIG. 1 has a cross section that is rectangular, it is to be understood that the microchannel may have a cross section having any shape, for example, a square, circle, semi-circle, trapezoid, etc. The shape and/or size of the cross section of the microchannel may vary over its length. For example, the height or width may taper from a relatively large dimension to a relatively small dimension, or vice versa, over the length of the microchannel.

The term "microchannel reactor" may refer to an apparatus comprising at least process microchannel, and in one embodiment a plurality of process microchannels, wherein a chemical reaction may be conducted or wherein a chemical conversion of at least one species may occur. The microchannel reactor may be used to conduct a steam cracking process or a dehydrogenation process. The process microchannels may be operated in parallel. The microchannel reactor may include one or more headers or manifold assemblies for providing for the flow of reactants into the process microchannels, and one or more footers or manifold assemblies providing for the flow of product out of the process microchannels. The microchannel reactor may further comprise one or more heat sources. The heat source may comprise one or more heat exchange channels adjacent to and/or in thermal contact with the process microchannels. The heat exchange channels may comprise one or more combustion channels which may be used in combination with one or more staged addition channels. The heat exchange channels (or combustion channels and staged addition channels) may be microchannels. The microchannel reactor may include one or more headers or manifolds providing for the flow of heat exchange fluid (or combustion fuel and oxygen or a source of oxygen) into the heat exchange channels, and one or more footers or manifold assemblies providing for the flow of heat exchange fluid (or combustion exhaust) out of the heat exchange channels.

The term "cracking process" may refer to a process wherein one or more C—C bonds in a hydrocarbon reactant are ruptured to yield a product comprising one or more hydrocarbon products having a lower molecular weight than the hydrocarbon reactant. One or more of the hydrocarbons in the product may be unsaturated. For example, a $C_{12}$ alkane may be converted to a $C_7$ alkane and a $C_5$ olefin.

The term "dehydrogenation process" may be used to refer to a process wherein one or more C—H bonds in a hydrocarbon are ruptured to yield hydrogen and one or more unsaturated hydrocarbons. For example, ethane may be converted to ethylene in a dehydrogenation process.

The term "process microchannel" may refer to a microchannel wherein a process is conducted. The process may relate to conducting a cracking process and/or a dehydrogenation process.

The term "volume" with respect to volume within a channel may include all volume in the channel a fluid may flow through or flow by. This volume may include volume within surface features that may be positioned in the channel and adapted for the flow of fluid in a flow-through manner or in a flow-by manner.

The term "adjacent" when referring to the position of one channel relative to the position of another channel may mean directly adjacent such that a wall or walls separate the two channels. In one embodiment, the two channels may have a common wall. The common wall may vary in thickness. However, "adjacent" channels may not be separated by an intervening channel that may interfere with heat transfer between the channels. One channel may be adjacent to another channel over only part of the dimension of the another channel. For example, a process microchannel may be longer than and extend beyond one or more adjacent heat exchange channels.

The term "thermal contact" may refer to two bodies, for example, two channels, that may or may not be in physical contact with each other or adjacent to each other but still exchange heat with each other. One body in thermal contact with another body may heat or cool the other body.

The term "fluid" may refer to a gas, a liquid, a mixture of a gas and a liquid, or a gas or a liquid containing dispersed solids, liquid droplets and/or gaseous bubbles. The droplets and/or bubbles may be irregularly or regularly shaped and may be of similar or different sizes.

The terms "gas" and "vapor" may have the same meaning and are sometimes used interchangeably.

The term "contact time" may refer to the volume of a reaction zone within a microchannel divided by the volumetric feed flow rate of the reactants at a temperature of 0° C. and a pressure of one atmosphere.

The term "residence time" or "average residence time" may refer to the internal volume of a space within a channel occupied by a fluid flowing in the space divided by the average volumetric flow rate for the fluid flowing in the space at the temperature and pressure being used.

The terms "upstream" and "downstream" may refer to positions within a channel (e.g., a process microchannel) that is relative to the direction of flow of a fluid in the channel. For example, a position within a channel not yet reached by a portion of a fluid stream flowing toward that position would be downstream of that portion of the fluid stream. A position within the channel already passed by a portion of a fluid stream flowing away from that position would be upstream of that portion of the fluid stream. The terms "upstream" and "downstream" do not necessarily refer to a vertical position since the channels used herein may be oriented horizontally, vertically or at an inclined angle.

The term "shim" may refer to a planar or substantially planar sheet or plate. The thickness of the shim may be the smallest dimension of the shim and may be up to about 4 mm, and in one embodiment in the range from about 0.05 to about 2 mm, and in one embodiment in the range of about 0.05 to about 1 mm, and in one embodiment in the range from about 0.05 to about 0.5 mm. The shim may have any length and width.

Figure 25:
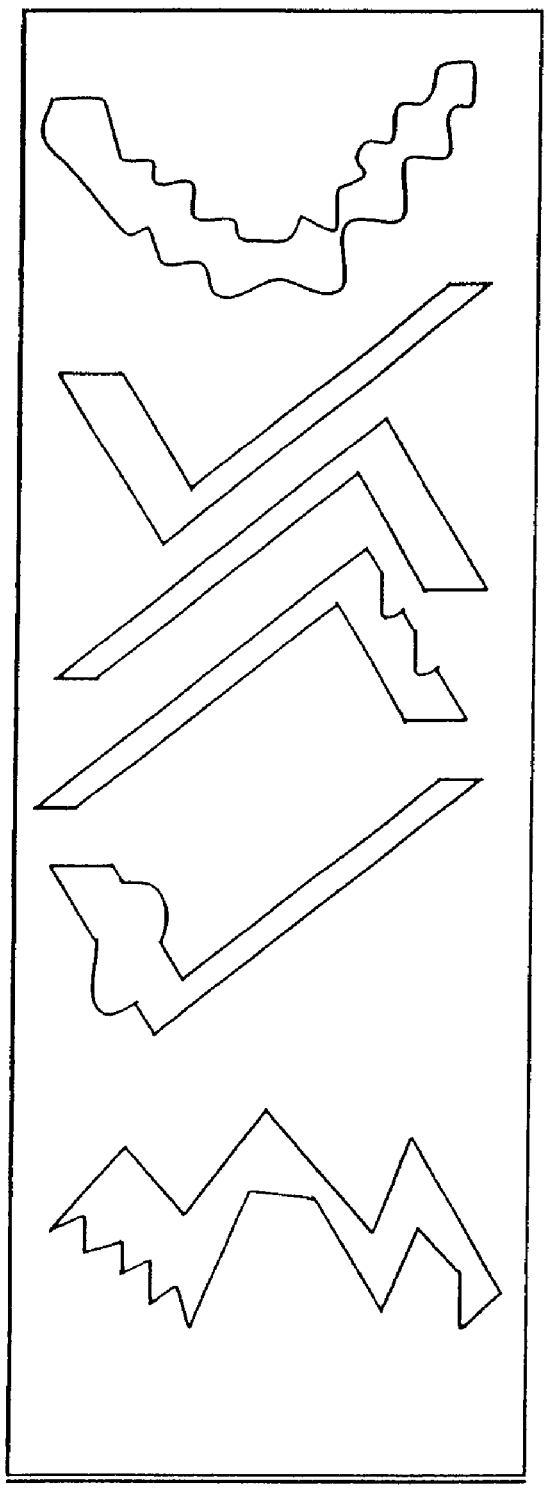
FIGS. 25 and 26 are schematic illustrations of surface features that may be used in channels in the microchannel reactors.
Figure 26:
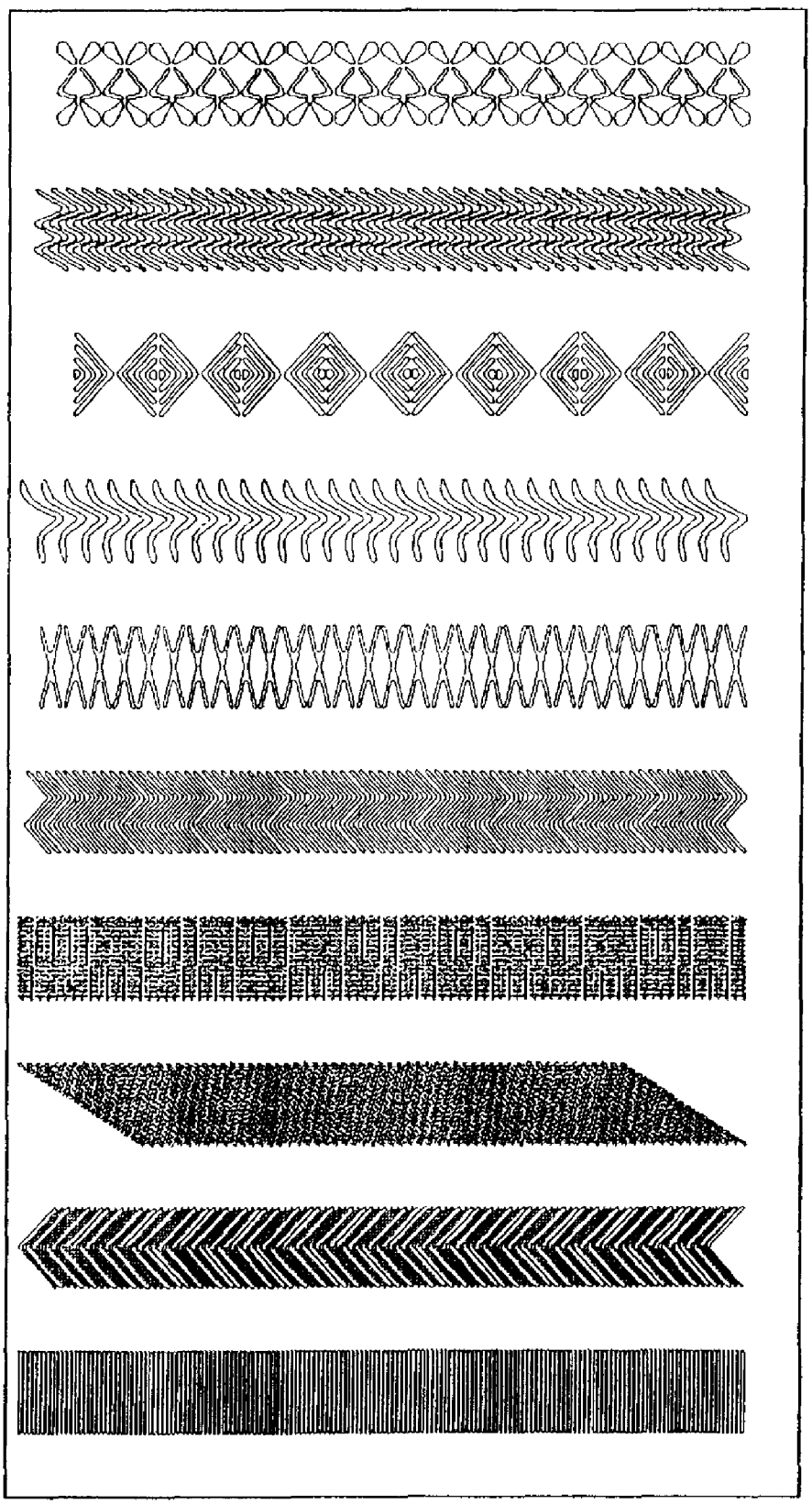

The term "surface feature" may refer to a depression in a channel wall and/or a projection from a channel wall that disrupts flow within the channel. Examples of surface feature designs that may be used are illustrated in FIGS. 25 and 26. The surface features may be in the form of circles, spheres, frustrums, oblongs, squares, rectangles, angled rectangles, checks, chevrons, vanes, air foils, wavy shapes, and the like. Combinations of two or more of the foregoing surface features may be used. The surface features may contain subfeatures where the major walls of the surface features further contain smaller surface features that may take the form of notches, waves, indents, holes, burrs, checks, scallops, and the like. The surface features may have a depth, a width, and a length. The surface features may be formed on or in one or more of the interior walls of the process microchannels, heat exchange channels (or combustion channels) used in accordance with the inventive process. The surface features may be referred to as passive surface features or passive mixing features. The surface features may be used to disrupt flow (for example, disrupt laminar flow streamlines) and create advective flow at an angle to the bulk flow direction.

The term "heat source" may refer to a substance or device that gives off heat and may be used to heat another substance or device. The heat source may be in the form of a heat exchange channel having a heat exchange fluid in it that transfers heat to another substance or device; the another substance or device being, for example, a channel that is adjacent to and/or in thermal contact with the heat exchange channel. The heat exchange fluid may be in the heat exchange channel. The heat exchange fluid may flow in the heat exchange channel. The heat exchange channel may be in the form of a combustion channel which may be used in combination with one or more staged addition channels. The heat exchange fluid may be in the form of a fuel that in combination with oxygen or a source of oxygen undergoes combustion in a combustion channel to generate heat and form a combustion exhaust. The heat source may be in the form of a non-fluid heating element, for example, an electric heating element or a resistance heater.

The term "heat exchange channel" may refer to a channel having a heat exchange fluid in it that provides heat and/or absorbs heat. The heat exchange channels may comprise one or more combustion channels which may be used in combination with one or more adjacent staged addition channels. The heat exchange channel (or combustion channel and staged addition channel) may be a microchannel. The heat exchange channel may absorb heat from or provide heat to an adjacent channel (e.g., process microchannel) and/or one or more channels in thermal contact with the heat exchange channel. The heat exchange channel may absorb heat from or provide heat to channels that are adjacent to each other but not adjacent to the heat exchange channel. In one embodiment, the heat exchange channel may exchange heat with one, two, three or more channels that may be adjacent to each other wherein one of the channels is positioned adjacent to the heat exchange channel while the other channels are not adjacent to the heat exchange channel but are in thermal contact with the heat exchange channel.

The term "heat transfer wall" may refer to a common wall between a process microchannel and an adjacent heat exchange channel where heat transfers from one channel to the other through the common wall.

The term "heat exchange fluid" may refer to a fluid that may give off heat and/or absorb heat.

The term "bulk flow direction" may refer to the vector through which fluid may travel in an open path in a channel.

The term "bulk flow region" may refer to open areas within a channel. A contiguous bulk flow region may allow rapid fluid flow through a channel without significant pressure drops. In one embodiment, the flow in the bulk flow region may be laminar. A bulk flow region may comprise at least about 5% of the internal volume and/or cross-sectional area of a channel (e.g., microchannel), and in one embodiment from about 5% to about 100%, and in one embodiment from about 5% to about 99%, and in one embodiment about 5% to about 95%, and in one embodiment from about 5% to about 90%, and in one embodiment from about 30% to about 80% of the internal volume and/or cross-sectional area of the channel.

The terms "open channel" or "flow-by channel" or "open path" may refer to a channel (e.g., a microchannel) with a gap of at least about 0.01 mm that extends all the way through the channel such that fluid may flow through the channel without encountering a barrier to flow. The gap may extend up to about 10 mm.

The term "cross-sectional area" of a channel (e.g., process microchannel) may refer to an area measured perpendicular to the direction of the bulk flow of fluid in the channel and may include all areas within the channel including any surface features that may be present, but does not include the channel walls. For channels that curve along their length, the cross-sectional area may be measured perpendicular to the direction of bulk flow at a selected point along a line that parallels the length and is at the center (by area) of the channel. Dimensions of height and width may be measured from one channel wall to the opposite channel wall. These dimensions may not be changed by application of a coating to the surface of the wall. These dimensions may be average values that account for variations caused by surface features, surface roughness, and the like.

The term "open cross-sectional area" of a channel (e.g., process microchannel) may refer to an area open for bulk fluid flow in a channel measured perpendicular to the direction of the bulk flow of fluid flow in the channel. The open cross-sectional area may not include internal obstructions such as surface features and the like which may be present.

The term "superficial velocity" for the velocity of a fluid flowing in a channel may refer to the velocity resulting from dividing the volumetric flow rate of the fluid at the inlet temperature and pressure of the channel divided by the cross-sectional area of the channel.

The term "free stream velocity" may refer to the velocity of a stream flowing in a channel at a sufficient distance from the sidewall of the channel such that the velocity is at a maximum value. The velocity of a stream flowing in a channel is zero at the sidewall if a no slip boundary condition is applicable, but increases as the distance from the sidewall increases until a constant value is achieved. This constant value is the "free stream velocity."

The term "process fluid" may be used herein to refer to reactants, product and any diluent or other fluid that may flow in a process microchannel.

The term "reaction zone" may refer to the space within a channel wherein a chemical reaction may occur or wherein a chemical conversion of at least one species may occur.

The term "yield" may refer to the number of moles of product exiting a microchannel reactor divided by the number of moles of a reactant entering the microchannel reactor.

The term "cycle" may refer to a single pass of the reactants through a microchannel reactor.

The term "hydrocarbon" may refer to purely hydrocarbon compounds; that is, aliphatic compounds, (e.g., alkane, alkene or alkyne), alicyclic compounds (e.g., cycloalkane, cycloalkylene), aromatic compounds, aliphatic- and alicyclic-substituted aromatic compounds, aromatic-substituted aliphatic compounds, aromatic-substituted alicyclic compounds, and the like. Examples may include methane, ethane, propane, cyclohexane, ethyl cyclohexane, toluene, ethyl benzene, etc. The term "hydrocarbon" may refer to substituted hydrocarbon compounds; that is, hydrocarbon compounds containing non-hydrocarbon substituents. Examples of the non-hydrocarbon substituents may include hydroxyl, acyl, nitro, etc. The term "hydrocarbon" may refer to hetero substituted hydrocarbon compounds; that is, hydrocarbon compounds which contain atoms other than carbon in a chain or ring otherwise containing carbon atoms. The hetero atoms may include, for example, nitrogen, oxygen, sulfur, and the like.

The term "characterized by the absence of catalyst for converting the one or more hydrocarbons to one or more unsaturated hydrocarbons" may refer to the fact that with the inventive process the feed composition comprising one or more hydrocarbons is converted to a product comprising one or more unsaturated hydrocarbons without employing the use of a catalyst to catalyze the conversion. It is to be understood, however, that the process microchannels may comprise one or more materials that may function as catalysts, for example, for reactions other than the conversion of one or more hydrocarbons to one or more unsaturated hydrocarbons, provided such materials do not increase the conversion of the one or more hydrocarbons to the one or more unsaturated hydrocarbons, or increase the foregoing conversion by no more than about 10% of what the conversion would be if such materials were not present, and in one embodiment by no more than about 7%, and in one embodiment by no more than about 5%, and in one embodiment by no more than about 3%, and in one embodiment by no more than about 2%, and in one embodiment by no more than about 1%, and in one embodiment by no more than about 0.5%, and in one embodiment by no more than about 0.1%. Thus, for example, if such a material was present and the conversion was 62%, but without the material being present the conversion would be 60%, the reaction would be "characterized by the absence of catalyst for converting the one or more hydrocarbons to one or more unsaturated hydrocarbon" since the catalyst increased conversion by only 3.33% ((62%−60%)/60%=3.33%) which would be within the range of no more than about 10%. Also, a catalyst or catalyst-like material, for example, a noble metal (e.g., Au, Ag, Pt, Pd, Ir, Rh, Hg, Ru, and/or Os), that does not increase the conversion of the one or more hydrocarbons to one or more unsaturated hydrocarbons, or increases the conversion of the one or more hydrocarbons to the one or more unsaturated hydrocarbons by no more than about 10% of what the conversion would be if such catalyst or catalyst-like material were not present, and in one embodiment by no more than about 7%, and in one embodiment by no more than about 5%, and in one embodiment by no more than about 3%, and in one embodiment by no more than about 2%, and in one embodiment by no more than about 1%, and in one embodiment by no more than about 0.5%, and in one embodiment by no more than about 0.1%, but inhibits the formation of one or more unwanted secondary products, may be provided in the process microchannels. It is also to be understood that catalysts may be used in other parts of the inventive process. For example, in one embodiment of the invention, a combustion channel may be used as a heat source and a combustion catalyst may be used in the combustion channel to catalyze the combustion reaction.

The term "graded catalyst" may refer to a catalyst with one or more gradients of catalytic activity. A graded catalyst may be used in the combustion channels discussed below. A graded catalyst may be used to inhibit the formation of one or more unwanted secondary products as discussed above. The graded catalyst may have a varying concentration or surface area of a catalytically active metal. The graded catalyst may have a varying turnover rate of catalytically active sites. The graded catalyst may have physical properties and/or a form that varies as a function of distance. For example, the graded catalyst may have an active metal concentration that is relatively low at the entrance to a channel and increases to a higher concentration near the exit of the channel, or vice versa; or a lower concentration of catalytically active metal nearer the center (i.e., midpoint) of a channel and a higher concentration nearer a channel wall, or vice versa, etc. The thermal conductivity of a graded catalyst may vary from one location to another within a channel. The surface area of a graded catalyst may be varied by varying the size of catalytically active metal sites on a constant surface area support, or by varying the surface area of the support such as by varying support type or particle size. A graded catalyst may have a porous support where the surface area to volume ratio of the support is higher or lower in different parts of the channel followed by the application of the same catalyst coating everywhere. A combination of two or more of the preceding embodiments may be used. The graded catalyst may have a single catalytic component or multiple catalytic components (for example, a bimetallic or trimetallic catalyst). The graded catalyst may change its properties and/or composition gradually as a function of distance from one location to another within a channel. The graded catalyst may comprise rimmed particles that have "eggshell" distributions of catalytically active metal within each particle. The graded catalyst may be graded in the axial direction along the length of a channel or in the lateral direction. The graded catalyst may have different catalyst compositions, different loadings and/or numbers of active catalytic sites that may vary from one position to another position within a channel. The number of catalytically active sites may be changed by altering the porosity of the catalyst structure. This may be accomplished using a washcoating process that deposits varying amounts of catalytic material. An example may be the use of different porous catalyst thicknesses along the channel length, whereby a thicker porous structure may be left where more activity is required. A change in porosity for a fixed or variable porous catalyst thickness may also be used. A first pore size may be used adjacent to an open area or gap for flow and at least one second pore size may be used adjacent to the process microchannel wall.

The term "mm" may refer to millimeter. The term "nm" may refer to nanometer. The term "ms" may refer to millisecond. The term "μs" may refer to microsecond. The term "μm" may refer to micron or micrometer. The terms "micron" and "micrometer" have the same meaning and may be used interchangeably. The term m/s may refer to meters per second.

Unless otherwise indicated, all pressures are expressed in terms of absolute pressure.

The hydrocarbons that may be used in the feed composition may comprise any hydrocarbon that may be converted to an unsaturated hydrocarbon. These may include hydrocarbons that contain one or more C—C bonds capable of being ruptured in a cracking process and/or one or more C—H bonds capable of being ruptured in a dehydrogenation process. The hydrocarbons that may be used in the feed composition may include saturated aliphatic compounds (e.g., alkanes), unsaturated aliphatic compounds (e.g., alkenes, alkynes), hydrocarbyl (e.g., alkyl) substituted aromatic compounds, hydrocarbylene (e.g., alkylene) substituted aromatic compounds, and the like. The hydrocarbons that may be used in the inventive process may be unsaturated hydrocarbons wherein the unsaturated hydrocarbons undergo further unsaturation. For example, a monoene may be converted to a diene or a polyene (e.g., butylene may be converted to butadiene).

The saturated aliphatic compounds may include alkanes containing 2 to about 25 carbon atoms per molecule, and in one embodiment 2 to about 20 carbon atoms, and in one embodiment 2 to about 10 carbon atoms. These may include straight chain alkanes, single and multiple branched chain alkanes, and cyclic alkanes including cyclic alkanes having one or more alkyl groups attached to the ring. These may include ethane, propane, isopropane, butane, isobutane, pentane, cyclopentane, hexane, cyclohexane, heptane, octane, 2-ethylhexane, nonane, decane, dodecane, or a mixture of two or more thereof, and the like.

The unsaturated aliphatic compounds may include alkenes or alkylenes, and alkynes. The unsaturated aliphatic compounds may contain from 3 to about 25 carbon atoms, and in one embodiment from about 3 to about 20 carbon atoms, and in one embodiment from about 3 to about 10 carbon atoms. These may include straight chain alkenes, single and multiple branched chain alkenes, and cyclic alkenes including cyclic alkenes having one or more alkyl and/or alkene groups attached to the ring. The unsaturated hydrocarbons may include propylene; 1-butene; 2-butene; isobutlene; 1-pentene; 2-pentene; 3-methyl-1-butene; 2-methyl-2-butene; 1-hexene; 2,3-dimethyl-2-butene; 1-heptene; 1-octene; 1-nonene; 1-decene; 1-dodecene; and the like.

The unsaturated aliphatic compounds that may be included in the feed composition may comprise polyenes. These may include dienes, trienes, and the like. These compounds may contain from 3 to about 25 carbon atoms per molecule, and in one embodiment from 4 to about 20 carbon atoms, and in one embodiment from about 4 to about 10 carbon atoms. Examples may include 1,2-propadiene (also known as allene); 1,3-butadiene; 2-methyl-1,3-butadiene (also known as isoprene); 1,3-pentadiene; 1,4-pentadiene; 1,5-hexadiene; 2,4-hexadiene; 2,3-dimethyl-1,3-butadiene; and the like.

The hydrocarbyl (e.g., alkyl) and hydrocarbylene (e.g., alkylene) substituted aromatic compounds that may be included in the feed composition may contain one or more hydrocarbyl or hydrocarbylene substituents. These compounds may be monocyclic (e.g., phenyl) or polycyclic (e.g., naphthyl). These compounds may include alkyl substituted aromatic compounds containing one or more alkyl groups of 2 to about 25 carbon atoms, and in one embodiment 2 to about 20 carbon atoms, and in one embodiment 2 to about 10 carbon atoms. These may also include akylene substituted aromatic compounds containing one or more alkylene groups of 3 to about 25 carbon atoms, and in one embodiment 3 to about 20 carbon atoms, and in one embodiment 3 to about 10 carbon atoms. Examples may include ethylbenzene, n-propylbenzene, n-butylbenzene, isobutylbenzene, sec-butylbenzene, tert-butylbenzene, and the like.

The feed composition may comprise any hydrocarbon oil capable of undergoing cracking or dehydrogenation. These may vary from naptha to heavy crude oil residual fractions. The feed composition may have a 5% by volume boiling point above about 175° C., and in one embodiment above about 205° C. In one embodiment, at least about 90% by volume of the feed composition may fall within the boiling point range of about 150° C. to about 570° C., and in one embodiment from about 320° C. to about 540° C. The feed composition may comprise one or more petroleum fractions such as atmospheric and vacuum gas oils (AGO and VGO). The feed composition may comprise one or more mineral or synthetic oils, or a mixture of one or more fractions thereof. The feed composition may comprise one or more straight run gas oils, vacuum gas oils, demetallized oils, deasphalted vacuum residues, coker distillates, cat cracker distillates, shale oil, tar sand oil, coal liquids, or a mixture of two or more thereof, and the like.

The feed composition may include one or more diluent materials. Examples of such diluents may include non-reactive hydrocarbon diluents, and the like. The diluent concentration may be in the range from zero to about 99% by weight based on the weight of the hydrocarbon reactant, and in one embodiment from zero to about 75% by weight, and in one embodiment from zero to about 50% by weight. The diluents may be used to reduce the viscosity of viscous liquid reactants. An advantage of at least one embodiment of the invention may be that when the use of such diluents is avoided, operation of the inventive process may be more efficient and compact.

The viscosity of the feed composition may be in the range from about 0.001 to about 1 centipoise, and in one embodiment from about 0.01 to about 1 centipoise, and in one embodiment from about 0.1 to about 1 centipoise.

The steam used for contacting the feed composition may be at a temperature in the range from about 100 to about 1100° C., and in one embodiment from about 120° C. to about 1100° C., and in one embodiment from about 120° C. to about 1000° C., and in one embodiment from about 120° C. to about 900° C., and in one embodiment in the range from about 200 to about 900° C. The steam may be at a pressure in the range from about 1 to about 100 atmospheres (absolute pressure), and in one embodiment in the range from about 1 to about 20 atmospheres, and in one embodiment from 1 to about 5 atmospheres. The mole ratio of hydrocarbon reactant in the feed composition to steam may be in the range from about 0.1 to about 10, and in one embodiment from about 0.5 to about 4.

The oxygen or oxygen source, when used, may comprise molecular oxygen ($O_2$), air, oxygen enriched air, or other oxidants, such as nitrogen oxides, which may function as a source of oxygen. The oxygen source may comprise carbon dioxide, carbon monoxide or a peroxide (e.g., hydrogen peroxide). Gaseous mixtures containing oxygen, such as mixtures of oxygen and air, or mixtures of oxygen and an inert gas (e.g., helium, argon, etc.) or a diluent gas (e.g., carbon dioxide, water vapor, etc.) may be used. The mole ratio of the hydrocarbon reactant in the feed composition to oxygen, when used, may be in the range up to about 10, and in one embodiment from about 0.1 to about 10, and in one embodiment from about 0.1 to about 5, and in one embodiment from about 0.2 to about 4.

The hydrogen, when used, may comprise molecular hydrogen ($H_2$). The hydrogen may be mixed with an inert gas (e.g., helium, argon, etc.) or a diluent gas (e.g., carbon dioxide, carbon monoxide, water vapor, etc.). The hydrogen may be derived from another process such as a steam reforming process (product stream with $H_2/CO$ mole ratio of about 3), a partial oxidation process (product stream with $H_2/CO$ mole ration of about 2), an autothermal reforming process (product stream with $H_2/CO$ mole ratio of about 2.5), a $CO_2$ reforming process (product stream with $H_2/CO$ mole ratio of about 1), a coal gassification process (product stream with $H_2/CO$ mole ratio of about 1), or a combination of two or more thereof. With each of these feed streams the hydrogen may be separated from the remaining ingredients using conventional techniques such as membranes or adsorption. The mole ratio of hydrocarbon reactant in the feed composition to hydrogen, when used, may be in the range up to about 10, and in one embodiment from about 0.1 to about 10, and in one embodiment from about 0.2 to about 8.

The product may comprise one or more monoenes, one or more dienes, one or more polyenes, or a mixture of two or more thereof. The product may comprise one or more unsaturated aliphatic compounds. These may include alkenes or alkylenes, and alkynes. The unsaturated aliphatic compounds may contain from 2 to about 25 carbon atoms, and in one embodiment from 2 to about 20 carbon atoms, and in one embodiment from 2 to about 10 carbon atoms. These may include straight chain alkenes, single and multiple branched chain alkenes, and cyclic alkenes including cyclic alkenes having one or more alkyl and/or alkene groups attached to the ring. The unsaturated hydrocarbons may include ethylene; propylene; 1-butene; 2-butene; isobutlene; 1-pentene; 2-pentene; 3-methyl-1-butene; 2-methyl-2-butene; 1-hexene; 2,3-dimethyl-2-butene; 1-heptene; 1-octene; 1-nonene; 1-decene; 1-dodecene; mixtures of two or more thereof; and the like.

The product may comprise one or more polyenes. These may include dienes, trienes, and the like. These compounds may contain from 3 to about 25 carbon atoms per molecule, and in one embodiment from 4 to about 20 carbon atoms, and in one embodiment from about 4 to about 10 carbon atoms. Examples may include 1,2-propadiene (also known as allene); 1,3-butadiene; 2-methyl-1,3-butadiene (also known as isoprene); 1,3-pentadiene; 1,4-pentadiene; 1,5-hexadiene; 2,4-hexadiene; 2,3-dimethyl-1,3-butadiene; and the like.

The product may comprise a mixture of olefins and paraffins. The mole ratio of olefins to paraffins in the product may be in the range from about 0.01 to about 100, and in one embodiment in the range from 0.1 to about 10.

The product may comprise one or more hydrocarbylene (e.g., alkylene) substituted aromatic compounds. These may contain one or more alkylene substituents. These compounds may be monocyclic (e.g., phenyl) or polycyclic (e.g., naphthyl). These compounds may include alkylene substituted aromatic compounds containing one or more alkylene groups containing 2 to about 25 carbon atoms, and in one embodiment 2 to about 20 carbon atoms, and in one embodiment 2 to about 10 carbon atoms. Examples may include styrene, n-propylenebenzene, n-butylenebenzene, isobutylenebenzene, sec-butylenebenzene, tert-butylenebenzene, mixtures of two or more thereof, and the like.

The product may comprise a middle distillate fraction boiling in the range of about 125 to about 375° C. The term "middle distillate" is intended to include the diesel, jet fuel and kerosene boiling range fractions. The terms "kerosene" and "jet fuel" boiling range are intended to refer to a temperature range of about 260 to about 550° F. (127-288° C.) and "diesel" boiling range is intended to refer to hydrocarbon boiling points between about 260 to about 700° F. (127-371° C.). The product may comprise a gasoline or naphtha fraction. These may be considered to be the $C_5$ to about 205° C. endpoint fractions.

The unsaturated hydrocarbons or olefins in the product may be further processed to form alcohols, acids, esters, and the like, using microchannel processing or conventional (i.e., non-microchannel) processing.

Figure 2:
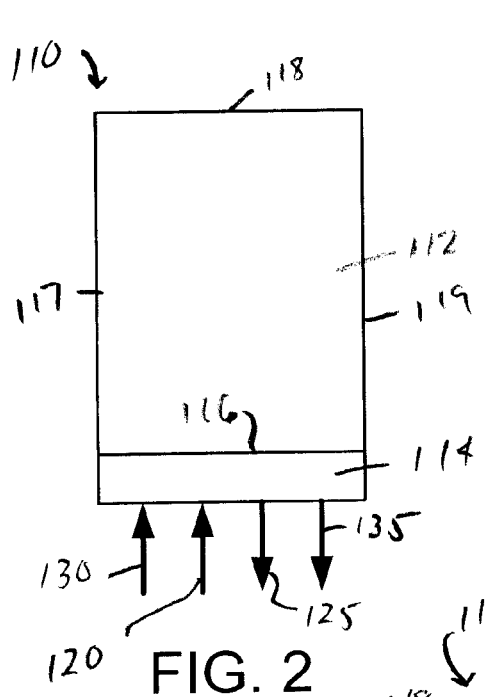

The inventive process will now be described with reference to the drawings. Referring to FIG. 2, the inventive process may be conducted using microchannel reactor 110. Microchannel reactor 110 includes microchannel reactor core 112 and manifold assembly 114. The microchannel reactor core 112 may have the shape of a cubic block that includes sides 116, 117, 118 and 119. Sides 116 and 118 are opposite each other as are sides 117 and 119. Sides 117 and 119 are orthogonal to sides 116 and 118. The microchannel reactor core 112 may contain a plurality of process microchannels and a plurality of heat exchange channels. The process microchannels and heat exchange channels may be aligned vertically, horizontally or at an inclined angle. In one embodiment, the process microchannels may be aligned vertically and the reactants may enter the process microchannels at the top of the channels and the product may exit at the bottom of the channels such that a downward flow pattern is established. The heat exchange channels may comprise combustion channels used in combination with one or more adjacent staged addition channels. The heat exchange channels (or combustion channels and staged addition channels) may be microchannels. The heat exchange channels (or combustion channels and staged addition channels) may be aligned with the process microchannels to provide for the flow of fluid in the heat exchange channels (or combustion channels and staged addition channels) that is cocurrent, counter-current and/or cross-current relative to the flow of fluid in the process microchannels.

The reactants, that is, the feed composition and steam (and, when used, hydrogen and/or oxygen or a source of oxygen) may enter the microchannel reactor 110 as indicated by arrow 120, flow through the manifold assembly 114 into the process microchannels in the microchannel reactor core 112, and undergo reaction to form the product. The product may flow out of the process microchannels into the manifold assembly 114, and then out of the microchannel reactor 110 as indicated by arrow 125.

Heat exchange fluid may enter the microchannel reactor 110 as indicated by arrow 130, flow through manifold assembly 114 into the heat exchange channels in the microchannel reactor core 112, transfer heat to the process microchannels, flow back into the manifold assembly 114 and then out of the microchannel reactor 110 as indicated by arrow 135.

When the heat exchange channels comprise combustion channels used in combination with staged addition channels, a fuel (e.g., hydrogen, natural gas, etc.) and oxygen or source of oxygen (e.g., air) may enter the microchannel reactor 110 as indicated by arrow 130. The fuel may flow through the manifold assembly 114 into the combustion channels. The oxygen or source of oxygen may flow through the manifold assembly 114 into the staged addition channels, and then from the staged addition channels into the combustion channels where it contacts the fuel. The fuel and oxygen or a source of oxygen may contact a combustion catalyst in the combustion channels and undergo a combustion reaction. The combustion reaction generates heat which is transferred to the process microchannels. The combustion reaction also generates a combustion exhaust. The combustion exhaust may flow out of the combustion channels into the manifold assembly 114 and then out of the microchannel reactor 110 as indicated by arrow 135.

In microchannel reactor 110, the reactants enter the microchannel reactor 110 on the same side, that is, side 116, from which the product exits the microchannel reactor 110. Similarly, the heat exchange fluid (or fuel and oxygen or source of oxygen) enters the microchannel reactor 110 on the same side of the microchannel reactor 110, that is, side 116, from which the heat exchange fluid (or combustion exhaust) exits the microchannel reactor 110.

Figure 3:
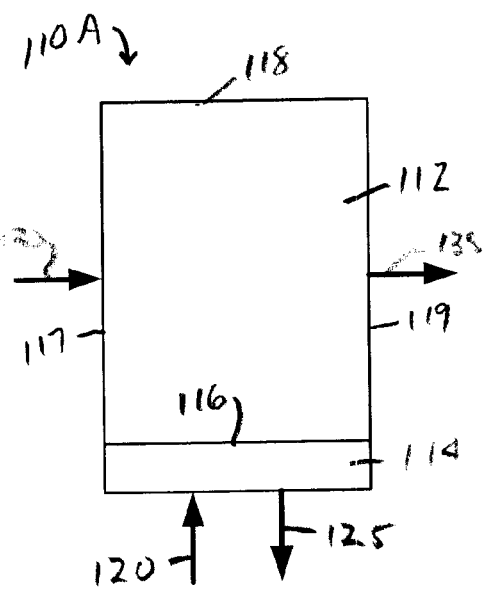

The microchannel reactor 110A illustrated in FIG. 3 is the same as the microchannel reactor 110 illustrated in FIG. 2 with the exception that the heat exchange fluid (or combustion fuel and oxygen or source of oxygen) enters the microchannel reactor core 112 through side 117 as indicated by arrow 130, and the heat exchange fluid (or combustion exhaust) exits the microchannel reactor core from side 119 as indicated by arrow 135. Heat exchange manifolds (not shown in the drawings) may be provided on sides 117 and 119 to provide for the flow of heat exchange fluid (or combustion fuel and oxygen or source of oxygen) into the heat exchange channels, and the flow of heat exchange fluid (or combustion exhaust) out of the heat exchange channels.

Figure 4:
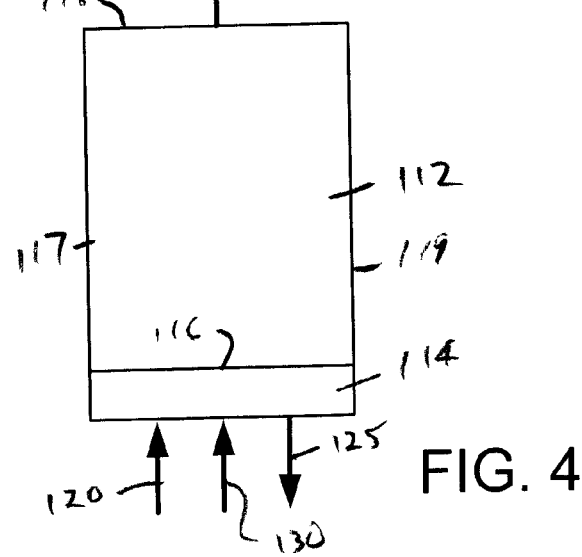

The microchannel reactor 110B illustrated in FIG. 4 is the same as the microchannel reactor 110 illustrated in FIG. 2 with the exception that the heat exchange fluid (or combustion fuel and oxygen or source of oxygen) enters the microchannel reactor core 112 through side 116 as indicated by arrow 130, and the heat exchange fluid (or combustion exhaust) exits the microchannel reactor core from side 118 as indicated by arrow 135. A heat exchange manifold (not shown in the drawings) may be provided on side 118 to provide for the flow of heat exchange fluid (or combustion exhaust) out of the heat exchange channels.

The microchannel reactor 110C illustrated in FIG. 5 is the same as the microchannel reactor 110 illustrated in FIG. 2 with the exception that the microchannel reactor 110C includes footer or manifold assembly 115. The reactants enter the microchannel reactor 110C through manifold assembly 114, flow through the process microchannels in the microchannel reactor core 112, and undergo reaction to form the product. The product exits the microchannel reactor core 112 through side 118, flows through manifold assembly 115 and out of the microchannel reactor 110C as indicated by arrow 125.

The microchannel reactor 110D illustrated in FIG. 6 is the same as the microchannel reactor 110C illustrated in FIG. 5 with the exception that the heat exchange fluid (or combustion fuel and oxygen or source of oxygen) enters the microchannel reactor core 112 through side 117 as indicated by arrow 130, and the heat exchange fluid (or combustion exhaust) exits the microchannel reactor core 112 through side 119 as indicated by arrow 135. Heat exchange manifolds (not shown in the drawings) may be provided on sides 117 and 119 to provide for the flow of heat exchange fluid (or combustion fuel and oxygen or source of oxygen) into the heat exchange channels, and the flow of heat exchange fluid (or combustion exhaust) out of the heat exchange channels.

The microchannel reactor 110E illustrated in FIG. 7 is the same as the microchannel reactor 110D illustrated in FIG. 6 with the exception that the heat exchange fluid (or combustion fuel and oxygen or source of oxygen) flows through manifold assembly 115 into the microchannel reactor core 112 as indicated by arrow 130, and the heat exchange fluid (or combustion exhaust) flows out of the microchannel reactor core 112 through manifold assembly 114 as indicated by arrow 135.

The microchannel reactor 110 may comprise a plurality of process microchannels, and a plurality of heat exchange channels (or combustion channels and staged addition channels). The microchannel reactor 110 may contain any desired number of process microchannels and heat exchange channels (or combustion channels and staged addition channels), for example, from about 100 to about 50,000 of each, and in one embodiment from about 1000 to about 10,000 of each. The process microchannels may be in the form of a U or an upside down U (see, FIGS. 12 and 13) wherein the reactants enter the process microchannels on one side of the microchannel reactor and product exits the process microchannels on the same side of the microchannel reactor. Alternatively, the process microchannels may be in the form of straight run channels (see, FIGS. 8-11 and 14) wherein the reactants enter the process microchannels on one side of the microchannel reactor and product exits the process microchannels on the other side of the microchannel reactor. The heat exchange channels may be aligned to provide for flow of heat exchange fluid that is co-current, counter-current and/or cross-current relative to the flow of fluid in the process microchannels (see, FIGS. 8 and 9). Two or more process microchannels may be used in combination with each heat exchange channel. For example, each heat exchange channel may be used in combination with two process microchannels wherein one of the process microchannels is adjacent to the heat exchange channel and the other process microchannel is adjacent to the first named process microchannel and in thermal contact with the heat exchange channel (see, FIG. 10).

Figure 13:
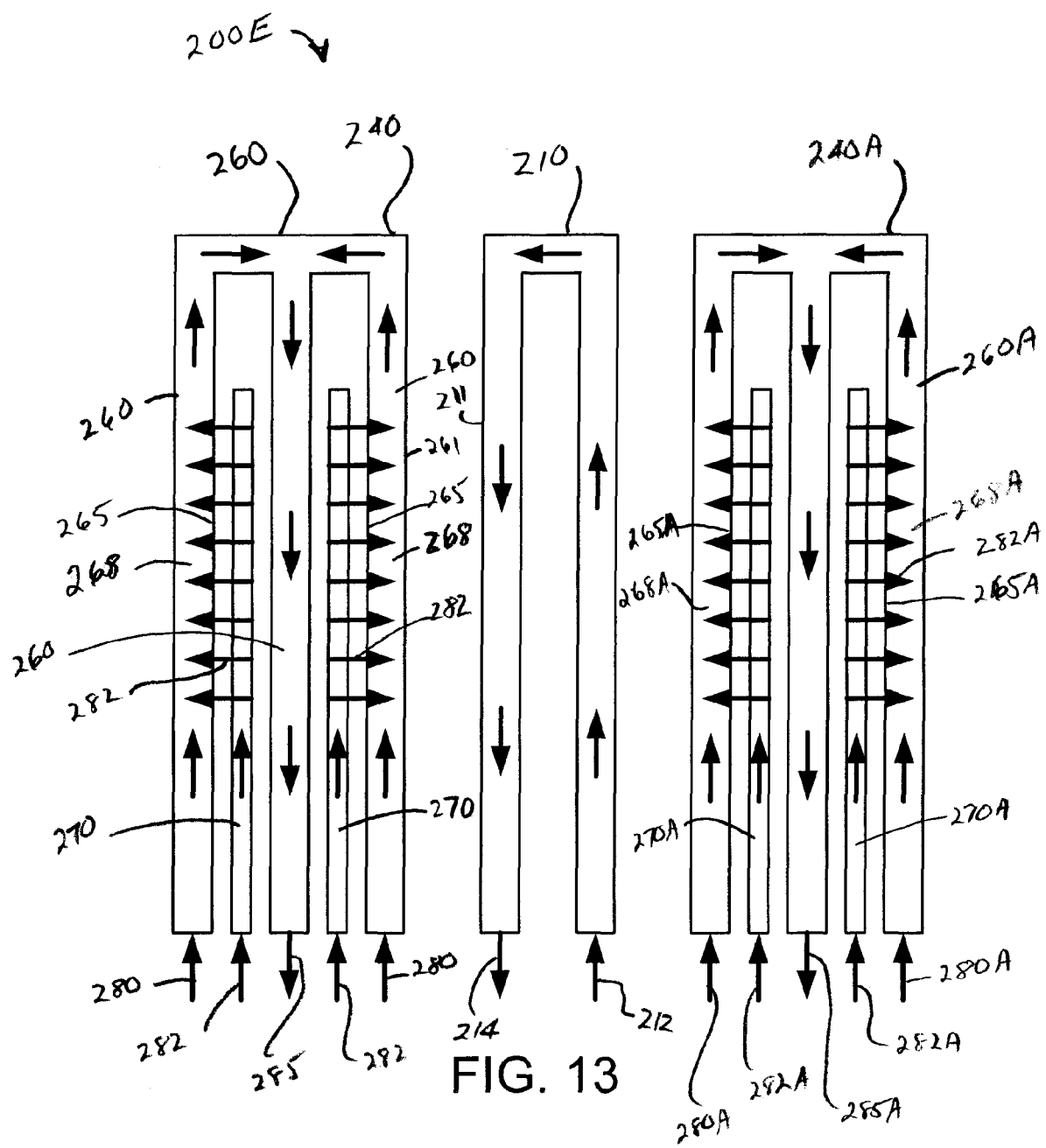
Figure 14:
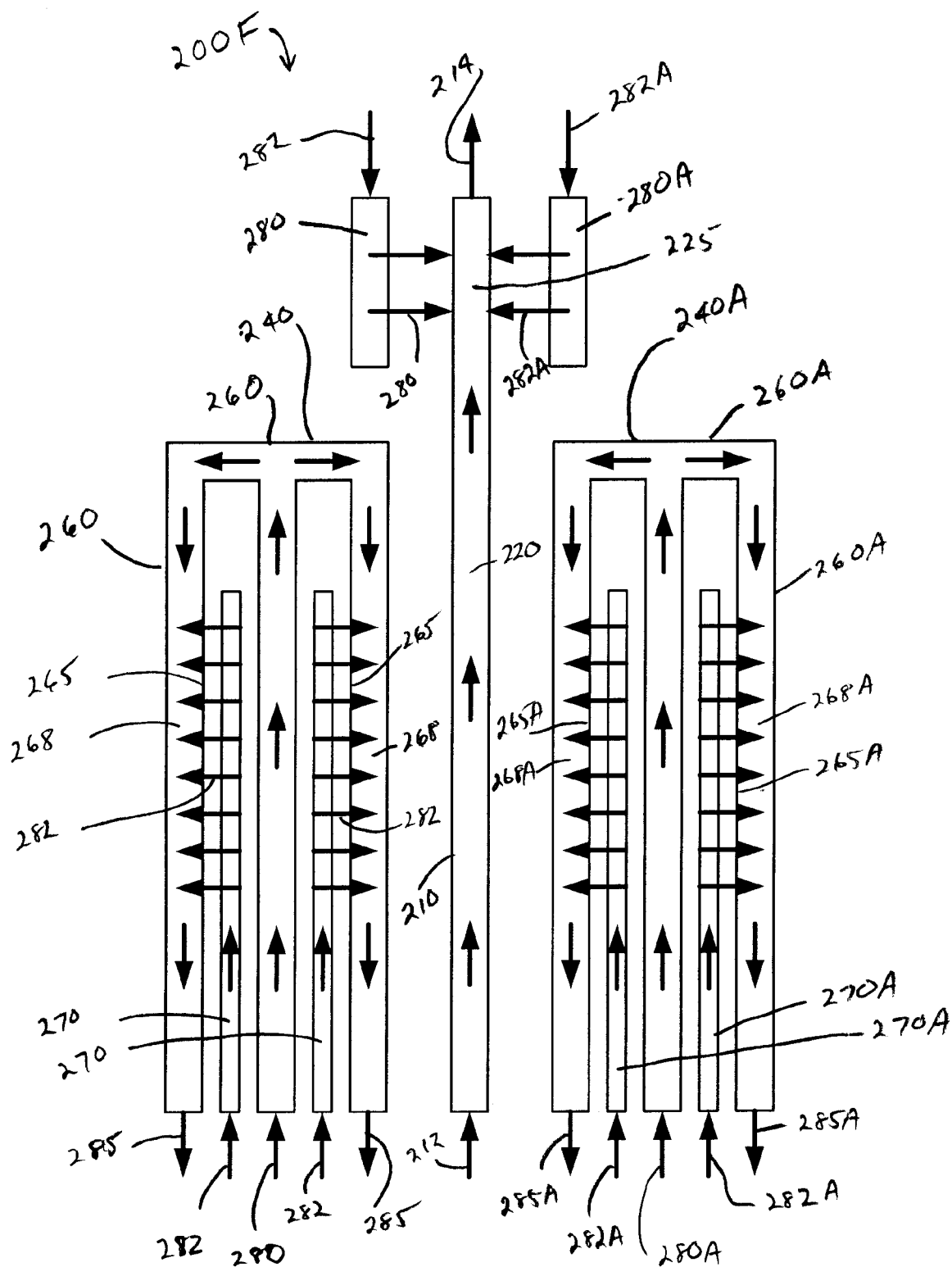

Each combustion channel may be adjacent to one or more staged addition channels (see, FIGS. 13 and 14). The combustion channels may contain one or more combustion catalysts. The staged addition channels may have different lengths than the combustion channels. The combustion channels and the staged addition channels may be microchannels. The combustion channels may be in the form of a U, an upside down U, a W or an M (see, FIGS. 13 and 14) wherein the fuel and oxygen or source of oxygen enter the combustion channel on one side of the microchannel reactor and the combustion exhaust exits on the same side. Alternatively, the combustion channels may be in the form of straight run channels wherein the fuel and oxygen or source of oxygen enter the microchannel reactor on one side of the reactor and the combustion exhaust exits on the other side of the microchannel reactor. The combustion channels may be aligned to provide for the flow of fluid in the combustion channels that is co-current, counter-current or cross-current relative to the flow of fluid in the process microchannels.

The microchannel reactor 110 may be equipped with appropriate headers and footers or manifolds to provide for the flow of reactants into the process microchannels, product out of the process microchannels, heat exchange fluid (or fuel and oxygen or a source of oxygen) into the heat exchange channels (or combustion channels and staged addition channels), and the flow of heat exchange fluid (or combustion exhaust) out of the heat exchange channels (or combustion channels).

The feed composition may be preheated to a temperature of at least about 120° C., and in one embodiment at least about 200° C., and in one embodiment at least about 300° C., and in one embodiment at least about 450° C., and in one embodiment at least about 600° C., and in one embodiment at least about 700° C., prior to entering the microchannel reactor 110. The feed composition may be preheated to a temperature of at least about 600° C., and in one embodiment at least about 700° C., and in one embodiment in the range from about 600 to about 1200° C., and in one embodiment from about 700 to about 1100° C. in the microchannel reactor 110.

In the microchannel reactor 110, the feed composition and steam (and optionally hydrogen and/or oxygen or source of oxygen) undergo reaction with the result being the formation of one or more of the above indicated products. The temperature within the microchannel reactor 110 may be in the range from about 200° C. to about 1200° C., and in one embodiment from about 400° C. to about 1200° C., and in one embodiment from about 500° C. to about 1200° C., and in one embodiment from about 500° C. to about 1100° C., and in one embodiment from about 600° C. to about 1100° C., and in one embodiment from about 700° C. to about 1100° C. The temperature may increase or decrease along the length of the process microchannels in order to enhance conversion, selectivity and/or the durability of the microchannel reactor. The pressure within the microchannel reactor 110 may be in the range from about 1 to about 100 atmospheres, and in one embodiment from about 1 to about 20 atmospheres, and in one embodiment from 1 to about 5 atmospheres. The conversion of hydrocarbon reactant in the microchannel reactor 110 may be in the range from about 1 to about 99%, and in one embodiment from about 60 to about 90%. The selectivity to unsaturated hydrocarbons may be in the range from about 10 to about 99%, and in one embodiment in the range from about 60 to about 90%. The reaction conducted in the microchannel reactor 110 is an endothermic reaction. This reaction may be referred to as a steam cracking reaction or a dehydrogenation reaction.

The product formed in the process microchannels may be quenched. The product may be quenched in the microchannel reactor 110 or outside of the microchannel reactor 110. The product may be quenched by reducing its temperature by at least about 200° C. within a period of up to about 1000 milliseconds (ms). The temperature may be reduced by about 200 to about 800° C., and in one embodiment by about 200 to about 600° C. within a period of about 1 to about 1000 ms, and in one embodiment from about 1 to about 500 ms. The quenching apparatus may be integral with the microchannel reactor, or it may be separate from the microchannel reactor.

The quenching apparatus may comprise a microchannel heat exchanger. The quenching apparatus may comprise a heat exchanger that is adjacent to or interleaved with the channel or conduit used for the product to exit the microchannel reactor 110. The quenching apparatus may comprise a mixer capable of rapidly mixing the product with a quenching fluid. The quenching fluid may be a low temperature steam or a condensable hydrocarbon injected as a liquid.

Alternatively, the quenching apparatus may comprise a narrow gap or passageway for the reactants to flow through. The gap or passageway may have a dimension equal to or below the quench diameter for the reaction. In this embodiment, the reaction may terminate as the reactants flow through the gap or passageway as a result of wall collisions. The gap or passageway may have a height or width of up to about 5 mm, and in one embodiment up to about 3 mm, and in one embodiment up to about 1 mm, and in one embodiment up to about 0.5 mm, and in one embodiment up to about 0.1 mm, and in one embodiment up to about 0.05 mm. The quenching apparatus may comprise a microchannel or a plurality of parallel microchannels. The quenching apparatus may comprise part of the process microchannels used with the inventive process downstream of the reaction zone within the process microchannels. The narrow gap or passageway may be used in conjunction with one or more of the other quenching apparatuses (e.g., heat exchangers) discussed above.

Figure 27:
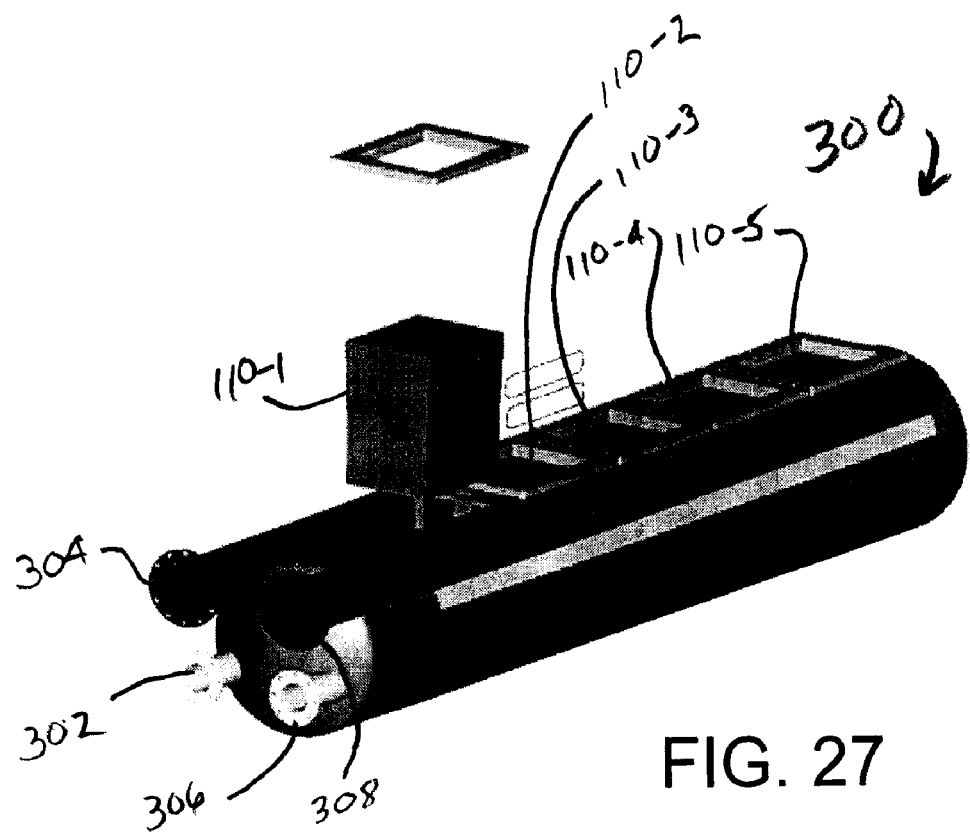
FIGS. 27-29 are illustrations of reaction vessels that may be used to house the microchannel reactors.
Figure 28:
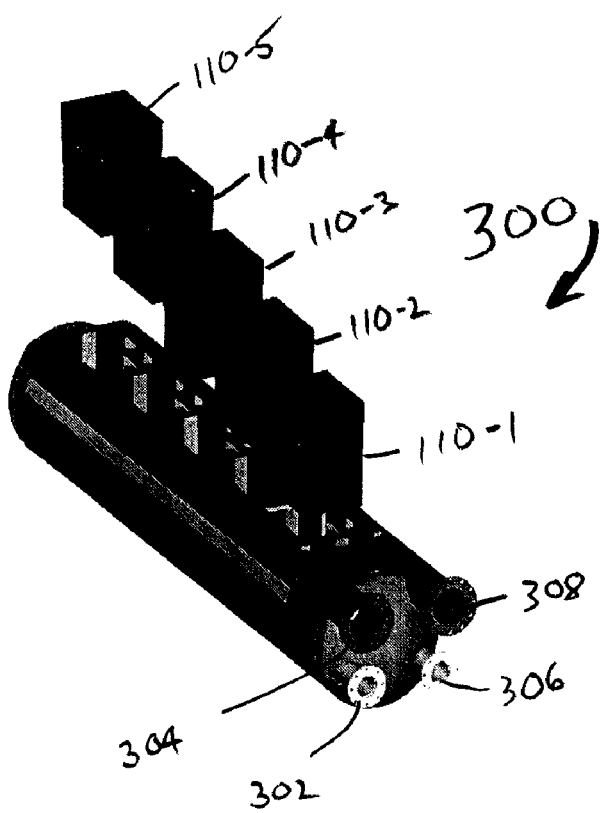

A plurality of the microchannel reactors 110 may be housed in reaction vessel 300 which is illustrated in FIGS. 27 and 28. Referring to FIGS. 27 and 28, the vessel 300 contains five microchannel reactors 110. These are identified in FIGS. 27 and 28 as microchannel reactors 110-1, 110-2, 110-3, 110-4 and 110-5. Although five microchannel reactors 110 are disclosed in the drawings (FIGS. 27 and 28), it will be understood that the vessel 300 may contain any desired number of microchannel reactors. For example, the vessel 300 may contain from 1 to about 1000 microchannel reactors 110, and in one embodiment from about 3 to about 500 microchannels reactors 110, and in one embodiment from about 3 to about 250 microchannel reactors 110, and in one embodiment from about 3 to about 150 microchannel reactors 110, and in one embodiment from about 5 to about 50 microchannel reactors 110, and in one embodiment from about 8 to about 12 microchannel reactors 110. In one embodiment, the vessel 300 may contain from 1 to about 50 microchannel reactors 110, and in one embodiment from 1 to about 20 microchannel reactors 110. The vessel 300 may be a pressurizable vessel. The vessel 300 includes inlets 302, 304 and 308, and outlet 306. The inlet 302 is connected to a manifold which is provided for flowing the reactants to the process microchannels in the microchannel reactors 110-1, 110-2, 110-3, 110-4 and 110-5. The inlet 304 is connected to a manifold which is provided for flowing the heat exchange fluid (or fuel) to the heat exchange channels (or combustion channels) in the microchannel reactors 110-1, 110-2, 110-3, 110-4 and 110-5. The outlet 306 is connected to a manifold which provides for the flow of product from the microchannel reactors 110-1, 110-2, 110-3, 110-4 and 110-5 out of the vessel 300. When the combustion channels and staged addition channels are used, the inlet 308 is connected to a manifold to provide for the flow of the oxygen or source of oxygen (e.g., air) to the staged addition channels in the microchannel reactors 110-1, 110-2, 110-3, 110-4 and 110-5. The vessel 300 also includes an outlet (not shown in the drawings) providing for the flow of heat exchange fluid (or exhaust gas) from the microchannel reactors 110-1, 110-2, 110-3, 110-4 and 110-5.

Figure 29:
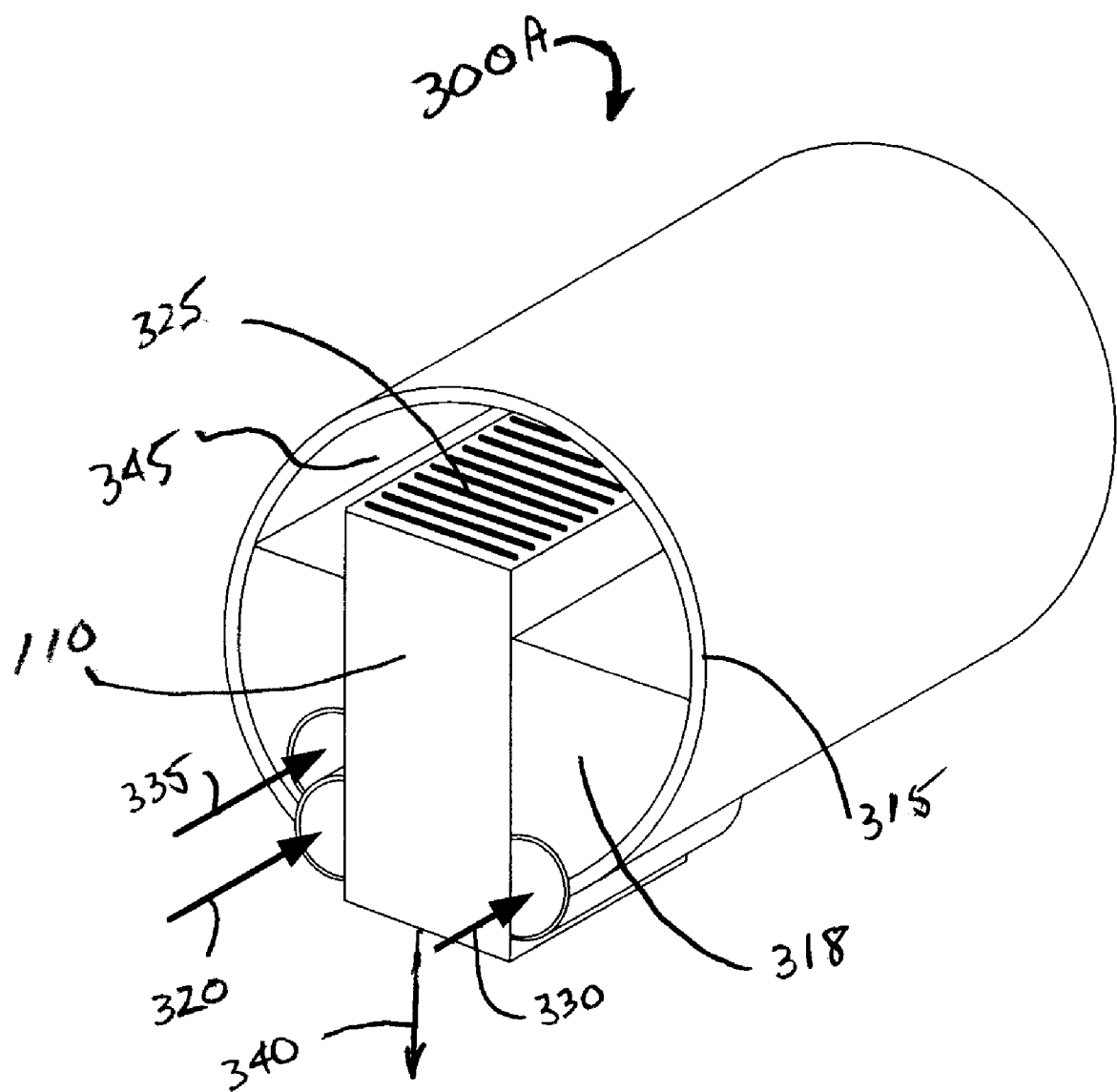
Figure 30:
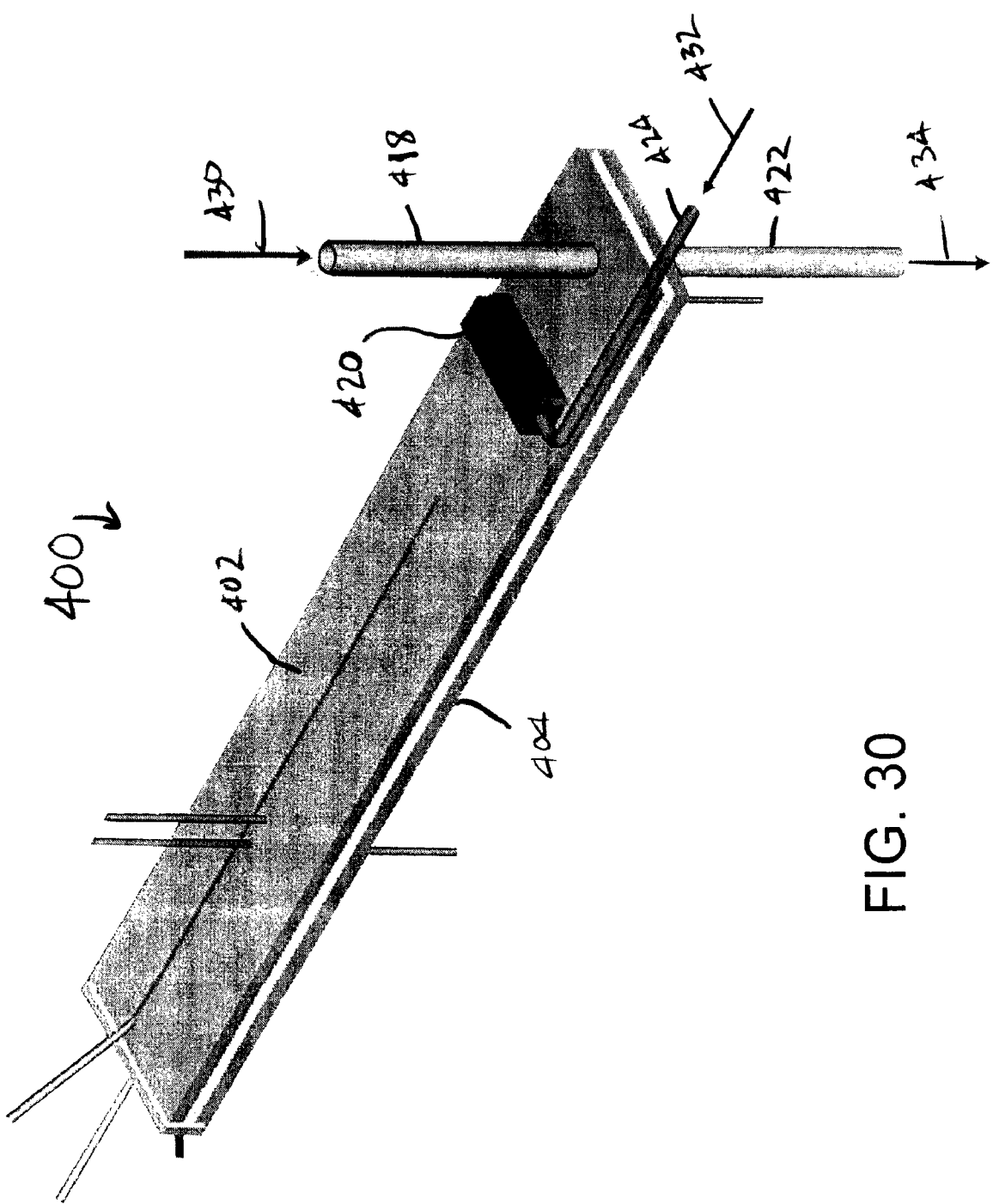
FIGS. 30-35 are illustrations of the microchannel reactor identified in Example 1.

In one embodiment, a plurality of the microchannel reactors 110 may be housed in reaction vessel 300A which is illustrated in FIG. 29. Referring to FIG. 29, the vessel 300A contains microchannel reactor 110, and inlets 320, 330 and 335. Inlet may be connected to a manifold which is provided for permitting the flow of the hydrocarbon reactant into the process microchannels in the microchannel reactor 110. Inlet 330 may be connected to a manifold which is provided for permitting the flow of the fuel into the combustion channels. Inlet 335 may be connected to a manifold which is provided for permitting the flow of the oxygen or a source of oxygen into the staged additional channels in the microchannel reactor 110. The vessel 300A includes shell 315 and insulation layer 318 which is positioned between the shell 315 and the microchannel reactor 110. Product may exit the microchannel reactor 110 at the top 325 of the microchannel reactor 110. Steam may flow in the gap 345 between the microchannel reactor 110 and the shell 315. The steam flowing in the gap 345 may be used to quench the reaction.

The vessels 300 and 300A may be constructed from any suitable material sufficient for operating under the pressures and temperatures required for operating the microchannel reactors. For example, the shell and heads of the vessels 300 and 300A may be constructed of cast steel. The flanges, couplings and pipes may be constructed of stainless steel or other suitable alloys. The vessels 300 and 300A may have any desired diameter, for example, from about 30 to about 500 cm, and in one embodiment from about 100 to about 300 cm. The axial length of the vessels 300 and 300A may be of any desired value, for example, from about 0.5 to about 50 meters, and in one embodiment from about 0.5 to about 15 meters, and in one embodiment from about 1 to about 10 meters.

As indicated above, the microchannel reactors 110 may comprise a plurality of process microchannels and heat exchange channels (or combustion channels and staged addition channels) stacked one above the other or positioned side-by-side. The microchannel reactors 110 may be in the form of cubic blocks as illustrated in FIGS. 27-29. Each of these cubic blocks may have a length, width and height, the length being in the range from about 10 to about 1000 cm, and in one embodiment in the range from about 50 to about 200 cm. The width may be in the range from about 10 to about 1000 cm, and in one embodiment in the range from about 50 to about 200 cm. The height may be in the range from about 10 to about 1000 cm, and in one embodiment in the range from about 50 to about 200 cm.

The microchannel reactors 110 may comprise a plurality of repeating units, each of which may include one or more process microchannels and one or more heat exchange channels (or one or more combustion channels and one or more staged addition channels). The repeating units that may be used include repeating units 200, 200A, 200B, 200C, 200D, 200E, 200F, 200G and 200H illustrated in FIGS. 8-14 and 23-24, respectively. The microchannel reactor 110 may comprise from about 1 to about 1000 of the repeating units 200, 200A, 200B, 200C, 200D, 200E, 200F, 200G or 200H and in one embodiment from about 3 to about 750, and in one embodiment from about 5 to about 500, and in one embodiment from about 5 to about 250, and in one embodiment from about 10 to about 100 of such repeating units.

The repeating unit 200, which is illustrated in FIG. 8, includes process microchannel 210 and heating section 240. The heating section 240 includes heat exchange microchannel 242 which extends lengthwise in the same direction as the process microchannel 210. The reactants enter the process microchannel 210 as indicated by arrow 212, flow through the process microchannel 210, are heated by the heating section 240, undergo reaction to form the product as indicated above, and flow out of the process microchannel 210 as indicated by arrow 214. The flow of the heat exchange fluid in the heat exchange channel 242 in the heating section may be co-current and/or counter-current to the flow of fluid in the process microchannel 210.

The repeating unit 200A illustrated in FIG. 9 is the same as the repeating unit 200 illustrated in FIG. 8 with the exception that the heat exchange channels 242 are orthogonal to the process microchannel 210. The flow of heat exchange fluid in the heat exchange channels 242 may be cross-current relative to the flow of fluid in the process microchannel 210.

Figure 10:
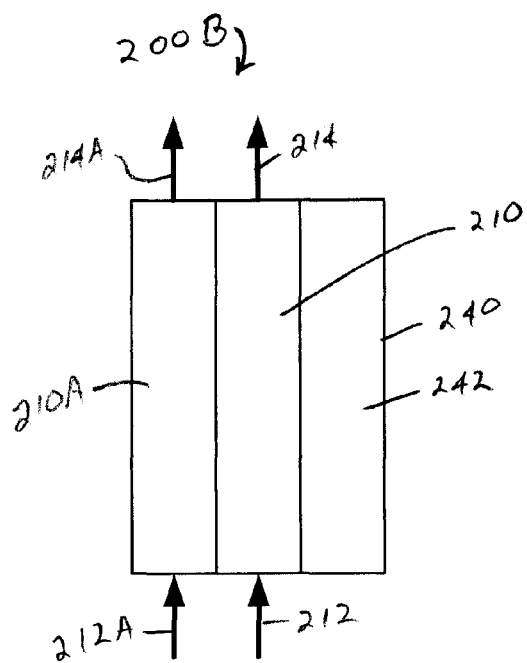

The repeating unit 200B illustrated in FIG. 10 is the same as the repeating unit 200 illustrated in FIG. 8 with the exception that two process microchannels, namely, process microchannels 210 and 210A, are positioned adjacent each other. Process microchannel 210 is positioned adjacent heating section 240. The heating section 240 provides heating for both process microchannels 210 and 210A. The reactants enter process microchannels 210 and 210A as indicated by arrows 212 and 212A, respectively, flow through the process microchannels, and undergo reaction to form product as indicated above. The product flows out of the process microchannels 210 and 210A as indicated by arrows 214 and 214A, respectively.

Figure 11:
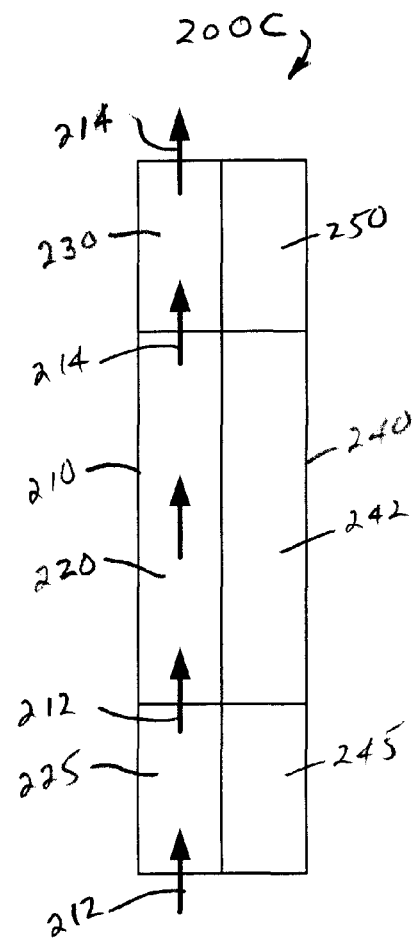
Figure 12:
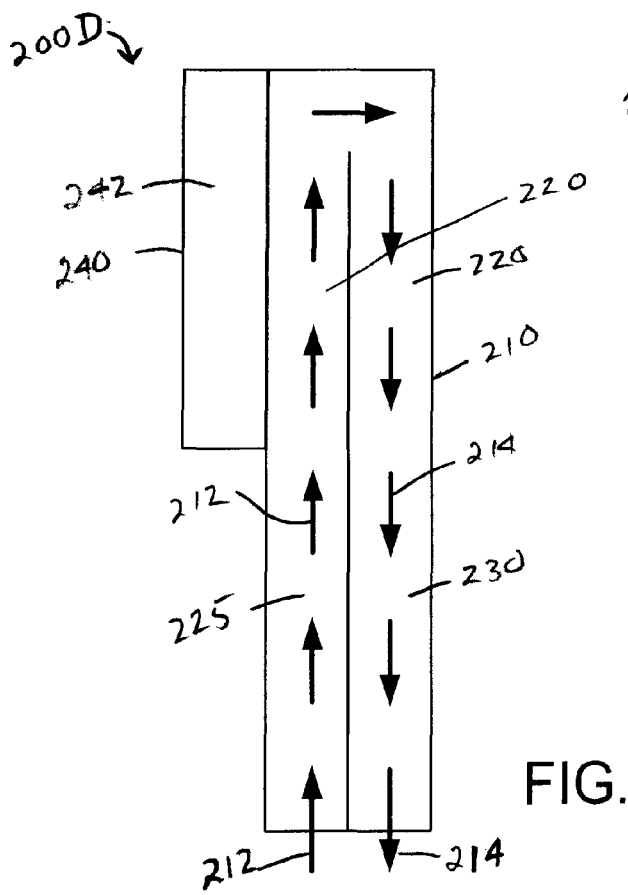

The repeating unit 200C illustrated in FIG. 11 is the same as the repeating unit 200 in FIG. 8 with the exception that the process microchannel 210 illustrated in FIG. 11 includes a reaction zone 220, a preheating zone 225 and a quenching zone 230. The preheating zone 225 is upstream of the reaction zone 220. The quenching zone 230 is downstream of the reaction zone 220. The preheating zone 225 is heated by heating section 245. The reaction zone 220 is heated by heating section 240. The quenching zone 230 is cooled by cooling section 250. The heating sections 240 and 245 and the cooling section 250 may each comprise heat exchange channels with appropriate heat exchange fluids flowing in the heat exchange channels. The reactants enter the preheating section 225, as indicated by arrow 212 and flow through the preheating section 225 where they are heated to a desired preheating temperature. The reactants flow from the preheating section 225 into the reaction zone 220 where they undergo reaction to form the product. The product flows from the reaction zone 220 through the quenching zone 230 wherein the reaction is quenched. The product flows from the quenching zone 230 out of the process microchannel 210 as indicated by arrow 214.

The repeating unit 200D is similar to the repeating unit 200C with the exception that the process microchannel 210 is in the form of an upside down U. Also, the preheating zone 225 and the quenching zone 230 are adjacent to each other and exchange with each other. The reaction zone 220 of the process microchannel 210 is heated by the heating section 240 which includes heat exchange channel 242. The reactants enter the process microchannel 210 as indicated by arrow 212, flow through preheating section 225 where they are preheated and then through reaction zone 220 where the reactants undergo reaction to form the product. The product flows from the reaction zone 220 through the quenching zone 230 where the reaction is quenched. The product flows out of the process microchannel 210 as indicated by arrow 214. The relatively cool reactants flowing in the preheating zone 225 are heated by the relatively hot product flowing through the quenching zone 230. As a result, heat transfers from the quenching zone 230 to the preheating zone 225.

The repeating unit 200E illustrated in FIG. 13 includes process microchannel 210 and heating sections 240 and 240A. Heating section 240 comprises combustion channel 260 and staged addition channels 270. The process microchannel 210 is in the form of an upside down U. The reactants enter the process microchannel 210 as indicated by arrow 212, flow through the process microchannel and undergo reaction with the result being the formation of the product as discussed above. The product flows out of the process microchannel 210 as indicated by arrow 214. The combustion channel 260 is an M-shaped combustion channel which includes reaction zones 268 wherein a combustion catalyst (not shown in the drawing) may be positioned. The combustion channel also includes apertured sections 265 in its sidewalls to permit the oxygen or source of oxygen to flow from the staged addition channels 270 into the combustion channel 260. The fuel (e.g., hydrogen or natural gas) enters the combustion channel 260 as indicated by arrows 280 and flows into the reaction zones 268. The oxygen or source of oxygen enters the staged addition channels 270 as indicated by arrows 282 and flows from the staged addition channels through the apertured sections 265 into the reaction zones 268 in the combustion channel 260. The fuel may be mixed with the oxygen or source of oxygen, contact the combustion catalyst, and undergo a combustion reaction which generates heat and combustion exhaust. The heat is transferred to the process microchannel 210. The combustion exhaust flows out of the combustion channel 260 as indicated by arrow 285. The heating section 240A is identical to the heating section 240 in both structure and operation, the only difference in the drawing being the use of the letter "A" after each numeral for identifying parts and features in heating section 240A that correspond to the same parts and features in the heating section 240.

The repeating unit 200F illustrated in FIG. 14 is the same as the repeating unit 200E illustrated in FIG. 13 with the exception that the process microchannel 210 in repeating unit 200F is a straight-run, flow-through microchannel which includes reaction zone 220. Also, process microchannel 210 in repeating unit 200F extends beyond the heating sections 240 and 240A to include quenching zone 225. Repeating unit 200F includes quenching channels 280 and 280A which may be used for injecting a quenching fluid (e.g., low temperature steam) into the product in the quenching zone 225 as indicated by arrows 282 and 282A. Alternatively, the quenching channels 280 and 280A may be heat exchange channels which may be used to cool the product and quench the reaction. An advantage of using the straight-run flow through process microchannel 210 is that the reactants and product may flow through the process microchannel at a sufficient flow rate to remove or "blow out" any carbon deposits that may form in the process microchannel. The flow of reactants and product may be at a superficial velocity of at least about 0.001 meters per second (m/s), and in one embodiment in the range from about 0.001 to about 100 m/s.

In FIGS. 13 and 14 the various channels as illustrated are shown as being spaced apart for purposes of facilitating the illustrations. However, the actual devices would include the channels being adjacent to each other, that is, in contact with one another. Also, the walls of one channel shown in these drawings that would be adjacent to a wall of another channel may, in fact, be a common wall. For example, in FIG. 13, wall 211 of process microchannel 210 and wall 261 of combustion channel 260 may comprise a common wall.

In each of FIGS. 8-14, 23 and 24, the common walls between the process microchannels and heat exchange channels (or combustion channels) may be referred to as heat transfer walls.

Figure 15:
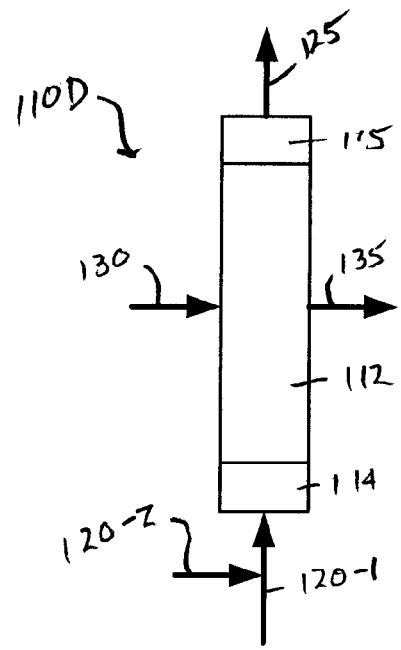
Figure 16:
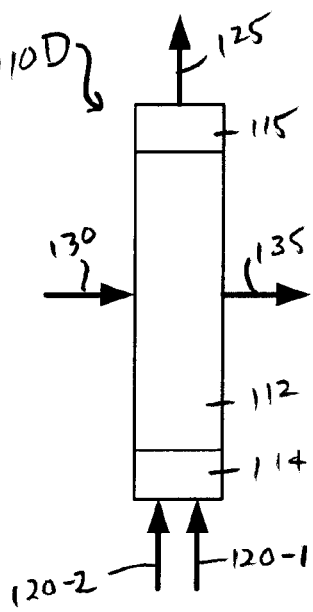
Figure 17:
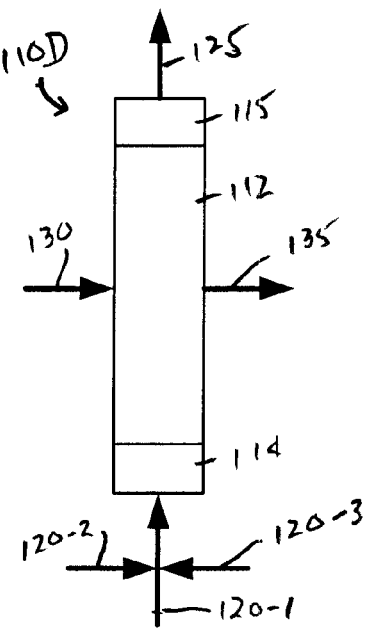
Figure 18:
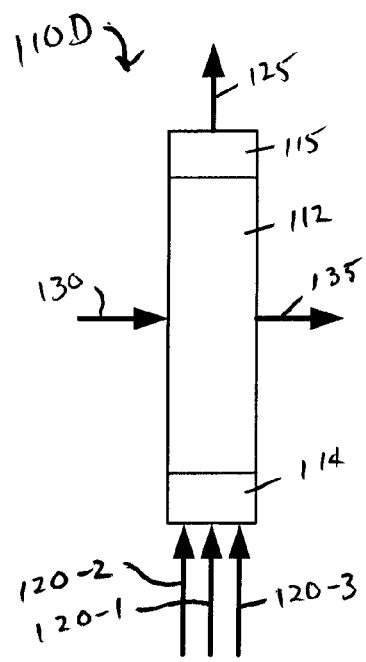
Figure 19:
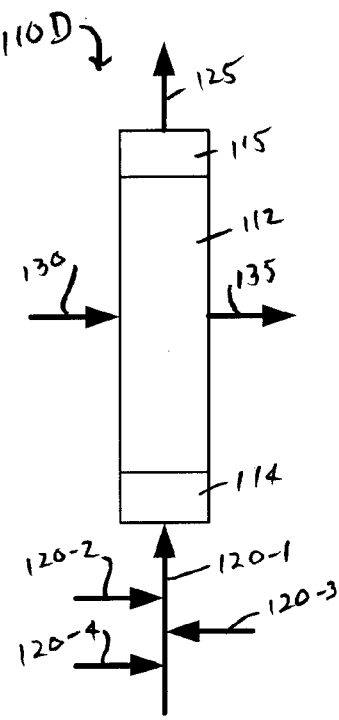
Figure 20:
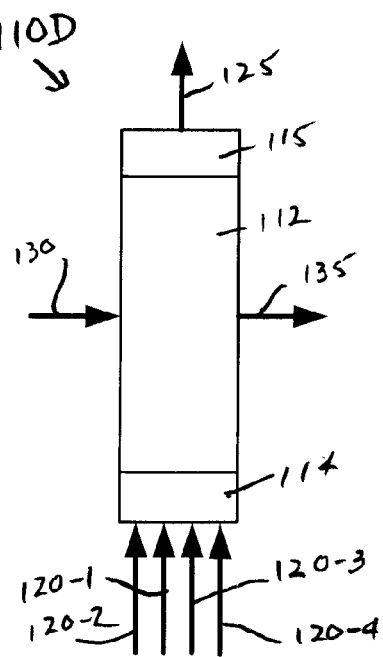

The reactants, that is, the feed composition and steam, and optionally hydrogen and/or oxygen or source of oxygen, may be mixed prior to entering the microchannel reactor 110 or they may be mixed in the microchannel reactor 110. When mixed in the microchannel reactor 110, the reactants may be mixed in headers or manifold assemblies prior to entering the process microchannels or they may be mixed in the process microchannels. This is illustrated in FIGS. 15-24. In FIGS. 15-22, microchannel reactor 110D is illustrated. Microchannel reactor 110D is the same as microchannel reactor 110D described above with reference to FIG. 6. Referring to FIG. 15, the feed composition (i.e., the hydrocarbon reactant) indicated by arrow 120-1 is mixed with the steam indicated by arrow 120-2 prior to entering the microchannel reactor 110D. Referring to FIG. 16, the feed composition indicated by arrow 120-1 and the steam indicated by arrow 120-2 are mixed in the microchannel reactor 110D. Referring to FIG. 17, the feed composition indicated by arrow 120-1, the steam indicated by arrow 120-2, and the hydrogen or oxygen or source of oxygen as indicated by arrow 120-3 are mixed prior to entering the microchannel reactor 110D. Referring to FIG. 18, the feed composition indicated by arrow 120-1, the steam indicated by arrow 120-2, and the hydrogen or oxygen or source of oxygen indicated by arrow 120-3 are mixed in the microchannel reactor 110D. Referring to FIG. 19, the feed composition indicated by arrow 120-1, the steam indicated by arrow 120-2, the hydrogen indicated by arrow 120-3 and the oxygen or source of oxygen indicated by arrow 120-4 are mixed prior to entering the microchannel reactor 110D. Referring to FIG. 20, the feed composition indicated by arrow 120-1, the steam indicated by arrow 120-2, the hydrogen indicated by arrow 120-3, and the oxygen or source of oxygen indicated by arrow 120-4 are mixed in the microchannel reactor 110D. Combinations of the foregoing may be employed. For example, part of the steam may be mixed with the feed composition prior to entering the microchannel reactor 110D, and part of the steam may be mixed with the feed composition in the microchannel reactor 110D. Similarly, part of the hydrogen and/or oxygen or source of oxygen may be mixed with the feed composition and/or steam prior to entering the microchannel reactor 110, and part may be mixed in the microchannel reactor 110.

Figure 21:
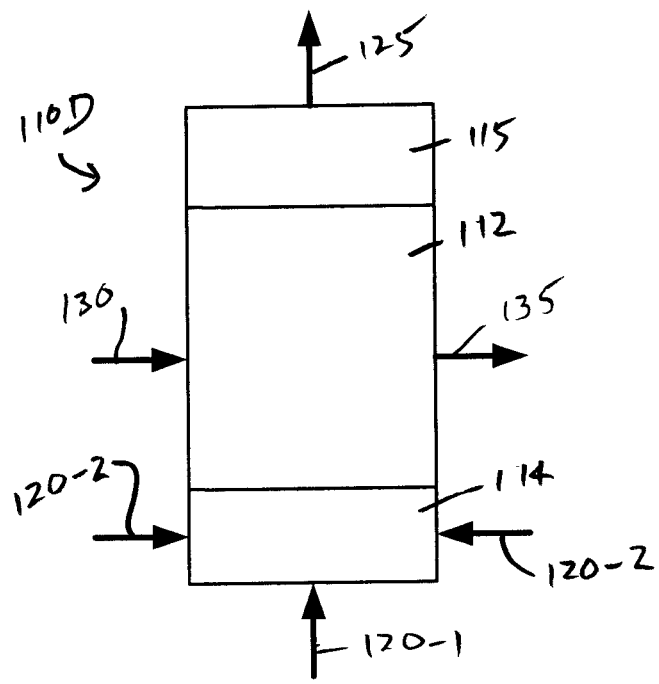
Figure 22:
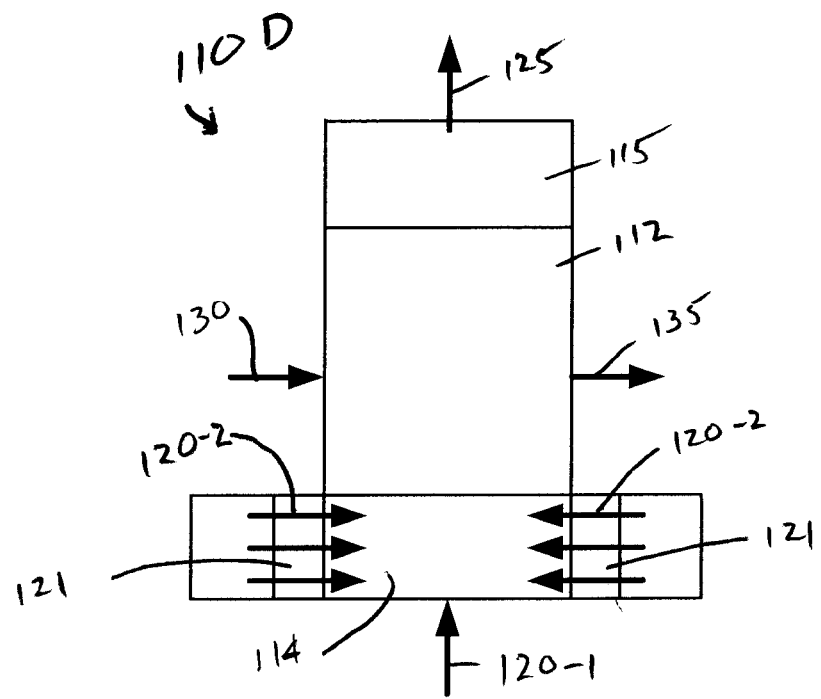

The mixing of the feed composition and steam in header or manifold assembly 114 of microchannel reactor 110D is shown in FIGS. 21 and 22. Referring to FIG. 21, streams of steam indicated by arrow 120-2 are injected into a stream of the feed composition indicated by arrow 120-1 in the header or manifold assembly 114 to provide the desired mixture of feed composition and steam in the header or manifold assembly. The mixture of feed composition and steam then flows into the process microchannels in the microchannel reactor core 112 and undergoes reaction. The embodiment illustrated in FIG. 22 is similar to the embodiment illustrated in FIG. 21 with the exception that in FIG. 22 the header or manifold assembly includes apertured sections 121. The steam indicated by arrows 120-2 flows through the apertured sections 121 into the header or manifold assembly 114 where it contacts the feed composition and forms the desired mixture of feed composition and steam. The mixture of feed composition and steam then flows from the header or manifold assembly 114 into the process microchannels in the microchannel reactor core 112 and undergoes reaction. Combinations of the foregoing with hydrogen and/or oxygen or a source of oxygen may be employed. For example, hydrogen and/or oxygen or a source of oxygen may be mixed with the steam in the header or manifold assembly. Similarly, part of the steam (and/or hydrogen and/or oxygen or a source of oxygen) may be mixed with the feed composition in the header or manifold assembly 114 and part may be mixed in the process microchannels.

Figure 23:
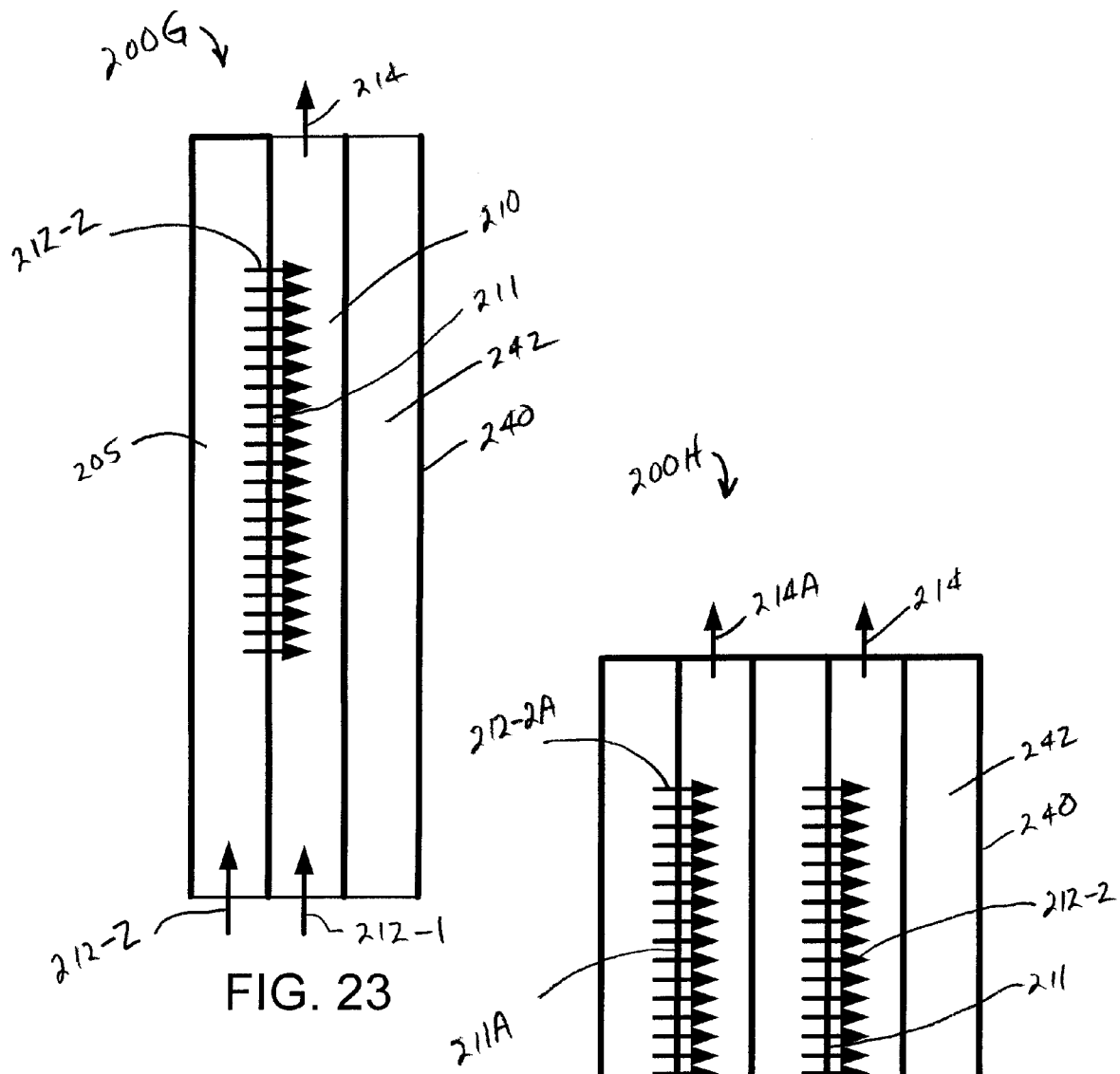
Figure 24:
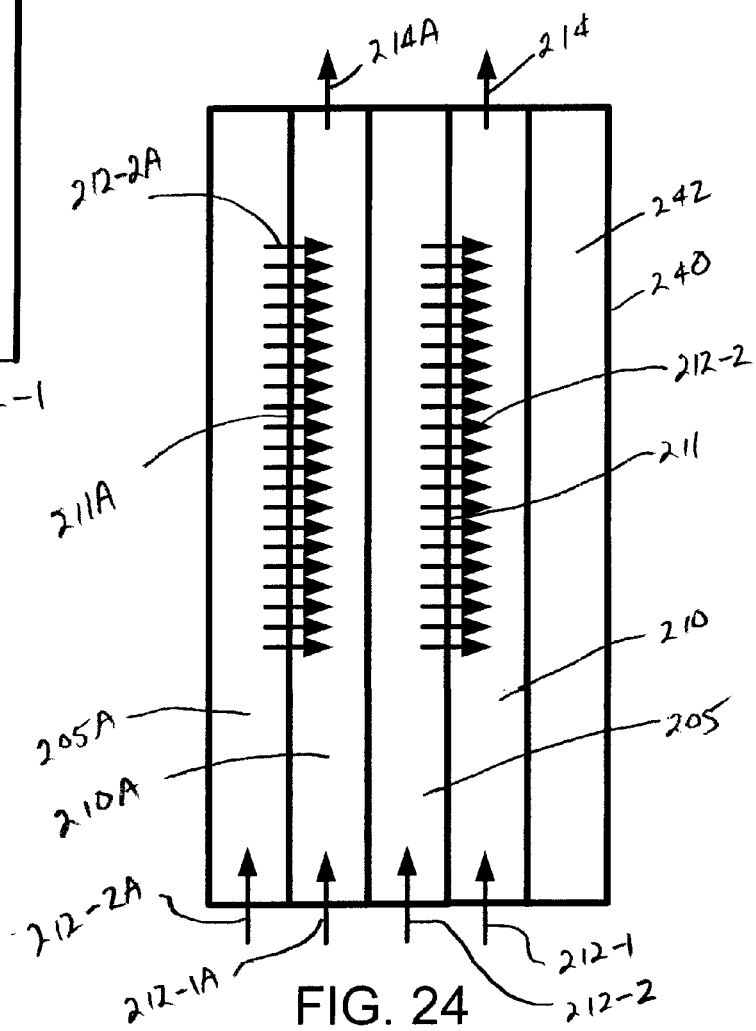

Repeating units 200G and 200H which provide for the mixing of the feed composition and steam in the process microchannels are illustrated in FIGS. 23 and 24, respectively. Referring to FIG. 23, repeating unit 200G includes heating section 240, process microchannel 210 and staged addition channel 205. The heating section 240 includes heat exchange channel 242 which extends lengthwise in the same direction as the process microchannel 210. The staged addition channel 205 is adjacent to the process microchannel 210. The process microchannel 210 includes apertured section 211 which is provided for permitting the flow of steam from the staged addition channel 205 into the process microchannel 210. The feed composition enters process microchannel 210 as indicated by arrow 212-1. The steam enters staged addition channel 205 as indicated by arrow 212-2. The steam flows from the staged addition channel 205 through apertured section 211 into process microchannel 210 where it is mixed with the feed composition. The mixture of feed composition and steam are heated in process microchannel 210 by heating section 240, and undergoes reaction to form the product as indicated above. The product flows out of process microchannel 210 as indicated by arrow 214. Alternatively, hydrogen and/or oxygen or a source of oxygen may be combined with the steam stream 212-2, or either or both hydrogen and oxygen or a source of oxygen may enter the process microchannel 210 from different staged addition channels through different apertured sections not shown in the drawings. The different apertured sections may be adjacent the apertured section 211, and/or upstream and/or downstream of the apertured section 211.

Repeating unit 200H illustrated in FIG. 24 is the same as repeating unit 200G with the exception that repeating 200H includes a second process microchannel 210A and second staged addition channel 205A. The process microchannel 210A and staged addition channel 205A are identical to the process microchannel 210 and staged addition channel 205. Similarly, the apertured section 211A in process microchannel 210A is the same as the apertured section 211 in process microchannel 210. The feed composition enters the process microchannels 210 and 210A as indicated by arrows 212-1 and 212-1A, respectively. The steam (and optionally hydrogen and/or oxygen or a source of oxygen) enters staged addition channels 205 and 205A as indicated by arrows 212-2 and 212-2A, respectively. The steam flows through the apertured sections 211 and 211A into the process microchannels 210 and 210A, respectively, to provide the desired reaction mixture of feed composition and steam (and optionally hydrogen and/or oxygen or a source of oxygen) in each of the process microchannels 210 and 210A. The process microchannels 210 and 210A are heated by the heating section 240. Product is formed in each of the process microchannels 210 and 210A and flows out of the process microchannels as indicated by arrows 214 and 214A.

The heat exchange channels 242 (or combustion channels 260 and staged addition channels 270) as well as the staged addition channels 205 in the microchannel reactor 110 may be microchannels or they may have dimensions that would characterize them as not being microchannels. For example, these channels may have internal heights or widths up to about 50 mm, and in one embodiment up to about 25 mm, and in one embodiment up to about 15 mm. The process microchannels 210 in the microchannel reactor 110 are microchannels. Each of the channels may have a cross-section having any shape, for example, a square, rectangle, circle, semicircle, etc. Each microchannel may have an internal height of up to about 10 mm, and in one embodiment up to about 5 mm, and in one embodiment up to about 2 mm, and in one embodiment up to about 2 mm. In one embodiment, the height may be in the range of about 0.05 to about 10 mm, and in one embodiment from about 0.05 to about 5 mm, and in one embodiment from about 0.05 to about 2 mm, and in one embodiment about 0.05 to about 1.5 mm. The width of each of the channels may be of any dimension, for example, up to about 3 meters, and in one embodiment from about 0.01 to about 3 meters, and in one embodiment about 0.1 to about 3 meters. The length of each channel may be of any dimension, for example, up to about 10 meters, and in one embodiment about 0.2 to about 10 meters, and in one embodiment from about 0.2 to about 6 meters, and in one embodiment from 0.2 to about 3 meters.

The process microchannels, staged addition channels and heat exchange channels (or combustion channels and staged addition channels) in the microchannel reactor 110 may have rectangular cross sections and be aligned in side-by-side vertically oriented planes or horizontally oriented stacked planes. These planes may be tilted at an inclined angle from the horizontal. These configurations may be referred to as parallel plate configurations. These channels may be arranged in modularized compact units for scale-up.

The microchannel reactor 110 may be made of any material that provides sufficient strength, dimensional stability and heat transfer characteristics to permit operation of the inventive process. These materials may include steel; aluminum, titanium; nickel, platinum; rhodium; copper; chromium; brass; alloys of any of the foregoing metals; quartz; silicon; or a combination of two or more thereof.

The microchannel reactor 110 may be fabricated using known techniques including wire electrodischarge machining, conventional machining, laser cutting, photochemical machining, electrochemical machining, molding, water jet, stamping, etching (for example, chemical, photochemical or plasma etching) and combinations thereof.

The microchannel reactor 110 may be constructed by forming shims with portions removed that allow flow passage. A stack of shims may be assembled via diffusion bonding, laser welding, diffusion brazing, and similar methods to form an integrated device. The microchannel reactors may be assembled using a combination of shims or laminae and partial sheets or strips. In this method, the channels or void areas may be formed by assembling strips or partial sheets to reduce the amount of material required.

The microchannel reactor 110 may include one or more passivation layers on one or more of its interior surfaces to prevent or reduce coking. The interior surfaces with the one or more passivation layers may include part or all of the interior surfaces of the process microchannels, staged addition channels and/or heat exchange channels (or combustion channels and staged addition channels), as well as part or all of the interior surfaces of the headers or manifold assemblies and the footers or manifold assemblies. The passivation layers may comprise $Al_2O_3$, $SiO_2$, $TiO_2$, metal aluminides, and/or combinations of two or more thereof. The one or more passivation layers may comprise coating layers. The one or more passivation layers may be applied using wash coating or vapor deposition. These layers may be applied in a post assembly step during fabrication of the microchannel reactor. The one or more passivation layers may have a thickness in the range from about 1 to about 100 microns.

The process microchannels and/or heat exchange channels (or combustion channels) may contain one or more surface features in the form of depressions in and/or projections from one or more interior walls of the channels. Examples are shown in FIGS. 25 and 26. The surface features may be used to disrupt the flow of fluid flowing in the channels. These disruptions in flow may enhance mixing and/or heat transfer. The surface features may be in the form of patterned surfaces. The microchannel reactor 110 may be made by laminating a plurality of shims together. One or both major surfaces of the shims may contain surface features. Alternatively, the microchannel reactor 110 may be assembled using some sheets or shims and some strips, or partial sheets to reduce the total amount of metal required to construct the device. In one embodiment, a shim containing surface features may be paired (on opposite sides of a channel) with another shim containing surface features. Pairing may create better mixing or heat transfer enhancement as compared to channels with surface features on only one major surface. In one embodiment, the patterning may comprise diagonal recesses that are disposed over substantially the entire width of a channel surface. The patterned surface feature area of a wall may occupy part of or the entire length of a channel surface. In one embodiment, surface features may be positioned over at least about 10%, and in one embodiment at least about 20%, and in one embodiment at least about 50%, and in one embodiment at least about 80% of the length of a channel surface. Each diagonal recesses may comprise one or more angles relative to the flow direction. Successive recessed surface features may comprise similar or alternate angles relative to other recessed surface features.

In embodiments wherein surface features may be positioned on or in more than one microchannel wall, the surface features on or in one wall may have the same (or similar) pattern as found on a second wall, but rotated about the centerline of the main channel mean bulk flow direction. In embodiments wherein surface features may be on or in opposite walls, the surface features on or in one wall may be approximately mirror images of the features on the opposite wall. In embodiments wherein surface features are on or in more than one wall, the surface features on or in one wall may be the same (or similar) pattern as found on a second wall, but rotated about an axis which is orthogonal to the main channel mean bulk flow direction. In other words, the surface features may be flipped 180 degrees relative to the main channel mean bulk flow direction and rotated about the centerline of the main channel mean bulk flow. The surface features on or in opposing or adjacent walls may or may not be aligned directly with one another, but may be repeated continuously along the wall for at least part of the length of the wall. Surface features may be positioned on three or more interior surfaces of a channel. For the case of channel geometries with three or fewer sides, such as triangular, oval, elliptical, circular, and the like, the surface features may cover from about 20% to about 100% of the perimeter of the channel.

In one embodiment, a patterned surface may comprise multiple patterns stacked on top of each other. A pattern or array of holes may be placed adjacent to a heat transfer wall and a second pattern, such as a diagonal array of surface features may be stacked on top and adjacent to an open channel for flow. A sheet adjacent to an open gap may have patterning through the thickness of the sheet such that flow may pass through the sheet into an underlying pattern. Flow may occur as a result of advection or diffusion. As an example, a first sheet with an array of through holes may be placed over a heat transfer wall, and a second sheet with an array of diagonal through slots may be positioned on the first sheet. This may create more surface area for adhering a catalyst. In one embodiment, the pattern may be repeated on at least one other wall of the process microchannel. The patterns may be offset on opposing walls. The innermost patterned surfaces (those surfaces bounding a flow channel) may contain a pattern such as a diagonal array. The diagonal arrays may be oriented both "with" the direction of flow or one side oriented with the direction of flow and the opposing side oriented "against" the direction of flow. By varying surface features on opposing walls, different flow fields and degrees of vorticity may be created in the fluid that travels down the center and open gap.

The surface features may be oriented at angles relative to the direction of flow through the channels. The surface features may be aligned at an angle from about 1° to about 89°, and in one embodiment from about 30° to about 75°, relative to the direction of flow. The angle of orientation may be an oblique angle. The angled surface features may be aligned toward the direction of flow or against the direction of flow. The flow of fluid in contact with the surface features may force some of the fluid into depressions in the surface features, while other fluids may flow above the surface features. Flow within the surface features may conform with the surface feature and be at an angle to the direction of the bulk flow in the channel. As fluid exits the surface features it may exert momentum in the x and y direction for an x,y,z coordinate system wherein the bulk flow is in the z direction. This may result in a churning or rotation in the flow of the fluids. This pattern may be helpful for mixing.

Two or more surface feature regions within the process microchannels may be placed in series such that mixing of the fluids may be accomplished using a first surface feature region, followed by at least one second surface feature region where a different flow pattern may be used.

The surface features may have two or more layers stacked on top of each other or intertwined in a three-dimensional pattern. The pattern in each discrete layer may be the same or different. Flow may rotate or advect in each layer or only in one layer. Sub-layers, which may not be adjacent to the bulk flow path of the channel, may be used to create additional surface area. The flow may rotate in the first level of surface features and diffuse molecularly into the second or more sublayers to promote reaction. Three-dimensional surface features may be made via metal casting, photochemical machining, laser cutting, etching, ablation, or other processes where varying patterns may be broken into discrete planes as if stacked on top of one another. Three-dimensional surface features may be provided adjacent to the bulk flow path within the microchannel where the surface features have different depths, shapes, and/or locations accompanied by sub-features with patterns of varying depths, shapes and/or locations.

An example of a three-dimensional surface feature structure may comprise recessed oblique angles or chevrons at the interface adjacent the bulk flow path of the microchannel. Beneath the chevrons there may be a series of three-dimensional structures that connect to the surface features adjacent to the bulk flow path but are made from structures of assorted shapes, depths, and/or locations. It may be further advantageous to provide sublayer passages that do not directly fall beneath an open surface feature that is adjacent to the bulk flow path within the microchannel but rather connect through one or more tortuous two-dimensional or three-dimensional passages. This approach may be advantageous for creating tailored residence time distributions in the microchannels, where it may be desirable to have a wider versus more narrow residence time distribution.

The length and width of a surface feature may be defined in the same way as the length and width of a channel. The depth may be the distance which the surface feature sinks into or rises above the microchannel surface. The depth of the surface features may correspond to the direction of stacking a stacked and bonded microchannel device with surface features formed on or in the sheet surfaces. The dimensions for the surface features may refer the maximum dimension of a surface feature; for example the depth of a rounded groove may refer to the maximum depth, that is, the depth at the bottom of the groove.

The surface features may have depths that are up to about 5 mm, and in one embodiment up to about 2 mm, and in one embodiment in the range from about 0.01 to about 5 mm, and in one embodiment in the range from about 0.01 to about 2 mm, and in one embodiment in the range from about 0.01 mm to about 1 mm. The width of the surface features may be sufficient to nearly span the microchannel width (for example, herringbone designs), but in one embodiment (such as fill features) may span about 60% or less of the width of the microchannel, and in one embodiment about 50% or less, and in one embodiment about 40% or less, and in one embodiment from about 0.1% to about 60% of the microchannel width, and in one embodiment from about 0.1% to about 50% of the microchannel width, and in one embodiment from about 0.1% to about 40% of the microchannel width. The width of the surface features may be in the range from about 0.05 mm to about 100 cm, and in one embodiment in the range from about 0.5 mm to about 5 cm, and in one embodiment in the range from about 1 to about 2 cm.

Multiple surface features or regions of surface features may be included within a channel, including surface features that recess at different depths into one or more microchannel walls. The spacing between recesses may be in the range from about 0.01 mm to about 10 mm, and in one embodiment in the range from about 0.1 to about 1 mm. The surface features may be present throughout the entire length of a channel or in portions or regions of the channel. The portion or region having surface features may be intermittent so as to promote a desired mixing or unit operation (for example, separation, cooling, etc.) in tailored zones. For example, a one-centimeter section of a channel may have a tightly spaced array of surface features, followed by four centimeters of a flat channel without surface features, followed by a two-centimeter section of loosely spaced surface features. The term "loosely spaced surface features" may be used to refer to surface features with a pitch or feature to feature distance that is more than about five times the width of the surface feature.

The surface features may be positioned in one or more surface feature regions that extend substantially over the entire axial length of a channel. In one embodiment, a channel may have surface features extending over about 50% or less of its axial length, and in one embodiment over about 20% or less of its axial length. In one embodiment, the surface features may extend over about 10% to about 100% of the axial length of the channel, and in one embodiment from about 20% to about 90%, and in one embodiment from about 30% to about 80%, and in one embodiment from about 40% to about 60% of the axial length of a channel.

Each surface feature leg may be at an oblique angle relative to the bulk flow direction. The feature span length or span may be defined as being normal to the feature orientation. As an example, one surface feature may be a diagonal depression at a 45 degree angle relative to a plane orthogonal to the mean direction of bulk flow in the main channel with a 0.38 mm opening or span or feature span length and a feature run length of 5.6 mm. The run length may be the distance from one end to the other end of the surface feature in the longest direction, whereas the span or feature span length may be in the shortest direction (that is not depth). The surface feature depth may be the distance way from the main channel. For surface features with a nonuniform width (span), the span may be the average span averaged over the run length.

A surface feature may comprise a recess or a protrusion based on the projected area at the base of the surface feature or the top of the surface feature. If the area at the top of the surface feature is the same or exceeds the area at the base of the surface feature, then the surface feature may be considered to be recessed. If the area at the base of the surface feature exceeds the area at the top of the surface feature, then it may be considered to be protruded. For this description, the surface features may be described as recessed although it is to be understood that by changing the aspect ratio of the surface feature it may be alternatively defined as a protrusion. For a channel defined by walls that intersect only the tops of the surface features, especially for a flat channel, all surface features may be defined as recessed and it is to be understood that a similar channel could be created by protruding surface features from the base of a channel with a cross section that includes the base of the surface features.

The process microchannels and/or heat exchange channels (or combustion channels) may have at least about 20%, and in one embodiment at least about 35%, and in one embodiment at least about 50%, and in one embodiment at least about 70%, and in one embodiment at least about 90% of the interior surface of the channel (measured in cross-section perpendicular to length; i.e., perpendicular to the direction of net flow through the channel) that contains surface features. The surface features may cover a continuous stretch of at least about 1 cm, and in one embodiment at least about 5 cm. In the case of an enclosed channel, the percentage of surface feature coverage may be the portion of a cross-section covered with surface features as compared to an enclosed channel that extends uniformly from either the base or the top of the surface feature or a constant value in-between. The latter may be a flat channel. For example, if a channel has patterned top and bottom surfaces that are each 0.9 cm across (wide) and unpatterned side walls that are 0.1 cm high, then 90% of the surface of the channel would contain surface features.

The process microchannels and/or heat exchange channels (or combustion channels) may be enclosed on all sides, and in one embodiment the channel may have a generally square or rectangular cross-section (in the case of rectangular channel, surface feature patterning may be positioned on both major faces). For a generally square or rectangular channel, the channel may be enclosed on only two or three sides and only the two or three walled sides may be used in the above described calculation of percentage surface features. In one embodiment, the surface features may be positioned on cylindrical channels with either constant or varying cross section in the axial direction.

Each of the surface feature patterns may be repeated along one face of the channel, with variable or regular spacing between the surface features in the channel bulk flow direction. Some embodiments may have only a single leg to each surface feature, while other embodiments may have multiple legs (two, three, or more). For a wide-width channel, multiple surface features or columns of repeated surface features may be placed adjacent to one another across the width of the channel. For each of the surface feature patterns, the feature depth, width, span, and spacing may be variable or constant as the pattern is repeated along the bulk flow direction in the main channel. Also, surface feature geometries having an apex connecting two legs at different angles may have alternate embodiments in which the surface feature legs may not be connected at the apex.

The apertures in the apertured sections 265 (FIGS. 13 and 14), 121 (FIG. 22) and 211 (FIGS. 23 and 24) may be of sufficient size to permit the flow of the desired fluid through the apertured sections. The apertures may be referred to as pores. The apertured sections may have thicknesses in the range from about 0.01 to about 10 mm, and in one embodiment about 0.01 to about 5 mm, and in one embodiment about 0.01 to about 2 mm. The apertures may have average diameters in the range up to about 5000 microns, and in one embodiment up to about 1000 microns, and in one embodiment up to about 500 microns, and in one embodiment in the range from about 10 to about 500 microns. The apertured sections may be constructed of any material that provides sufficient strength and dimensional stability to permit the operation of the process. These materials may include: steel (e.g., stainless steel, carbon steel, and the like); monel; inconel; aluminum; titanium; nickel; platinum; rhodium; copper; chromium; brass; alloys of any of the foregoing metals; or a combination of two or more thereof. The apertures may be formed using known techniques such as laser drilling, microelectro machining system (MEMS), lithography electrodeposition and molding (LIGA), electrical sparkling, or electrochemical or photochemical etching.

The configuration of the microchannel reactor 110 may be tailored to match the reaction kinetics. Near the entrance or top of a first reaction zone of a process microchannel, the microchannel height or gap may be smaller than in a second reaction zone near the exit or bottom of the process microchannel. Alternatively, the reaction zones may be smaller than half the process microchannel length. For example, a first process microchannel height or gap may be used for the first 25%, 50%, 75%, or 90% of the length of the process microchannel for a first reaction zone, while a larger second height or gap may be used in a second reaction zone downstream from the first reaction zone. Other gradations in the process microchannel height or gap may be used. For example, a first height or gap may be used near the entrance of the microchannel to provide a first reaction zone, a second height or gap downstream from the first reaction zone may be used to provide a second reaction zone, and a third height or gap may be used to provide a third reaction zone near the exit of the microchannel. The first and third heights or gaps may be the same or different. The first and third heights or gaps may be larger or smaller than the second height or gap. The third height or gap may be smaller or larger than the second height or gap. The second height or gap may be larger or smaller than the third height or gap.

In one embodiment, the channels may be characterized by having bulk flow paths. The term "bulk flow path" refers to an open path (contiguous bulk flow region) within the channels. A contiguous bulk flow region allows rapid fluid flow through the channels without large pressure drops. In one embodiment, the flow of fluid in the bulk flow region is laminar. Bulk flow regions within each process microchannel and/or heat exchange channel (or combustion channel) may have a cross-sectional area of about 0.05 to about 10,000 mm$^2$, and in one embodiment about 0.05 to about 5000 mm$^2$, and in one embodiment about 0.1 to about 2500 mm$^2$. The bulk flow regions may comprise from about 5% to about 95%, and in one embodiment about 30% to about 80% of the cross-section of the process microchannels and/or heat exchange channels (or combustion channels).

The space velocity (or gas hourly space velocity (GHSV)) for the flow of fluid in the process microchannels and/or heat exchange channels (or combustion channels) may be at least about 1000 hr$^{-1}$ (normal liters of feed/hour/liter of reactor volume within the process microchannels). The term "reactor volume" may be used herein to refer to a volume within a reactor wherein the reaction rate is greater than 1% of the maximum reactor reaction rate. The space velocity may range from about 1000 to about 1,000,000 hr$^{-1}$, and in one embodiment from about 10,000 to about 100,000 hr$^{-1}$.

The pressure drop for fluids as they flow in the process microchannels and/or heat exchange channels (or combustion channels), may range up to about 10 atmospheres per meter of length of channel (atm/m), and in one embodiment up to about 5 atm/m, and in one embodiment up to about 3 atm/m.

The Reynolds Number for the flow of fluid in the process microchannels and/or heat exchange channels (or combustion channels) may be in the range of about 10 to about 8000, and in one embodiment from about 10 to about 4000, and in one embodiment about 100 to about 2000.

The heat exchange fluid entering the heat exchange channels of the microchannel reactor 110 may be at a temperature of about 200° C. to about 1200° C., and in one embodiment about 600° C. to about 1050° C. The heat exchange fluid exiting the heat exchange channels may be at a temperature in the range of about 100° C. to about 900° C., and in one embodiment about 200° C. to about 800° C. The residence time of the heat exchange fluid in the heat exchange channels may range from about 1 to about 2000 ms, and in one embodiment about 10 to about 500 ms.

The heat exchange fluid used in the heat exchange channels in the microchannel reactor 110 may be any heat exchange fluid suitable for heating the hydrocarbon/steam (and optionally hydrogen and/or oxygen or source of oxygen) endothermic reaction. These may include air, steam, gaseous nitrogen, other gases including inert gases, carbon monoxide, oils such as mineral oil, and heat exchange fluids such as Dowtherm A and Therminol which are available from Dow-Union Carbide.

The heat exchange channels used in the microchannel reactor 110 may comprise process channels wherein an exothermic process is conducted. These heat exchange process channels may be microchannels. Examples of exothermic processes that may be conducted in the heat exchange channels may include the formation of methanol from synthesis gas or ammonia synthesis. The incorporation of a simultaneous exothermic reaction to provide an improved heat source may enable a typical heat flux of roughly an order of magnitude above the convective cooling heat flux.

The heat flux for heat exchange in the microchannel reactor 110 may be in the range from about 0.01 to about 500 watts per square centimeter of surface area of the heat transfer walls (W/cm$^2$) in the microchannel reactor, and in one embodiment in the range from about 0.1 to about 250 W/cm$^2$, and in one embodiment from about 1 to about 125 W/cm$^2$, and in one embodiment, from about 1 to about 100 W/cm$^2$, and in one embodiment from about 1 to about 50 W/cm$^2$, and in one embodiment from about 1 to about 25 W/cm$^2$, and in one embodiment from about 1 to about 10 W/cm$^2$.

The control of heat exchange during the reaction processes, in one embodiment, may be advantageous for controlling selectivity towards the desired product due to the fact that added heating and/or quenching may reduce or eliminate the formation of undesired by-products from undesired parallel reactions with higher activation energies.

The pressure within each individual heat exchange channel in the microchannel reactor 110 may be controlled using passive structures (e.g., obstructions), orifices and/or mechanisms upstream of the heat exchange channels or in the channels. By controlling the pressure within each heat exchange channel, the temperature within each heat exchange microchannel can be controlled. A higher inlet pressure for each heat exchange channel may be used where the passive structures, orifices and/or mechanisms let down the pressure to the desired pressure. By controlling the temperature within each heat exchange channel, the temperature in the process microchannels may be controlled. Thus, for example, each process microchannel may be operated at a desired temperature by employing a specific pressure in the heat exchange channel adjacent to or in thermal contact with the process microchannel. This may provide the advantage of precisely controlled temperatures for each process microchannel. The use of precisely controlled temperatures for each process microchannel may provide the advantage of a tailored temperature profile and an overall reduction in the energy requirements for the process.

The combustion catalyst that may be used in the combustion channels may comprise Pd, Pr, Pt, Rh, Ni, Cu, and/or an oxide thereof, or a mixture of two or more thereof. In one embodiment, the combustion catalyst may further comprise $Al_2O_3$, $SiO_2$, MgO, or a mixture of two or more thereof. In one embodiment, the combustion catalyst may be derived from a solution of $Pd(NO_3)_2$ which is deposited on a layer of $Al_2O_3$. In one embodiment, the combustion catalyst may comprise a layer of Pr and Pd using precursors in the form of nitrates, and a layer of Pt using a solution of $Pt(NH_3)_4(NO_3)_2$.

The combustion catalyst may be positioned in a single combustion zone or it may be positioned in more than one combustion zone in the combustion channel. The same or different catalyst may be used in each combustion zone. The catalyst may be a graded catalyst.

The combustion catalyst may have any size and geometric configuration that fits within the process microchannels. The catalyst may be in the form of particulate solids (e.g., pellets, powder, fibers, and the like) having a median particle diameter of about 1 to about 1000 μm (microns), and in one embodiment about 10 to about 500 μm, and in one embodiment about 25 to about 250 μm.

In one embodiment, the combustion catalyst may be in the form of a fixed bed of particulate solids. The median particle diameter of the particulate solids may be small, and the length of each process microchannel may be relatively short. The median particle diameter may be in the range of about 1 to about 1000 μm, and in one embodiment about 10 to about 500 μm, and the length of each process microchannel may be in the range of up to about 500 cm, and in one embodiment about 10 to about 500 cm, and in one embodiment about 50 to about 300 cm.

The combustion catalyst may be supported on a porous support structure such as a foam, felt, wad or a combination thereof. The term "foam" is used herein to refer to a structure with continuous walls defining pores throughout the structure. The term "felt" is used herein to refer to a structure of fibers with interstitial spaces therebetween. The term "wad" is used herein to refer to a structure of tangled strands, like steel wool. The catalyst may be supported on a honeycomb structure. The catalyst may be supported on a flow-by support structure such as a felt with an adjacent gap, a foam with an adjacent gap, a fin structure with gaps, a washcoat on any inserted substrate, or a gauze that is parallel to the flow direction with a corresponding gap for flow.

The combustion catalyst may be supported on a flow-through support structure such as a foam, wad, pellet, powder, or gauze. The support structure for a flow-through catalyst may be formed from a material comprising silica gel, foamed copper, sintered stainless steel fiber, steel wool, alumina, or a combination of two or more thereof. In one embodiment, the support structure may be made of a heat conducting material, such as a metal, to enhance the transfer of heat to or from the catalyst.

The combustion catalyst may be directly washcoated on the interior walls of the combustion channels, grown on the channel walls from solution, or coated on a fin structure. The catalyst may be in the form of a single piece of porous contiguous material, or many pieces in physical contact. In one embodiment, the catalyst may comprise a contiguous material and have a contiguous porosity such that molecules can diffuse through the catalyst. In this embodiment, the fluids flow through the catalyst rather than around it. In one embodiment, the cross-sectional area of the catalyst may occupy from about 1 to about 99%, and in one embodiment about 10 to about 95% of the cross-sectional area of the combustion channels. The catalyst may have a surface area, as measured by BET, of greater than about 0.5 $m^2/g$, and in one embodiment greater than about 2 $m^2/g$.

The combustion catalyst may comprise a porous support, an interfacial layer on the porous support, and a catalyst material on the interfacial layer. The interfacial layer may be solution deposited on the support or it may be deposited by chemical vapor deposition or physical vapor deposition. In one embodiment the catalyst has a porous support, a buffer layer, an interfacial layer, and a catalyst material. Any of the foregoing layers may be continuous or discontinuous as in the form of spots or dots, or in the form of a layer with gaps or holes. The porous support may have a porosity of at least about 5% as measured by mercury porosimetry and an average pore size (sum of pore diameters divided by number of pores) of about 1 to about 1000 microns. The porous support may be a porous ceramic or a metal foam. Other porous supports that may be used include carbides, nitrides, and composite materials. The porous support may have a porosity of about 30% to about 99%, and in one embodiment about 60% to about 98%. The porous support may be in the form of a foam, felt, wad, or a combination thereof. The open cells of the metal foam may range from about 20 pores per inch (ppi) to about 3000 ppi, and in one embodiment about 20 to about 1000 ppi, and in one embodiment about 40 to about 120 ppi. The term "ppi" refers to the largest number of pores per inch (in isotropic materials the direction of the measurement is irrelevant; however, in anisotropic materials, the measurement is done in the direction that maximizes pore number).

The buffer layer, when present, may have a different composition and/or density than both the porous support and the interfacial layers, and in one embodiment has a coefficient of thermal expansion that is intermediate the thermal expansion coefficients of the porous support and the interfacial layer. The buffer layer may be a metal oxide or metal carbide. The buffer layer may comprise $Al_2O_3$, $TiO_2$, $SiO_2$, $ZrO_2$, or combination thereof. The $Al_2O_3$ may be $\alpha$-$Al_2O_3$, $\gamma$-$Al_2O_3$ or a combination thereof. The buffer layer may be formed of two or more compositionally different sublayers. For example, when the porous support is metal, for example a stainless steel foam, a buffer layer formed of two compositionally different sub-layers may be used. The first sublayer (in contact with the porous support) may be $TiO_2$. The second sublayer may be $\alpha$-$Al_2O_3$ which is placed upon the $TiO_2$. In one embodiment, the $\alpha$-$Al_2O_3$ sublayer is a dense layer that provides protection of the underlying metal surface. A less dense, high surface area interfacial layer such as alumina may then be deposited as support for a catalytically active layer. In one embodiment, the buffer layer may comprise a metal aluminide formed by a reaction between a reactive gas and a metal surface.

The porous support may have a thermal coefficient of expansion different from that of the interfacial layer. In such a case a buffer layer may be needed to transition between the two coefficients of thermal expansion. The thermal expansion coefficient of the buffer layer can be tailored by controlling its composition to obtain an expansion coefficient that is compatible with the expansion coefficients of the porous support and interfacial layers. The buffer layer should be free of openings and pin holes to provide superior protection of the underlying support. The buffer layer may be nonporous. The buffer layer may have a thickness that is less than one half of the average pore size of the porous support. The buffer layer may have a thickness of about 0.05 to about 10 μm, and in one embodiment about 0.05 to about 5 μm.

In one embodiment adequate adhesion and chemical stability may be obtained without a buffer layer. In this embodiment the buffer layer may be omitted.

The interfacial layer may comprise nitrides, carbides, sulfides, halides, metal oxides, carbon, or a combination thereof. The interfacial layer provides high surface area and/or provides a desirable catalyst-support interaction for supported catalysts. The interfacial layer may be comprised of any material that is conventionally used as a catalyst support. The interfacial layer may comprise a metal oxide. Examples of metal oxides that may be used include. α-$Al_2O_3$, $SiO_2$, $ZrO_2$, $TiO_2$, tungsten oxide, magnesium oxide, vanadium oxide, chromium oxide, manganese oxide, iron oxide, nickel oxide, cobalt oxide, copper oxide, zinc oxide, molybdenum oxide, tin oxide, calcium oxide, aluminum oxide, lanthanum series oxide(s), zeolite(s) and combinations thereof. The interfacial layer may serve as a catalytically active layer without any further catalytically active material deposited thereon. The interfacial layer may be used in combination with a catalytically active layer. The interfacial layer may also be formed of two or more compositionally different sublayers. The interfacial layer may have a thickness that is less than one half of the average pore size of the porous support. The interfacial layer thickness may range from about 0.5 to about 100 μm, and in one embodiment from about 1 to about 50 microns. The interfacial layer may be either crystalline or amorphous. The interfacial layer may have a BET surface area of at least about 1 $m^2$/g.

The combustion catalyst may be deposited on the interfacial layer. Alternatively, the catalyst material may be simultaneously deposited with the interfacial layer. The catalyst layer may be intimately dispersed on the interfacial layer. That the catalyst layer is "dispersed on" or "deposited on" the interfacial layer includes the conventional understanding that microscopic catalyst particles are dispersed: on the support layer (i.e., interfacial layer) surface, in crevices in the support layer, and in open pores in the support layer.

The combustion catalyst may be supported by fin assemblies comprising parallel spaced fins positioned in the combustion channels. Fin assemblies that may be used are disclosed in U.S. Patent Publication 2004/0228781 A1, which is incorporated herein by reference.

In a scale up device, for certain applications, it may be required that the mass of the process fluid be distributed uniformly among the microchannels. Such an application may be when the process fluid is required to be heated or cooled down with adjacent heat exchange channels. The uniform mass flow distribution may be obtained by changing the cross-sectional area from one parallel microchannel to another microchannel. The uniformity of mass flow distribution may be defined by Quality Index Factor (Q-factor) as indicated below. A Q-factor of 0% means absolute uniform distribution.

$$Q = \frac{\dot{m}_{max} - \dot{m}_{min}}{\dot{m}_{max}} \times 100$$

A change in the cross-sectional area may result in a difference in shear stress on the wall. In one embodiment, the Q-factor for the SMR microchannel reactor 130 and/or Fischer-Tropsch microchannel reactors 150 and/or 170 may be less than about 50%, and in one embodiment less than about 20%, and in one embodiment less than about 5%, and in one embodiment less than about 1%.

The superficial velocity for fluid flowing in the process microchannels may be at least about 0.01 meters per second (m/s), and in one embodiment at least about 0.1 m/s, and in one embodiment in the range from about 0.01 to about 100 m/s, and in one embodiment in the range from about 0.01 to about 1 m/s, and in one embodiment in the range from about 0.1 to about 10 m/s, and in one embodiment in the range from about 1 to about 100 m/s.

The free stream velocity for fluid flowing in the process microchannels may be at least about 0.001 m/s, and in one embodiment at least about 0.01 m/s, and in one embodiment in the range from about 0.001 to about 200 m/s, and in one embodiment in the range from about 0.01 to about 100 m/s, and in one embodiment in the range from about 0.01 to about 200 m/s.

The contact time in the microchannel reactor may be in the range from about 1 to about 100 milliseconds (ms), and in one embodiment in the range from about 2 to about 95 ms, and in one embodiment in the range from about 5 to about 90 ms, and in one embodiment in the range from about 5 to about 80 ms, and in one embodiment in the range from about 5 to about 70 ms, and in one embodiment in the range from about 5 to about 60 ms, and in one embodiment in the range from about 5 to about 50 ms, and in one embodiment in the range from about 7 to about 50 ms, and in one embodiment in the range from about 10 to about 50 ms.

The reactants and products may flow through the microchannel reactor at a rate of at least about 5 standard liters per minute (SLPM), and in one embodiment at least about 7 SLPM, and in one embodiment at least about 10 SLPM, and in one embodiment at least about 15 SLPM, and in one embodiment at least about 20 SLPM.

Example 1

A process for the conversion of ethane and steam, or ethane and steam in combination with hydrogen and oxygen, to ethylene is conducted in the microchannel reactor illustrated in FIGS. 30-35. Referring to FIGS. 30-35, microchannel reactor 400 includes upper plate 402, lower plate 404 and separating shim 405. A pre-heat zone 406 is formed in the space between the upper plate 402 and the separating shim 405. A reaction zone 407 is formed in the space between the lower plate 404 and the separating shim 405. The plates 402 and 404, and the separating shim 405 are made of Inconel 617. The plates 402 and 404 have the dimensions of 10×30 cm. A hydrocarbon reactant (i.e., ethane) inlet orifice 409 and a steam (or steam in combination with hydrogen and oxygen) inlet slot 408 are formed in the upper plate 402. A product outlet orifice 410 is formed in the lower plate 404. Process microchannel layer 412, which includes a plurality of parallel spaced process microchannels 414, is mounted on lower plate 404 and positioned between the lower plate 404 and the separating shim 405. A Pt catalyst is positioned in the process microchannels. However, the Pt catalyst accounts for no more than 2% of the conversion of ethane to ethylene. Conduit 418 is connected to inlet 409 and provides for the flow of hydrocarbon reactant (i.e., ethane) into the pre-heat zone through inlet orifice 409. Steam inlet manifold 420 is connected to steam slot 408 and conduit 424 and provides for the flow of steam (or steam in combination with hydrogen and oxygen) into the pre-heat zone 406. Conduit 422 is connected to outlet orifice 410 and provides for the flow of product out of the reaction zone 407 through orifice 410.

Figure 31:
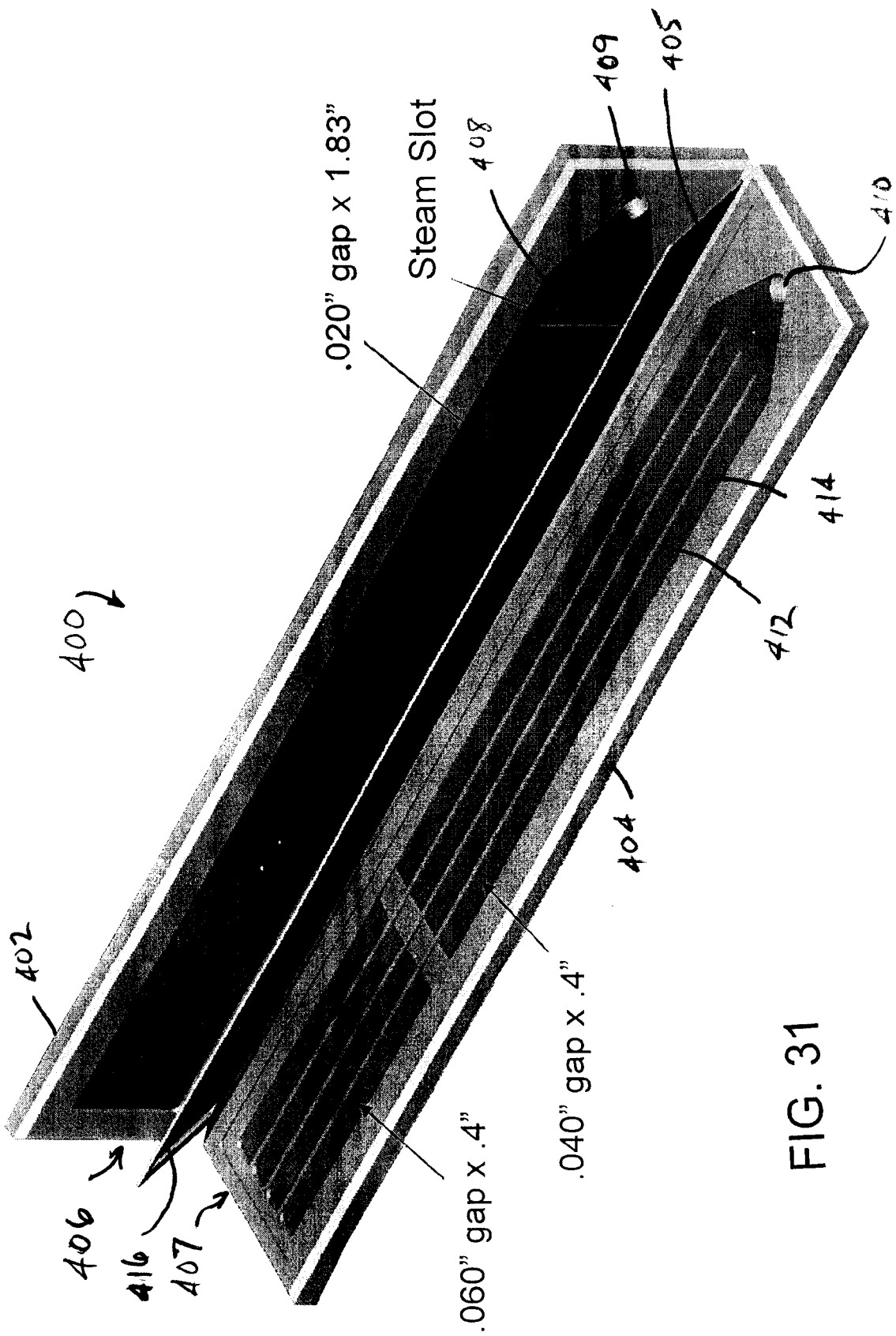
Figure 33:
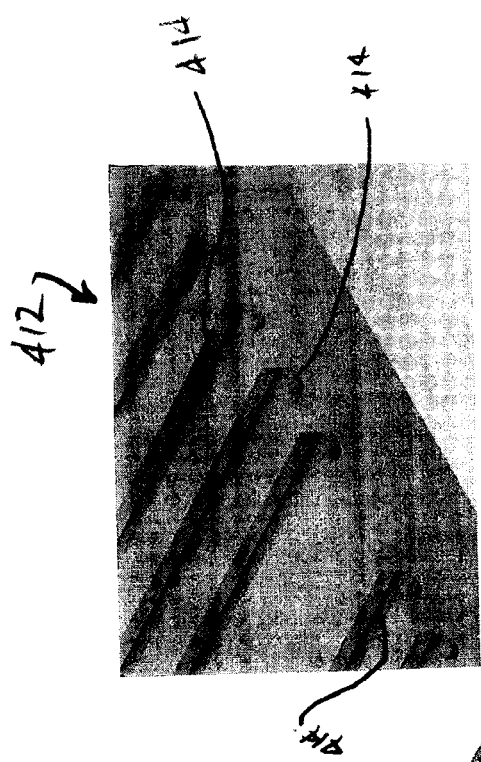
Figure 32:
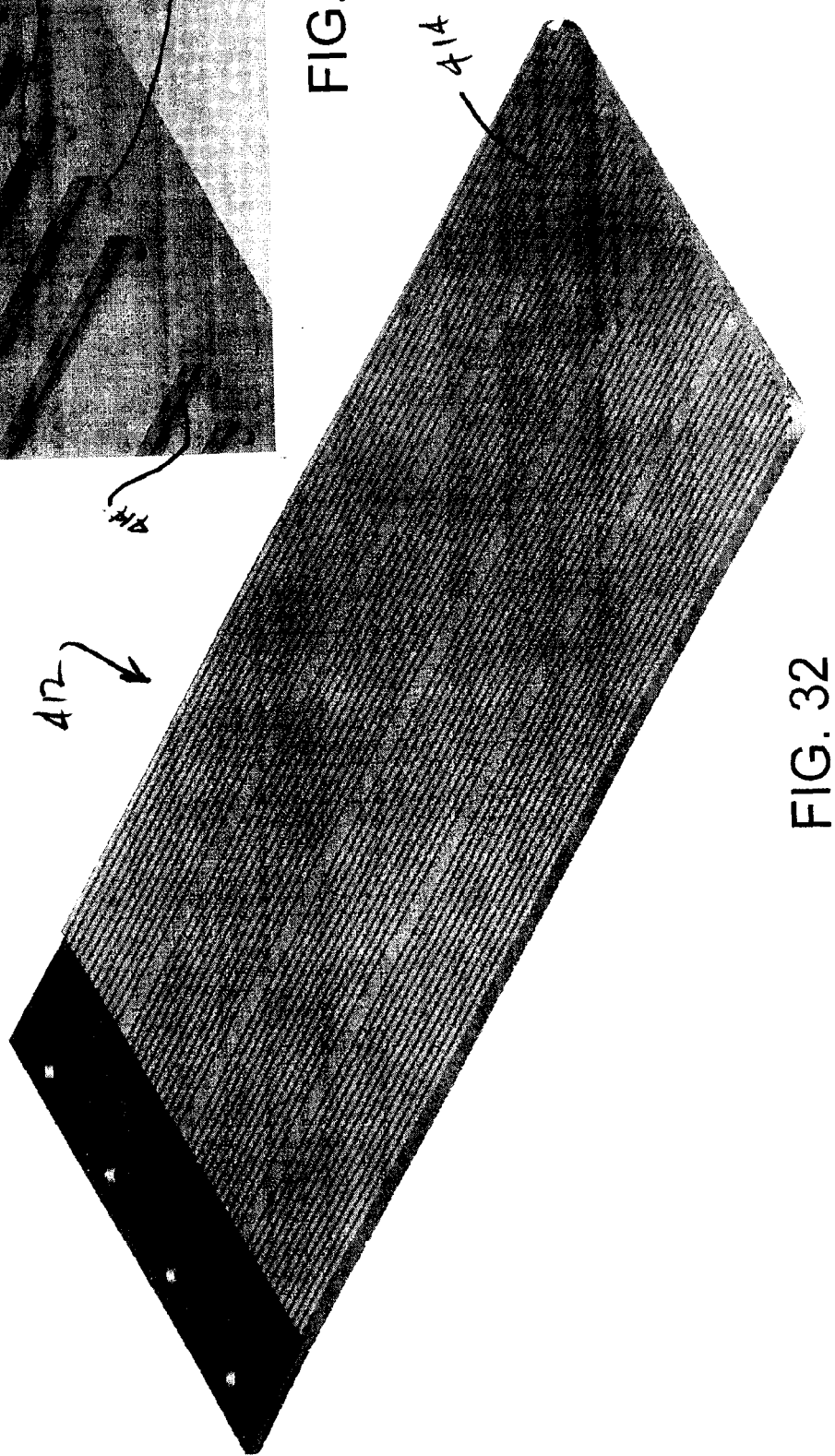
Figure 34:
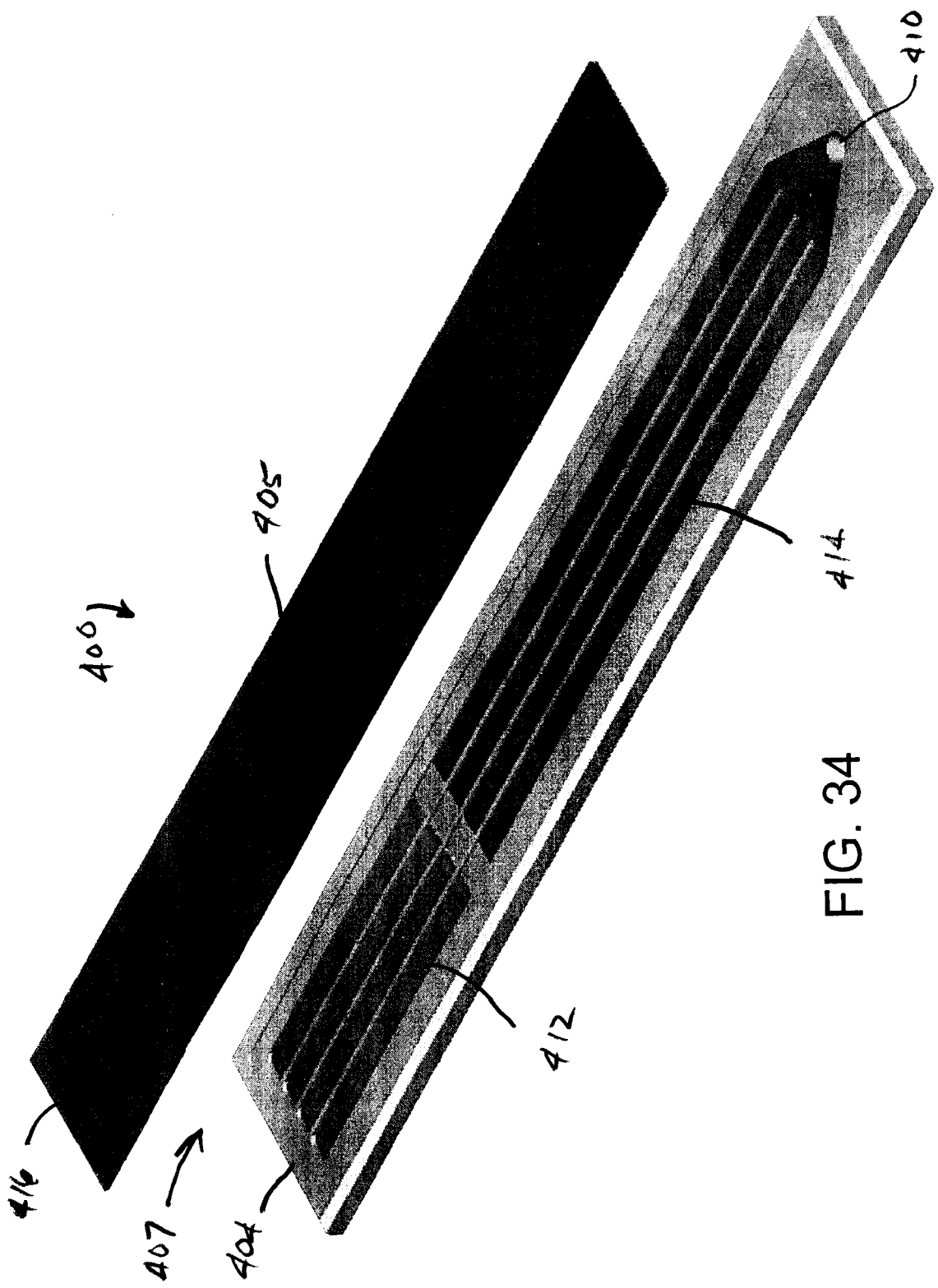
Figure 35:
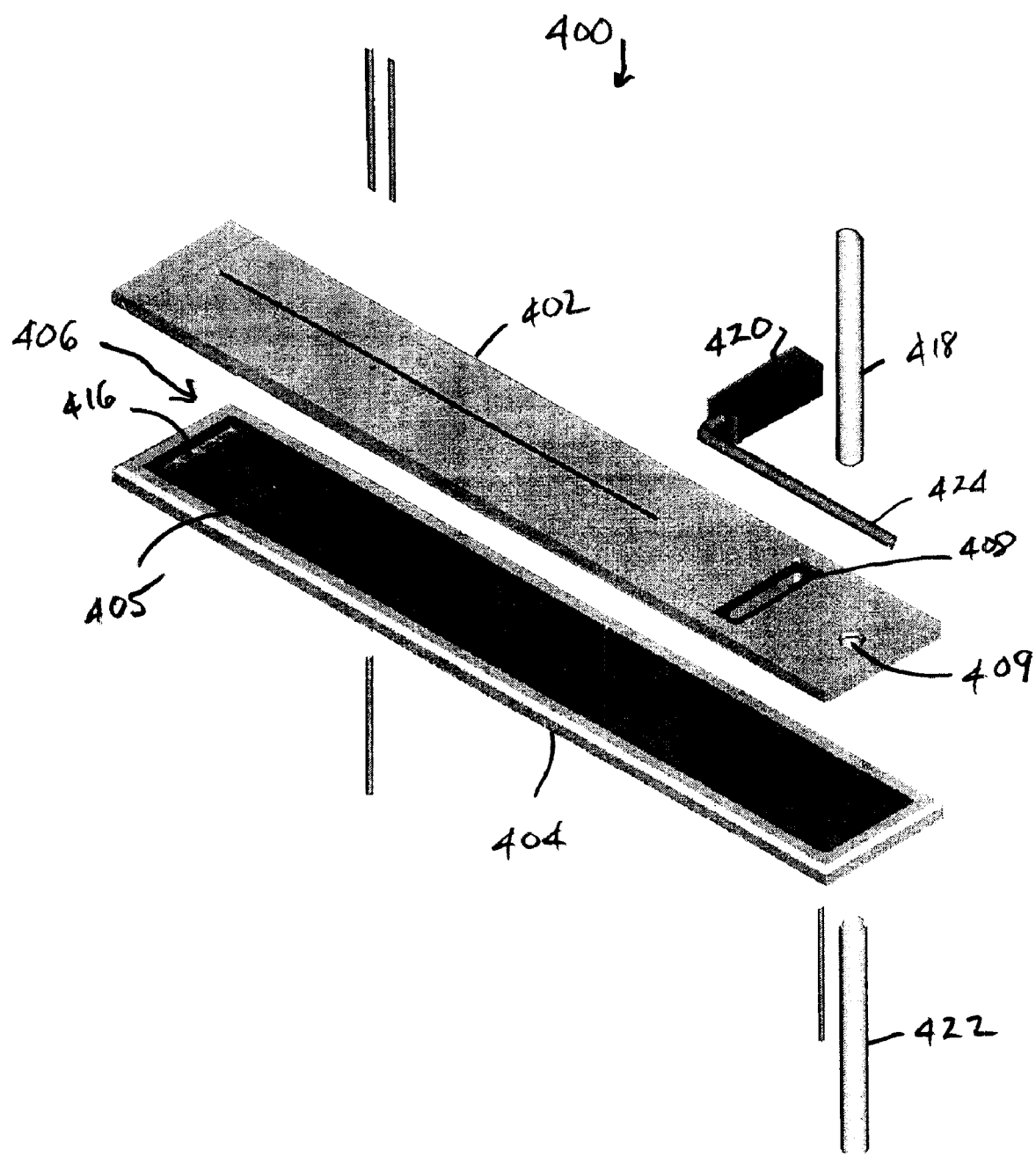

In operation, ethane flows into conduit 418 as indicated by arrow 430, and from conduit 418 through hydrocarbon reactant inlet orifice 409 into preheating zone 406. Steam (or steam in combination with hydrogen and oxygen) flows through conduit 424 as indicated by arrow 432 into steam inlet manifold 420, and from inlet manifold 420 through steam slot 408 into pre-heat zone 406. The ethane and steam (or steam in combination with hydrogen and oxygen) are mixed in the pre-heat zone 406. The mixture of ethane and steam (or steam in combination with hydrogen and oxygen) flows through the preheat zone 406 from right to left as shown in FIG. 31 to and through divider slot 416. The mixture of ethane and steam (or steam in combination with hydrogen and oxygen) flows from divider slot 416 into process microchannels 414, and flows from left to right as indicated in FIG. 31 through the process microchannels 414 to product outlet orifice 410. The resulting product flows through product orifice 410 to and through conduit 422 and out of microchannel reactor 400 as indicated by arrow 434.

Figure 39:
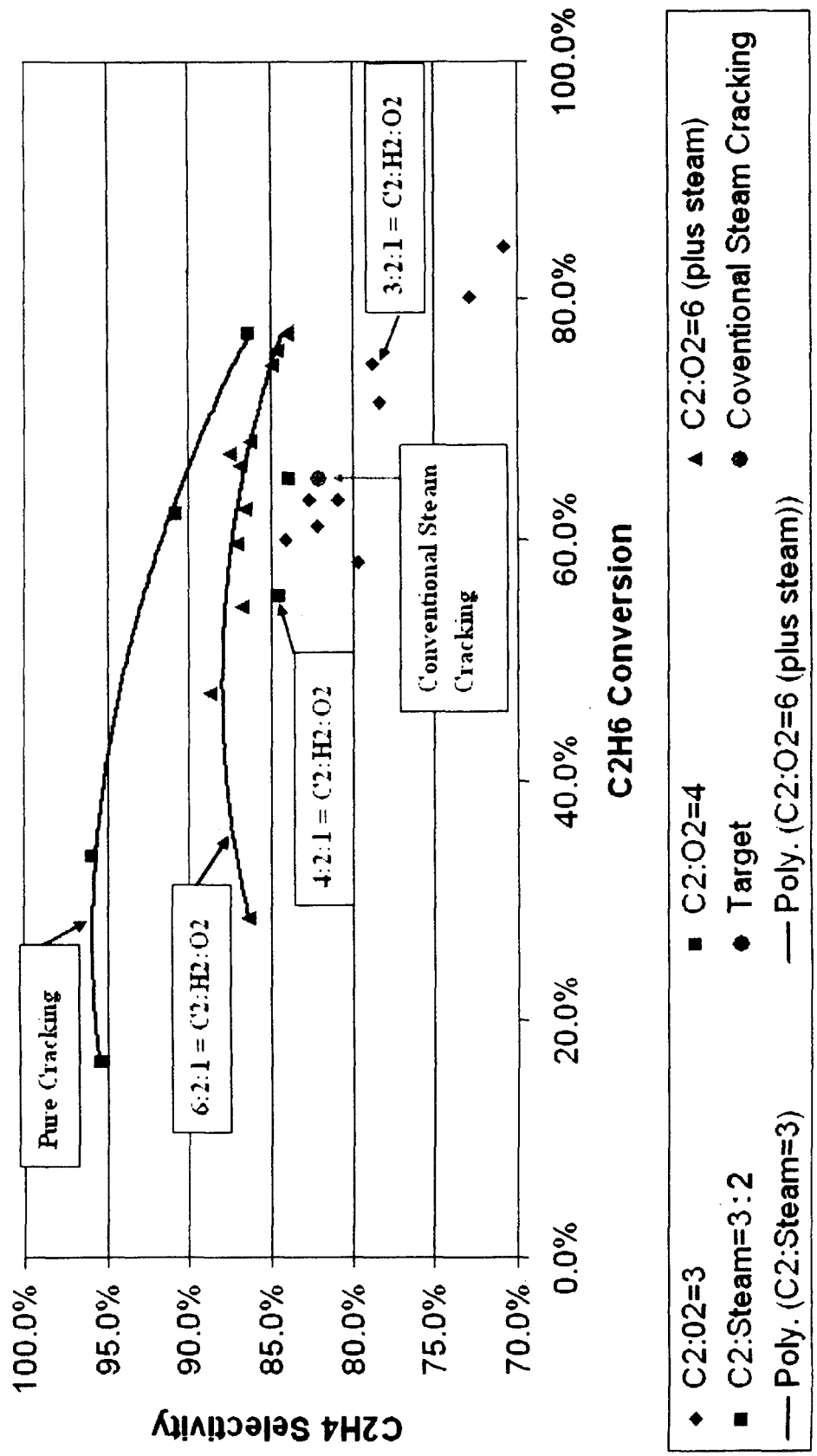
FIG. 39 is a plot showing results described in Example 1.

In a number of production runs, the reactant mixture consists of ethane and steam. The molar ratio of ethane to steam is 3:2. Also, in a number of production runs, part of the steam is substituted with a mixture of hydrogen and oxygen. In these production runs, for each mole of steam that is taken away from the reaction mixture two moles of hydrogen and one mole of oxygen are added. External heaters are used to provide heat to the preheat zone 406 and reaction zone 407. The temperature of the reactants is increased in the preheat zone 406 from 100° C. to 900° C. The temperature in the reaction zone 407 is 950° C. The flow rate of reactants and product is 10 SLPM. The contact times are less than 50 ms. The results are shown in FIG. 39. The conversion of ethane to ethylene is greater than 60% and the selectivity to ethylene is greater than 85% at contact times less than 50 ms.

Example 2

Figure 36:
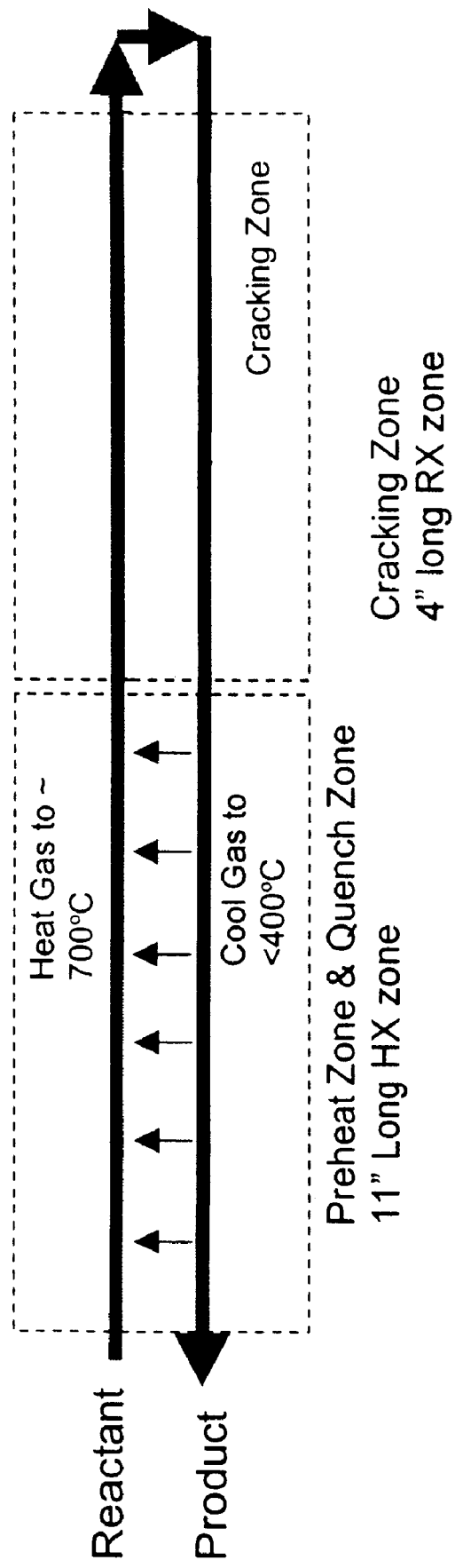
FIG. 36 is a schematic illustration of the microchannel reactor identified in Example 2.
Figure 37:
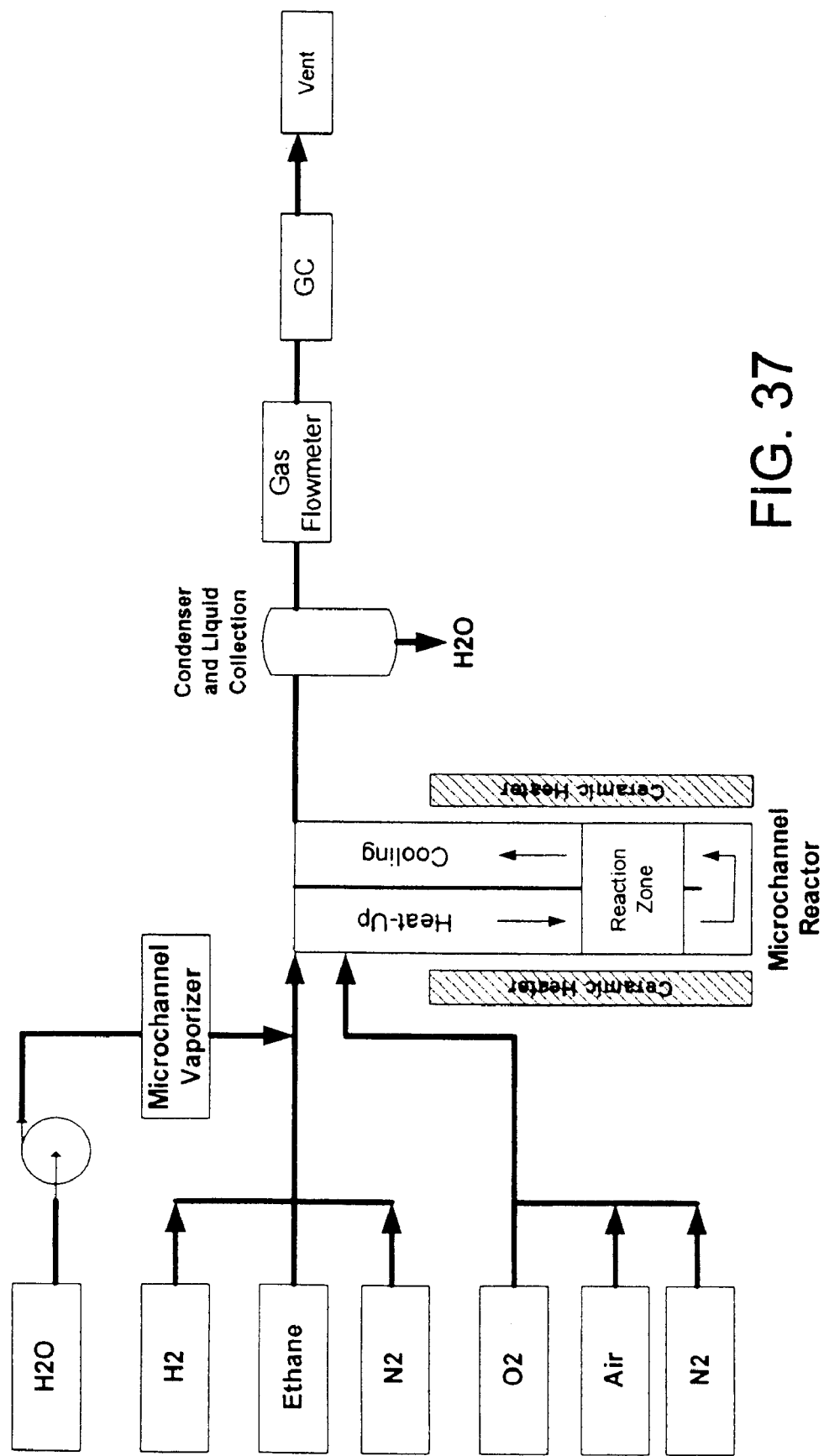
FIG. 37 is a flow sheet showing the process described in Example 2.

The microchannel reactor illustrated in FIGS. 36 and 37 is formed by aligning and joining two Inconel 617 plates and an Inconel 617 separating shim using a perimeter weld. One of the plates may be referred to as a reactant plate. The two plates are 0.37 inch (0.94 cm) thick and each has channels machined into it. One of the plates also has a pocket machined in it to hold a fin. The separating shim is 0.04 inch (1.02 mm) thick. Tubes having a one-half inch diameter are welded onto an inlet and an outlet for use with reactant feed and product outlet. A separate bathtub is welded onto the face of the reactant plate to mix oxygen and/or nitrogen into the feed. After welding, the device is cleaned with dilute nitric acid and aluminized using inlet and outlet ports. After aluminization the interior surfaces are heat treated by flowing air at 1000° C. for four hours using the same inlet and outlet ports as the aluminization. After heat treatment the top one-half inch of the device is cut off using wire EDM. This exposes the pocket for housing the fin. The fin is formed in two halves using wire EDM. A reactor top that is machined, aluminized and heat treated is placed onto the reactor and welded in place to enclose the fin inside the reactor.

The microchannel reactor has a U-turn for flow. The reactor includes an 11 inch (27.9 cm) long heat exchange zone followed by a 4 inch (10.2 cm) long reaction zone. Although the reactor is a single channel device, the channel is subdivided into various parts. In the heat exchange zone the channel has a width of 1.83 inches (4.65 cm) and a height or gap of 0.020 inch (0.51 mm). The heat exchange zone is coupled to a product channel that is subdivided into four smaller sub-channels each having a width of 0.413 inch (1.05 cm) and a height or gap of 0.040 inch (1.02 mm). Ribs separating the product sub-channels have a width of 0.06 inch and are provided for structural support. The reaction zone includes a fin section on the reactant side. The fin contains 48 sub-channels that are 0.015 inch (0.38 mm) wide with a height or gap of 0.015 inch (0.38 mm) and length of 4 inches (10.2 cm). The fins are electrolessly coated with platinum at a level that is less than 5 milligrams per square inch. Although the platinum may be regarded as a catalyst for other reactions, it accounts for no more than 2% of conversion of ethane to ethylene. The product side includes four sub-channels each of which has a width of 0.413 inch (1.05 cm) and a height or gap of 0.060 inch (1.53 mm). The U-turn is located 0.5 inch (1.27 cm) downstream of the fin and has a width of 1.83 inches (4.65 cm) and a height or gap of 0.125 inch (0.318 cm).

A circular, electrically powered ceramic heater is placed around the outside of the microchannel reactor, and only covers the reaction (or cracking) zone, that is, the 4 inch (10.2 cm) section of the microchannel reactor. The rest of the outside surface of the microchannel reactor is insulated with a ceramic insulation. The heater helps account for heat losses in the microchannel reactor. Thermocouples are used to measure the process temperatures. Pressure transdusers are used to monitor the system pressures. The complete thermal profile of the microchannel reactor is measured by two sliding thermocouples that are placed on the outside of the microchannel reactor. Nitrogen is used mainly for start up and shut down, but a small amount of nitrogen is used as a tracer.

Oxygen and/or nitrogen are mixed internally into a feed stream containing ethane, steam and hydrogen via a single slot that spans the 1.83 inch (4.65 cm) reactant channel width and has a gap of 0.010 inch (0.254 mm). The slot is located at the front of the heat exchange zone 11 inches (27.9 cm) upstream of the fin.

A flow sheet for conducting the experiments is shown in FIG. 37. Ethane, hydrogen and nitrogen are metered individually through mass flow controllers and mixed. The resulting ethane feed stream is preheated to 140° C. De-ionized water is pumped into an electrically heated microchannel heat exchanger and vaporized to form steam. The steam is mixed with the ethane feed stream before entering the microchannel reactor. Oxygen, air and nitrogen are metered individually through mass flow controllers, mixed upstream of the microchannel reactor, and enter the reactor as a second feed stream. The reactants flow through the reactor, are heated and react to form product. The product stream exits the reactor and is chilled. Water is condensed. Liquid water is collected in a chilled knock out vessel which is operated at a temperature of 10° C. The dry product gas flow rate is measured with a dry test meter. The product gas is sampled with an Agilent micro-gas chromataragph and analyzed for $H_2$, $N_2$, $O_2$, $CO_2$, $CO$, $C_2H_6$, $C_2H_4$, $C_2H_2$, $C_3H_8$, $C_3H_6$, and $n\text{-}C_4H_{10}$.

Steam slows coke formation. The results show particularly high ethylene selectivities at conversions of less than 70%. The results also show the performance is better with larger $C_2$:$H_2O$ ratios. The results are provided in the following Table 1. The total flow rate is 5 or 10 SLPM as indicated in the table. The contact times are less than 50 ms.

TABLE 1

| Case | Total Flow Rate (SLPM) | C2:Steam | Heater Temp | C2H6 Conversion | C2H4 Selectivity | C2H2 Selectivity | Carbon Balance |
|---|---|---|---|---|---|---|---|
| 1 | 5 | 3:2 | 900 | 16.60% | 95.40% | — | — |
| 2 | 5 | 3:2 | 950 | 34.00% | 95.90% | — | 0.51% |

TABLE 1-continued

| Case | Total Flow Rate (SLPM) | C2:Steam | Heater Temp | C2H6 Conversion | C2H4 Selectivity | C2H2 Selectivity | Carbon Balance |
|---|---|---|---|---|---|---|---|
| 3 | 5 | 3:2 | 1020 | 62.30% | 90.80% | 0.10% | 2.01% |
| 4 | 5 | 3:2 | 1060 | 77.20% | 86.30% | 4.06% | −1.50% |
| 5 | 10 | 1:2 | 900 | 27.04% | 91.18% | 0.39% | −4.17% |
| 6 | 10 | 1:2 | 925 | 38.04% | 91.21% | 0.65% | −4.27% |
| 7 | 10 | 1:2 | 960 | 55.51% | 89.34% | 1.93% | −3.86% |
| 8 | 10 | 1:2 | 990 | 71.92% | 87.91% | 3.94% | −4.98% |
| 9 | 10 | 1:1 | 900 | 21.73% | 93.66% | 0.31% | −2.22% |
| 10 | 10 | 1:1 | 925 | 30.64% | 93.52% | 0.52% | −3.56% |
| 11 | 10 | 1:1 | 960 | 46.66% | 92.61% | 1.10% | −2.09% |
| 12 | 10 | 1:1 | 960 | 45.22% | 93.88% | 1.09% | −3.70% |
| 13 | 10 | 1:1 | 1005 | 65.95% | 90.48% | 2.73% | −4.10% |
| 14 | 10 | 2:1 | 1040 | 76.21% | 84.18% | 5.01% | −2.50% |
| 15 | 10 | 2:1 | 1040 | 73.75% | 86.40% | 5.22% | −2.70% |
| 16 | 10 | 2:1 | 1040 | 73.39% | 86.33% | 5.19% | −3.10% |
| 17 | 10 | 2:1 | 1040 | 72.73% | 87.06% | 5.16% | — |

Example 3

Figure 38:
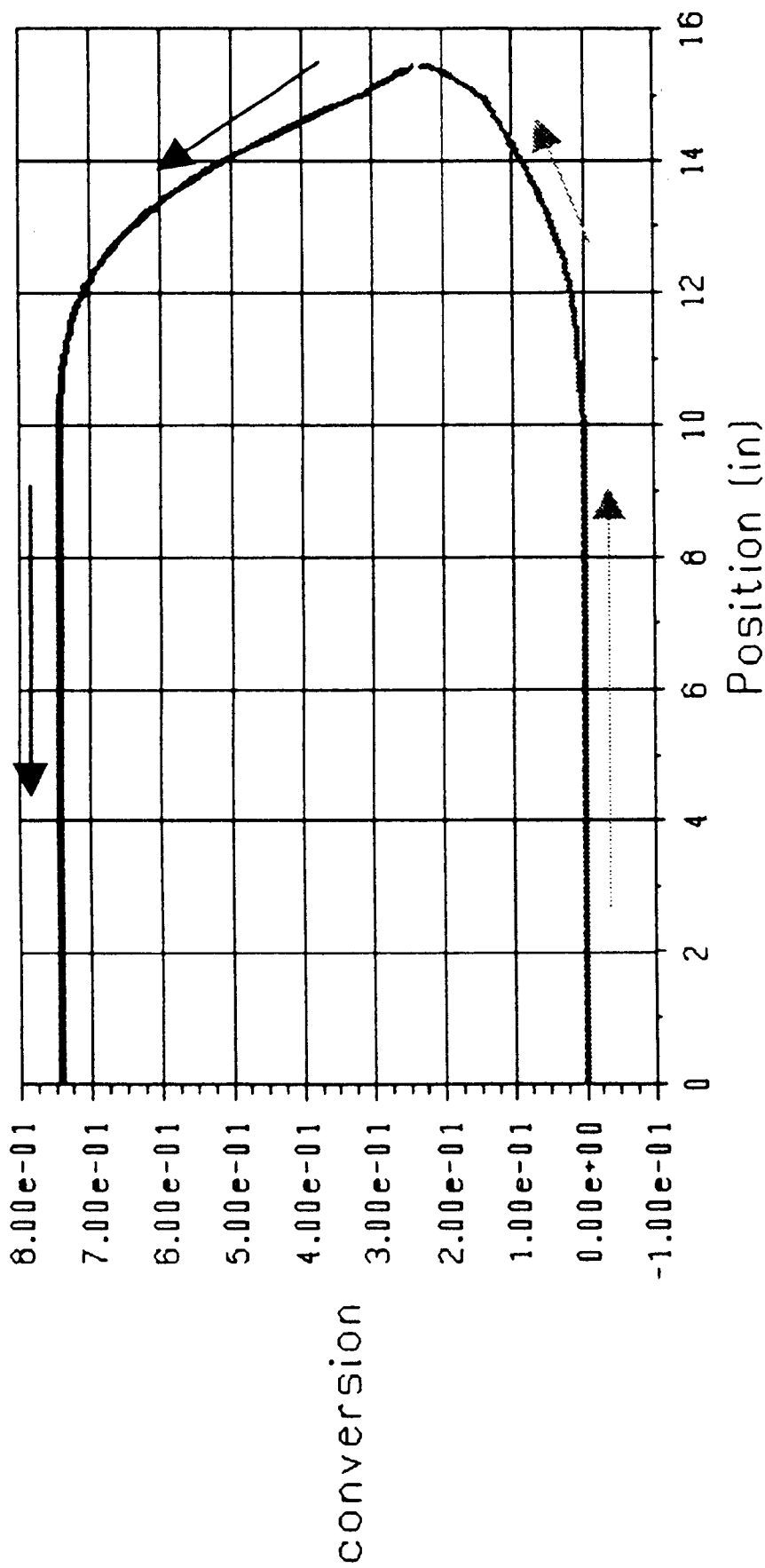
FIG. 38 is a graph showing test results described in Example 3.

A microchannel reactor is modeled to predict the performance from case 4 in Table 1 of Example 2. The feed is: $C_2H_6$ at 2850 standard cubic centimeters per minute (sccm); $N_2$ at 250 sccm; and $H_2O$ at 1.53 ml/min. The ethane to steam ratio is 3:2. The contact times are less than 100 ms. The results are shown in FIG. 38. The majority of the conversion, that is, greater than 50%, occurs after the U-turn in the flow. This region corresponds to a reactor volume that is devoid of any material that may be considered to be a catalyst.

The modeled reactions are shown in Table 2 below. Reactions 2, 3 and 8 do not occur because there is no oxygen in the system. Reaction 1 represents the formation of ethylene from ethane and is a volume reaction that occurs homogeneously, as do reactions 4-7. There are no surface reactions expected for the steam cracking of ethane which is consistent with the agreement of model versus experiment shown in FIG. 38 and in Table 3.

TABLE 2

| No | Reaction | Rate expressions r in Kgmol/m3-s | $A_i$ | $E_i$ J/kgmol |
|---|---|---|---|---|
| 1 | $C_2H_6 \Leftrightarrow C_2H_4 + H_2$ | $r_1 = A_1 \exp(-E_1/RT)C_{H2}$ | 8.5E8 | 1.6E8 |
| 2 | $H_2 + \frac{1}{2}O_2 \rightarrow H_2O$ | $r_2 = A_2 \exp(-E_2/RT)C_{H2}C_{O2}^{0.5}$ | 3.0E10 | 1.64E8 |
| 3 | $C_2H_4 + O_2 \rightarrow 2CO + 2H_2$ | $r_3 = A_3 \exp(-E_3/RT)C_{C2H4}C_{O2}$ | 8.0E12 | 1.8E8 |
| 4 | $C_2H_6 + H_2 \rightarrow 2CH_4$ | $r_4 = A_4 \exp(-E_4/RT)C_{C2H6}$ | 6.0E9 | 2.1E8 |
| 5 | $C_2H_4 \rightarrow C_2H_2 + H_2$ | $r_5 = A_5 \exp(-E_5/RT)C_{C2H4}$ | 2.26E11 | 2.5E8 |
| 6 | $2C_2H_4 \rightarrow C_4H_8$ | $r_6 = A_6 \exp(-E_6/RT)C_{C2H4}$ | 3.5E10 | 2.4E8 |
| 7 | $C_2H_2 + C_2H_4 \rightarrow C_3H_6 + C$ | $r_7 = A_7 \exp(-E_7/RT)C_{C2H4}C_{C2H2}$ | 2.5E16 | 2.7E8 |
| 8 | $H_2 + \frac{1}{2}O_2 \rightarrow H_2O$ (catalyzed) | $r_8 = A_8 \exp(-E_8/RT)C_{H2}C_{O2}^{0.5}$ | 2100 | 4.0E7 |

TABLE 3

| | Conversion | Selectivity | CO | $CO_2$ | $CH_4$ | $C_2H_2$ | $C_3H_6$ | $C_4H_8$ | Carbon Balance |
|---|---|---|---|---|---|---|---|---|---|
| Model | 74.5 | 90.9 | 0 | 0 | 4.3 | 1.3 | 1.2 | 1.8 | −0.4 |
| Experiment | 77.2 | 86.3 | 1.6 | 0.1 | 5.9 | 4.1 | 0.01 | 0 | −1.5 |

While the invention has been explained in relation to various embodiments, it is to be understood that various modifications thereof may become apparent to those skilled in the art upon reading this specification. Therefore, it is to be understood that the invention includes all such modifications that may fall within the scope of the appended claims.

The invention claimed is:

1. A process for converting a feed composition comprising one or more hydrocarbons to a product comprising one or more unsaturated hydrocarbons, the process comprising: flowing the feed composition and steam in contact with each other in a microchannel reactor at a temperature in the range from about 200° C. to about 1200° C. to convert the feed composition to the product, the process being characterized by the absence of catalyst for converting the one or more hydrocarbons to one or more unsaturated hydrocarbons; with the proviso that the microchannel reactor optionally further comprises one or more materials that function as a catalyst for a reaction other than the conversion of the one or more hydrocarbons to the one or more unsaturated hydrocarbons, provided such materials do not increase the conversion of the one or more hydrocarbons to the one or more unsaturated hydrocarbons by more than about 10% of what the conversion would be if such materials were not present.

2. The process of claim 1 wherein the process comprises a cracking process wherein one or more C—C bonds in one or more of the hydrocarbons in the feed composition are ruptured to yield a product comprising one or more hydrocarbons having a lower molecular weight than the one or more hydrocarbons in the feed composition, one or more of the hydrocarbons in the product being the one or more unsaturated hydrocarbons.

3. The process of claim 1 wherein the process comprises a dehydrogenation process wherein one or more C—H bonds in one or more of the hydrocarbons in the feed composition are ruptured to yield hydrogen and the one or more unsaturated hydrocarbons in the product.

4. The process of claim 1 wherein hydrogen flows in the microchannel reactor in contact with the feed composition and steam.

5. The process of claim 1 wherein oxygen flows in the microchannel reactor in contact with the feed composition and steam.

6. The process of claim 1 wherein hydrogen and oxygen flow in the microchannel reactor in contact with the feed composition and steam.

7. The process of claim 1 wherein the feed composition and steam are mixed with each other prior to entering the microchannel reactor.

8. The process of claim 1 wherein the feed composition and steam are mixed with each other in the microchannel reactor.

9. The process of claim 1 wherein part of the steam is mixed with the feed composition prior to entering the microchannel reactor and part of the steam is mixed with the feed composition in the microchannel reactor.

10. The process of claim 1 wherein the microchannel reactor comprises at least one process microchannel, the at least one process microchannel having a feed entrance for permitting the feed composition to enter the at least one process microchannel and at least one staged addition entrance for permitting the steam to enter the at least one process microchannel, the at least one staged addition entrance being downstream of the feed entrance.

11. The process of claim 1 wherein the process is conducted in a microchannel reactor comprises a plurality of process microchannels and at least one header for distributing the feed composition and the steam to the process microchannels, the process further comprising mixing the feed composition and the steam in the header, the resulting mixture of feed composition and steam flowing from the header into the process microchannels.

12. The process of claim 1 wherein the microchannel reactor comprises at least one process microchannel, the feed composition and steam contacting surface features in the at least one process microchannel, the contacting of the surface features with the feed composition and steam imparting a disruptive flow to the feed composition and steam.

13. The process of claim 12 wherein the surface features are oriented at oblique angles relative to the direction of the bulk flow of the feed composition in the at least one process microchannel.

14. The process of claim 12 wherein the surface features comprise two or more layers stacked on top of each other and/or intertwined in one or more three-dimensional patterns.

15. The process of claim 12 wherein the surface features are in the form of circles, oblongs, squares, rectangles, checks, chevrons, wavy shapes, or combinations thereof.

16. The process of claim 12 wherein the surface features comprise sub-features where the major walls of the surface features further contain smaller surface features in the form of notches, waves, indents, holes, burrs, checks, scallops, or combinations thereof.

17. The process of claim 12 wherein the surface features comprise a plurality of interconnected oblique angles.

18. The process of claim 1 wherein the microchannel reactor comprises at least one process microchannel, the at least one process microchannel having an internal dimension of width or height of up to about 10 mm.

19. The process of claim 1 wherein the microchannel reactor comprises at least one process microchannel, the at least one process microchannel being made of a material comprising: steel; monel; inconel; aluminum; titanium; nickel; copper; brass; an alloy of any of the foregoing metals; a polymer; ceramics; glass; a composite comprising a polymer and fiberglass; quartz; silicon; or a combination of two or more thereof.

20. The process of claim 1 wherein the microchannel reactor comprises at least one process microchannel, the at least one process microchannel having a length in the range up to about 10 meters.

21. The process of claim 1 wherein the microchannel reactor comprises at least one process microchannel, the at least one process microchannel being heated by a heat source.

22. The process of claim 21 wherein the heat source comprises at least one heat exchange channel.

23. The process of claim 22 wherein the heat exchange channel comprises a microchannel.

24. The process of claim 22 wherein the heat exchange channel is made of a material comprising: steel; monel; inconel; aluminum; titanium; nickel; copper; brass; an alloy of any of the foregoing metals; a polymer; ceramics; glass; a composite comprising polymer and fiberglass; quartz; silicon; or a combination of two or more thereof.

25. The process of claim 22 wherein a heat exchange fluid is in the heat exchange channel.

26. The process of claim 25 wherein the heat exchange fluid undergoes a phase change in the heat exchange channel.

27. The process of claim 22 wherein an exothermic process is conducted in the heat exchange channel.

28. The process of claim 22 wherein a combustion reaction is conducted in the heat exchange channel.

29. The process of claim 22 wherein the bulk flow direction for the feed composition in the process microchannel is in a first direction, and a heat exchange fluid flows in the heat exchange channel in a second direction, the second direction being cross current relative to the first direction.

30. The process of claim 22 wherein the bulk flow direction for the feed composition in the process microchannel is in a first direction, and a heat exchange fluid flows in the heat exchange channel in a second direction, the second direction being cocurrent or counter current relative to the first direction.

31. The process of claim 22 wherein a heat exchange fluid is in the heat exchange channel, the heat exchange fluid comprising one or more of steam, carbon monoxide, carbon dioxide, gaseous nitrogen, inert gas, gaseous hydrocarbon, liquid hydrocarbon, or a mixture of two or more thereof.

32. The process of claim 21 wherein the heat source comprises an electric heating element and/or resistance heater.

33. The process of claim 21 wherein the at least one process microchannel has at least one heat transfer wall, the heat flux between the heat source and the at least one process microchannel being in the range from about 0.01 to about 500 watts per square centimeter of surface area of the heat transfer wall.

34. The process of claim 1 wherein the microchannel reactor comprises at least one process microchannel, the at least one process microchannel being in thermal contact with a plurality of heat exchange zones, the temperature in each heat exchange zone being different.

35. The process of claim 1 wherein the microchannel reactor comprises at least one process microchannel, the product being quenched in the at least one process microchannel.

36. The process of claim 1 wherein the product flows out of the microchannel reactor and is quenched.

37. The process of claim 1 wherein the feed composition is preheated and the product is quenched, the product being quenched transferring heat to the feed composition being preheated.

38. The process of claim 1 wherein the microchannel reactor comprises at least one process microchannel, the feed composition being preheated in the at least one process microchannel and the product being quenched in the at least one process microchannel, the product being quenched transferring heat to the feed composition being preheated.

39. The process of claim 1 wherein the feed composition comprises one or more saturated hydrocarbon compounds, one or more unsaturated hydrocarbon compounds, one or more hydrocarbyl substituted aromatic compounds, or a mixture of two or more thereof.

40. The process of claim 1 wherein the feed composition comprises one or more alkanes of 2 to about 25 carbon atoms.

41. The process of claim 1 wherein the feed composition comprises mineral oil, synthetic oil, atmospheric gas oil, straight run gas oil, vacuum gas oil, demetallized oil, deasphalted vacuum residue, coker distillate, cat cracker distillate, shale oil, tar sand oil, coal liquid, or a mixture of two or more thereof.

42. The process of claim 1 wherein the steam is at a temperature in the range from about 100° C. to about 1100° C. at the entrance to the microchannel reactor.

43. The process of claim 4 wherein the hydrogen is derived from a steam reforming process, partial oxidation process, autothermal reforming process, carbon dioxide reforming process, coal gassification process, or a combination of two or more thereof.

44. The process of claim 5 wherein the oxygen is from a source of oxygen which comprises air, oxygen enriched air, a nitrogen oxide, carbon dioxide, carbon monoxide, a peroxide, a gaseous mixture comprising oxygen and at least one inert gas and/or a diluent gas, or a mixture of two or more thereof.

45. The process of claim 1 wherein the pressure in the microchannel reactor is in the range from about 1 to about 100 atmospheres.

46. The process of claim 1 wherein the Q-factor for the microchannel reactor is less than about 50%.

47. The process of claim 1 wherein the microchannel reactor comprises at least one process microchannel and fluid is flowing in the at least one process microchannel, the superficial velocity for fluid flowing in the at least one process microchannel being at least about 0.01 m/s.

48. The process of claim 1 wherein the product comprises one or more unsaturated aliphatic compounds.

49. The process of claim 1 wherein the product comprises one or more hydrocarbylene substituted aromatic compounds.

50. The process of claim 1 wherein the product comprises ethylene, propylene, butene, isobutene, 1-pentene, 1-hexene, 1-octene, 1-nonene, 1-decene, 1-dodecene, styrene, or a mixture of two or more thereof.

51. The process of claim 1 wherein the product comprises a middle distillate boiling in the range from about 125° C. to about 375° C. at atmospheric pressure.

52. The process of claim 1 wherein the product comprises a $C_5$ to about 205° C. end point distillate fraction.

53. The process of claim 1 wherein the product comprises diesel fuel, jet fuel, kerosene, gasoline, naphtha, or a mixture of two or more thereof.

54. A process for converting a feed composition comprising ethane to a product comprising ethylene, the process comprising: flowing the feed composition and steam in contact with each other in a microchannel reactor at a temperature in the range from about 700° C. to about 1100° C. to convert the feed composition to the product, the process being characterized by the absence of catalyst for converting ethane to ethylene; with the proviso that the microchannel reactor optionally further comprises one or more materials that function as a catalyst for a reaction other than the conversion of ethane to ethylene, provided such materials do not increase the conversion of ethane to ethylene by more than about 10% of what the conversion would be if such materials were not present.

55. The process of claim 1 wherein the microchannel reactor comprises one or more interior surfaces wherein one or more passivation layers are on one or more of the interior surfaces.

56. The process of claim 1 wherein the contact time is in the range from about 1 to about 100 ms.

57. The process of claim 1 wherein reactants and product flow through the microchannel reactor, the reactants and product flowing through the microchannel reactor at a rate of at least about 5 standard liters per minute.

* * * * *